(12) United States Patent
Ahmer et al.

(10) Patent No.: US 10,752,933 B2
(45) Date of Patent: Aug. 25, 2020

(54) METHODS FOR THE IDENTIFICATION, CHARACTERIZATION, AND USE OF INHIBITORS OF THE FRUCTOSE-ASPARAGINE UTILIZATION PATHWAY

(71) Applicants: SABER BIOTICS, LLC, Lewis Center, OH (US); OHIO STATE INNOVATION FOUNDATION, Columbus, OH (US)

(72) Inventors: Brian Ahmer, Lewis Center, OH (US); Anice Sabag-Daigle, Columbus, OH (US)

(73) Assignees: SABER BIOTICS, LLC, Lewis Center, OH (US); OHIO STATE INNOVATION FOUNDATION, Columbus, OH (US)

(*) Notice: Subject to any disclaimer, the term of this patent is extended or adjusted under 35 U.S.C. 154(b) by 0 days.

(21) Appl. No.: 15/580,666

(22) PCT Filed: Jun. 27, 2016

(86) PCT No.: PCT/US2016/039645
§ 371 (c)(1),
(2) Date: Dec. 7, 2017

(87) PCT Pub. No.: WO2016/210436
PCT Pub. Date: Dec. 29, 2016

(65) Prior Publication Data
US 2018/0187238 A1 Jul. 5, 2018

Related U.S. Application Data

(60) Provisional application No. 62/185,538, filed on Jun. 26, 2015, provisional application No. 62/207,881, filed on Aug. 20, 2015.

(51) Int. Cl.
*C12Q 1/04* (2006.01)

(52) U.S. Cl.
CPC ....... *C12Q 1/045* (2013.01); *G01N 2333/255* (2013.01)

(58) Field of Classification Search
CPC ..... G01N 2333/255; C12Q 1/045; C12Q 1/04
See application file for complete search history.

(56) References Cited

U.S. PATENT DOCUMENTS 6,020,173 A  2/2000  Kanzaki et al.

FOREIGN PATENT DOCUMENTS

| WO | 94/28163 A | 12/1994 |
| WO | 97/32034 A | 9/1997 |

OTHER PUBLICATIONS

Ali et al., (PLoS Pathogens, Jun. 2014, vol. 10, No. 6, e004209: pp. 1-15) . (Year: 2014).*

(Continued)

*Primary Examiner* — Jana A Hines
(74) *Attorney, Agent, or Firm* — Wiley Rein LLP

(57) ABSTRACT

The present embodiments provide for media useful for selection and enrichment of *Salmonella* species. In a particular embodiment, the medium is a minimal medium that includes fructose-asparagine as the sole nutrient source. The fructose-asparagine utilization pathway, particularly FraB, provides a highly selective drug target for inhibiting *Salmonella enterica*.

5 Claims, 25 Drawing Sheets
Specification includes a Sequence Listing.

(56) References Cited

OTHER PUBLICATIONS

Ali et al., (PLoS Pathogens, Jun. 2014, vol. 10, No. 6, e004209: pp. 1-15) entitled Fructose-Asparagine Is a Primary Nutrient during Growth of *Salmonella* in the Inflamed Intestine). (Year: 2014).*

International Preliminary Report on Patentability dated Jan. 4, 2018, issued in related International application No. PCT/US2016/039645, filed Jun. 27, 2016.

Ali, M. et al., "Ructose-Asaragine is a Primary Nutrient during Growth of *Salmonella* in the Inflamed Intestine," PLoS Pathogens, Jun. 2014, vol. 10, No. 6, e1004209, pp. 1-15.

International Search Report and Written Opinion dated Nov. 23, 2016, in International Patent Application No. PCT/US2016/039645, filed Jun. 27, 2016.

Labrat, "M9 Minimal Media Recipe (1000 ml)," Publication [online]. Jan. 10, 2004 [retrieved Nov. 2, 2016]. Retrieved from the Internet: <URL: https://web.archive.org/web/20040110115308/http://www.thelabrat.com/protocols/m9minimal.shtml>.

* cited by examiner

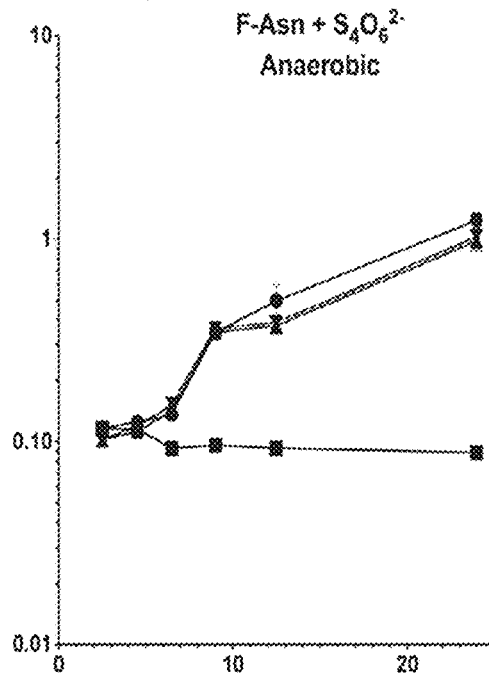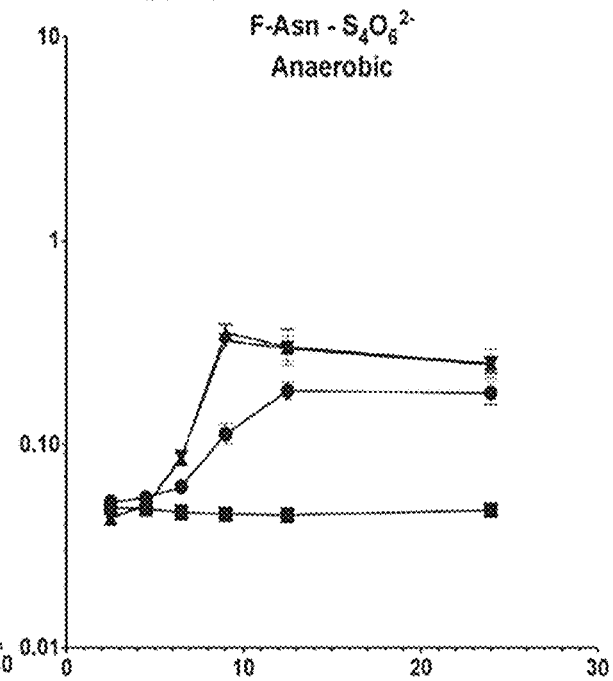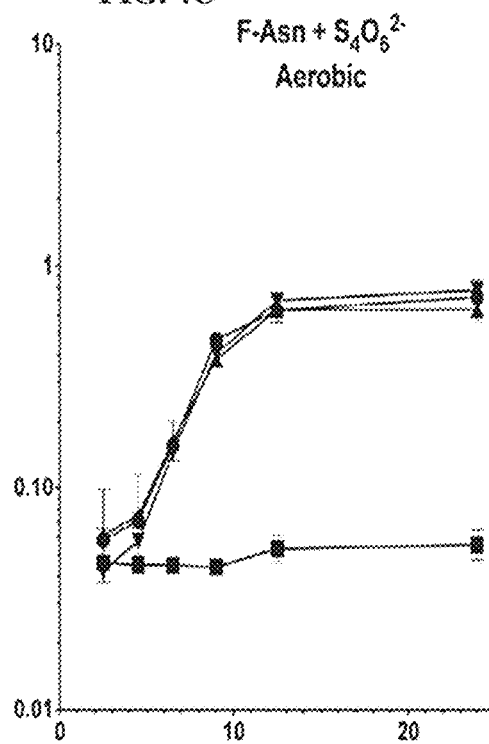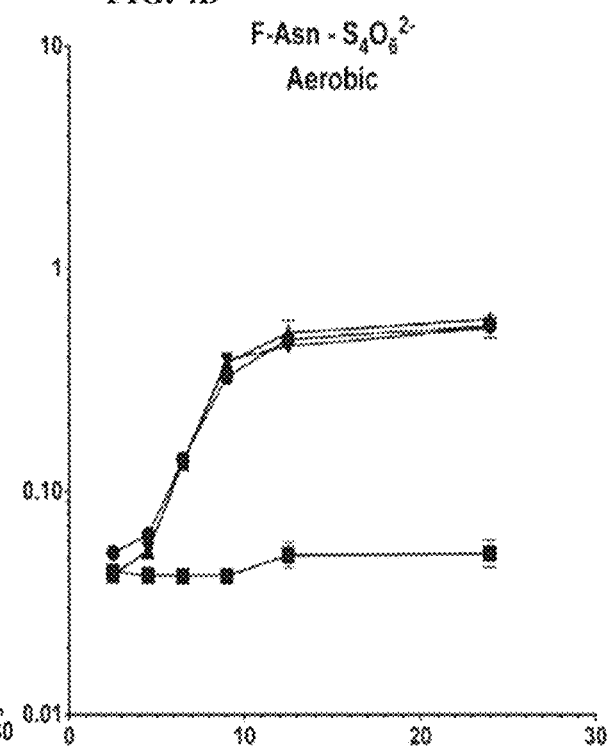

FIG. 10A
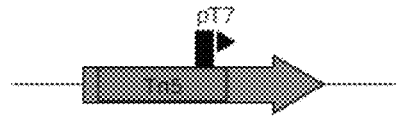
FIG. 10B
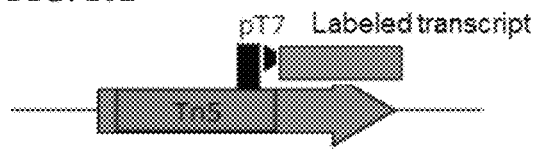
FIG. 10C
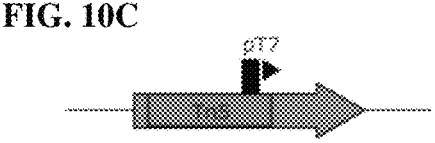
FIG. 10D
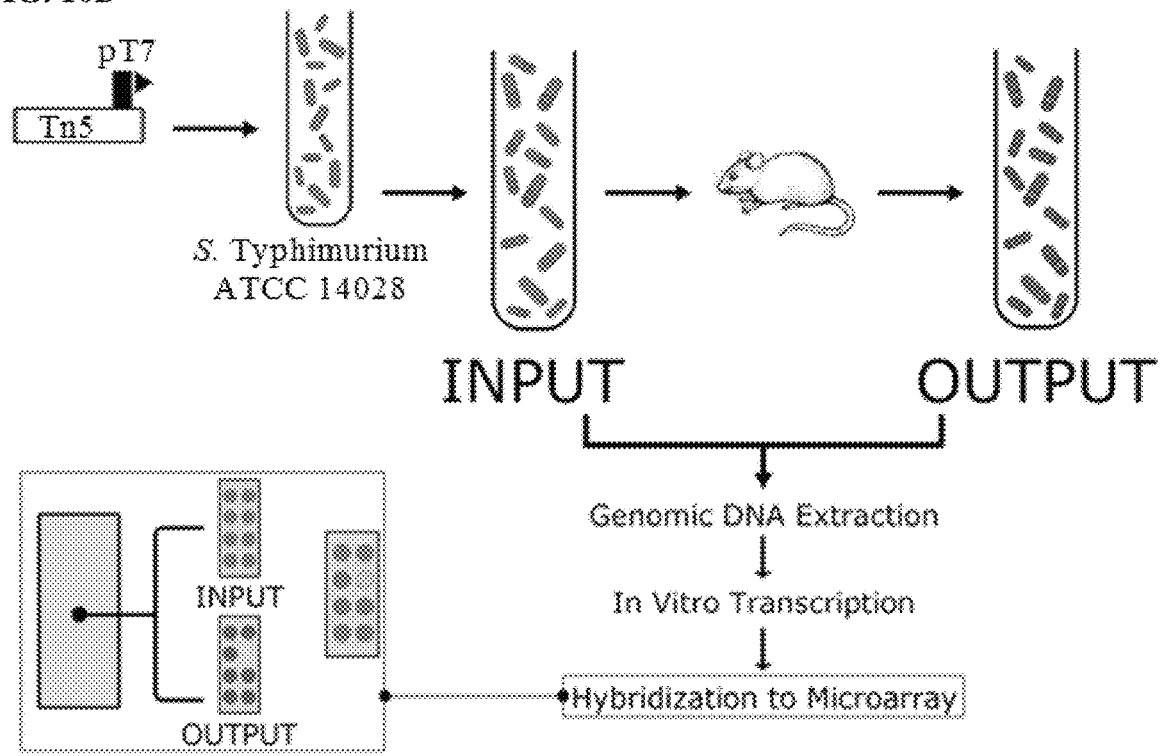

FIG. 17
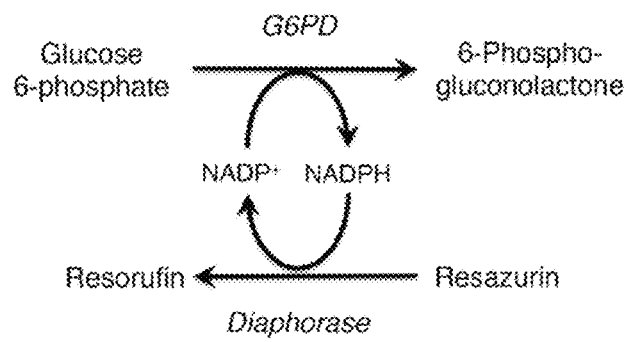
FIG. 18A     FIG. 18B     FIG. 18C
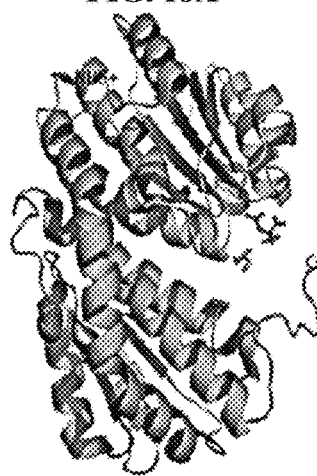 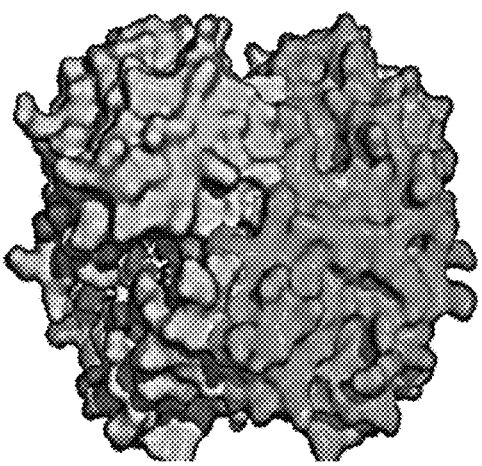 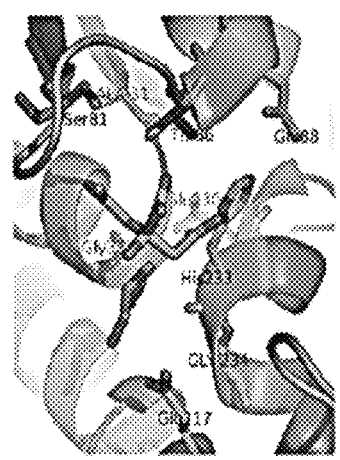
FIG. 19

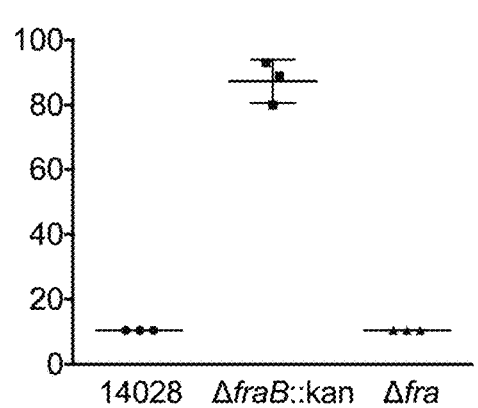
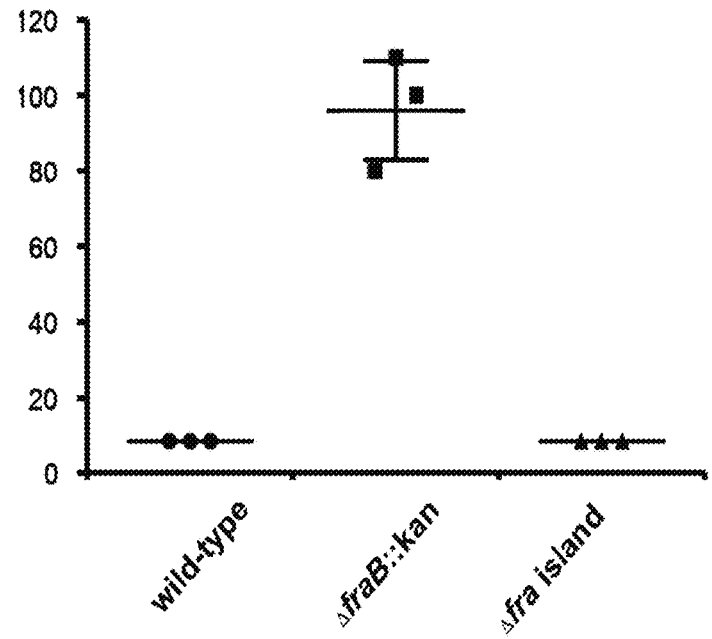
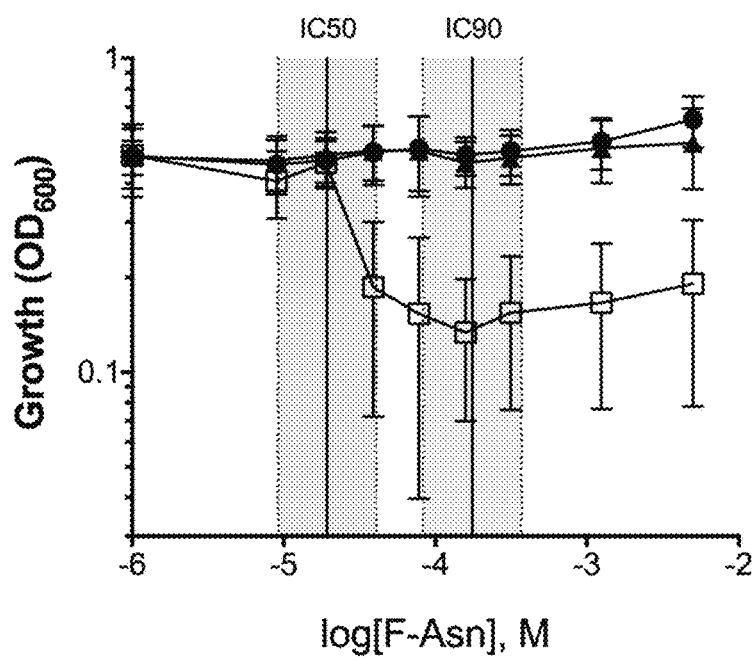

SEQUENCE LISTING

<160> NUMBER OF SEQ ID NOS: 28

<210> SEQ ID NO 1
<211> LENGTH: 157
<212> TYPE: DNA
<213> ORGANISM: Salmonella enterica

<400> SEQUENCE: 1

```
tgtcagcatt acgctaacga agagcaggct gaatcgggat ccagatcgcg gatcccgatt      60 tttttttggtt tccatcttga tcaaatgtct ttaaatgtca tataaaaata ataatacatt    120
atgagtcatt tatggcgaat cctcgcctgt atcattg                               157
```

```
<210> SEQ ID NO 2
<211> LENGTH: 1320
<212> TYPE: DNA
<213> ORGANISM: Salmonella enterica
```

<400> SEQUENCE: 2

```
atgtttttgga cggaattatg ttttatcctt gtggccctga tgataggcgc caggatcggc      60
ggcgtatttt tagggatggt cggcgggtta ggcgtcggcg tgatggtttt tattttttggc    120 ctgacgcctt ctacgccacc gattgatgtt attctgatta ttctttctgt tgtcctggcg    180
gccgcttctt tacaggcctc cggcgggctg gatttactgg tcaaactggc ggaaaaaatt    240
ctgcgtcgcc acccgcgtta cattacgtta ttagcgccgt ttatctgtta tatcttcact    300
tttatgtcag gaacggggca tgtcgtttat agcttgctac cggttatttc tgaagtcgca    360
cgggattcag gtattcgacc ggaacgtcct ttatctattt ccgttatcgc atcgcaacag    420
gcgatcaccg ccagtcctat atctgccgcc atggcggcga tgattggttt aatggcgccg    480
ttgggcgtct ctatttcaac cattatgatg atttgcgtgc cgccacgtt aatcggcgta    540 gcgatggggg caatagcgac ctttaataaa ggaaaagagt taaaagacga tccggaatat    600
caacgtcggc ttgctgaagg gttaattaaa cctgcgcaga agaaagtaa aaatacggtg    660 gtcacttcgc gcgccaaatt gtcggtggcg ttatttctga ccagtgcgat cgttatcgtt    720
ctgttaggac tgattccggc gctgcggccc atggtggaaa cagcgaaagg ctacaaccg    780 ctttcgatgt ccgccgctat ccagattacg atgctctctt tgcctgcct gattgtgttg    840 ttatgccgac gcaggtcga tcaaattatc agcggtacgg tatttcgggc gggcgcgctg    900
gcgattgtct gcgccttcgg cctggcctgg atgagtgaga cgttcgtgaa tggtcatatc    960
gcgttgatta aggcagaagt gcaaactcta ttgcaacagc ataccctgggct tatcgccatt   1020 atgatgtttt ttgtgtccgc tatggtcagc agccaggcgg caacgacgtt aattctgttg   1080
ccgctggggc tggcgttagg gttgcccgct tatgcattaa tcggctcctg gcctgccgtt   1140
aacggctatt tctttattcc ggtggcgggg cagtgtctgg cggcgctggc gtttgacgat   1200
accggtacga cgcgtattgg caaatatgtg cttaaccata gttttatgcg tccgggatta   1260
gttaacgtga ttgtctcggt cattgtcggg ctgttaatag gaaaaatggt tctggcctga   1320
```

```
<210> SEQ ID NO 3
<211> LENGTH: 439
<212> TYPE: PRT
<213> ORGANISM: Salmonella enterica
```

<400> SEQUENCE: 3

```
Met Phe Trp Thr Glu Leu Cys Phe Ile Leu Val Ala Leu Met Ile Gly
1               5                   10                  15

Ala Arg Ile Gly Gly Val Phe Leu Gly Met Val Gly Gly Leu Gly Val
            20                  25                  30

Gly Val Met Val Phe Ile Phe Gly Leu Thr Pro Ser Thr Pro Pro Ile
        35                  40                  45

Asp Val Ile Leu Ile Ile Leu Ser Val Val Leu Ala Ala Ala Ser Leu
    50                  55                  60
```

Gln Ala Ser Gly Gly Leu Asp Leu Leu Val Lys Leu Ala Glu Lys Ile
 65                  70                  75                  80

Leu Arg Arg His Pro Arg Tyr Ile Thr Leu Leu Ala Pro Phe Ile Cys
                 85                  90                  95

Tyr Ile Phe Thr Phe Met Ser Gly Thr Gly His Val Val Tyr Ser Leu
            100                 105                 110

Leu Pro Val Ile Ser Glu Val Ala Arg Asp Ser Gly Ile Arg Pro Glu
        115                 120                 125

Arg Pro Leu Ser Ile Ser Val Ile Ala Ser Gln Gln Ala Ile Thr Ala
130                 135                 140

Ser Pro Ile Ser Ala Ala Met Ala Ala Met Ile Gly Leu Met Ala Pro
145                 150                 155                 160

Leu Gly Val Ser Ile Ser Thr Ile Met Met Ile Cys Val Pro Ala Thr
                165                 170                 175

Leu Ile Gly Val Ala Met Gly Ala Ile Ala Thr Phe Asn Lys Gly Lys
            180                 185                 190

Glu Leu Lys Asp Asp Pro Glu Tyr Gln Arg Arg Leu Ala Glu Gly Leu
        195                 200                 205

Ile Lys Pro Ala Gln Lys Glu Ser Lys Asn Thr Val Val Thr Ser Arg
210                 215                 220

Ala Lys Leu Ser Val Ala Leu Phe Leu Thr Ser Ala Ile Val Ile Val
225                 230                 235                 240

Leu Leu Gly Leu Ile Pro Ala Leu Arg Pro Met Val Glu Thr Ala Lys
                245                 250                 255

Gly Leu Gln Pro Leu Ser Met Ser Ala Ala Ile Gln Ile Thr Met Leu
            260                 265                 270

Ser Phe Ala Cys Leu Ile Val Leu Leu Cys Arg Pro Gln Val Asp Gln
        275                 280                 285

Ile Ile Ser Gly Thr Val Phe Arg Ala Gly Ala Leu Ala Ile Val Cys
290                 295                 300

Ala Phe Gly Leu Ala Trp Met Ser Glu Thr Phe Val Asn Gly His Ile
305                 310                 315                 320

Ala Leu Ile Lys Ala Glu Val Gln Thr Leu Leu Gln Gln His Thr Trp
                325                 330                 335

Leu Ile Ala Ile Met Met Phe Phe Val Ser Ala Met Val Ser Ser Gln
            340                 345                 350

Ala Ala Thr Thr Leu Ile Leu Leu Pro Leu Gly Leu Ala Leu Gly Leu
        355                 360                 365

Pro Ala Tyr Ala Leu Ile Gly Ser Trp Pro Ala Val Asn Gly Tyr Phe
370                 375                 380

Phe Ile Pro Val Ala Gly Gln Cys Leu Ala Ala Leu Ala Phe Asp Asp
385                 390                 395                 400

Thr Gly Thr Thr Arg Ile Gly Lys Tyr Val Leu Asn His Ser Phe Met
                405                 410                 415

Arg Pro Gly Leu Val Asn Val Ile Val Ser Val Ile Val Gly Leu Leu
            420                 425                 430

Ile Gly Lys Met Val Leu Ala
            435

<210> SEQ ID NO 4
<211> LENGTH: 978
<212> TYPE: DNA
<213> ORGANISM: Salmonella enterica

```
<400> SEQUENCE: 4
atgatgggta tgaaagagac agttagcaat attgtgacca gccaggcaga gaaaggaggc    60
gttaaacacg tctattacgt ggcgtgcggc ggttcttatg cggcgttcta tccggcgaaa   120 gcattttag aaaagaagc gaaagcgttg actgtcggtc tgtataacag cggagaattt    180
attaacaacc cgccggtagc gctgggagaa aatgccgttg tggttgtcgc ctcccacaaa   240
ggtaatacgc cagagacaat taaagcggct gaaatcgccc gtcagcacgg cgcgccggtc   300
attggtttaa cctggataat ggattcaccg ttggtggcgc attgcgacta tgtggaaacg   360
tacacgtttg gcgacggtaa agatattgcc ggagagaaaa cgatgaaagg cctgctgagt   420
gcggtcgaac tgctccagca gacggaaggg tatgcgcact acgacgattt tcaggatggc   480
gtcagcaaaa tcaaccgtat cgtctggcgc gcttgcgagc aggtagcgga gcgtgcgcag   540
gcgttcgcgc aggaatataa agacgataaa gtcatttata ccgtcgccag cggcgcgggc   600
tatggcgcag cctacctaca gagcatctgc atctttatgg aaatgcaatg gatacattcc   660
gcctgtattc atagcggtga gttttccac gggccgtttg aaattaccga tgcgaatacg   720
cctttcttct tccagttttc cgagggcaat acgcgggcgg tggatgaacg cgcgttaaac   780
ttcctgaaaa aatatggccg ccggattgaa gttgtcgatg cgaaagaact ggggctatcg   840
accattaaaa ccacggttat tgattacttt aaccactctc tctttaataa cgtttatccc   900
gtttacaatc gggcgttagc tgaggcgcgt cagcatccgt aacgacgcg ccgctatatg    960 tggaaagtgg aatattaa                                                978

<210> SEQ ID NO 5
<211> LENGTH: 324
<212> TYPE: PRT
<213> ORGANISM: Salmonella enterica

<400> SEQUENCE: 5

Met Gly Met Lys Glu Thr Val Ser Asn Ile Val Thr Ser Gln Ala Glu
 1               5                  10                  15

Lys Gly Gly Val Lys His Val Tyr Tyr Val Ala Cys Gly Gly Ser Tyr
             20                  25                  30

Ala Ala Phe Tyr Pro Ala Lys Ala Phe Leu Glu Lys Glu Ala Lys Ala
         35                  40                  45

Leu Thr Val Gly Leu Tyr Asn Ser Gly Glu Phe Ile Asn Asn Pro Pro
     50                  55                  60

Val Ala Leu Gly Glu Asn Ala Val Val Val Ala Ser His Lys Gly
 65                  70                  75                  80

Asn Thr Pro Glu Thr Ile Lys Ala Ala Glu Ile Ala Arg Gln His Gly
                 85                  90                  95

Ala Pro Val Ile Gly Leu Thr Trp Ile Met Asp Ser Pro Leu Val Ala
            100                 105                 110

His Cys Asp Tyr Val Glu Thr Tyr Thr Phe Gly Asp Gly Lys Asp Ile
        115                 120                 125

Ala Gly Glu Lys Thr Met Lys Gly Leu Leu Ser Ala Val Glu Leu Leu
    130                 135                 140

Gln Gln Thr Glu Gly Tyr Ala His Tyr Asp Asp Phe Gln Asp Gly Val
145                 150                 155                 160

Ser Lys Ile Asn Arg Ile Val Trp Arg Ala Cys Glu Gln Val Ala Glu
                165                 170                 175

Arg Ala Gln Ala Phe Ala Gln Glu Tyr Lys Asp Asp Lys Val Ile Tyr
            180                 185                 190
```

Thr Val Ala Ser Gly Ala Gly Tyr Gly Ala Ala Tyr Leu Gln Ser Ile
                195                 200                 205

Cys Ile Phe Met Glu Met Gln Trp Ile His Ser Ala Cys Ile His Ser
        210                 215                 220

Gly Glu Phe Phe His Gly Pro Phe Glu Ile Thr Asp Ala Asn Thr Pro
225                 230                 235                 240

Phe Phe Phe Gln Phe Ser Glu Gly Asn Thr Arg Ala Val Asp Glu Arg
                245                 250                 255

Ala Leu Asn Phe Leu Lys Lys Tyr Gly Arg Arg Ile Glu Val Val Asp
                260                 265                 270

Ala Lys Glu Leu Gly Leu Ser Thr Ile Lys Thr Thr Val Ile Asp Tyr
            275                 280                 285

Phe Asn His Ser Leu Phe Asn Asn Val Tyr Pro Val Tyr Asn Arg Ala
            290                 295                 300

Leu Ala Glu Ala Arg Gln His Pro Leu Thr Thr Arg Arg Tyr Met Trp
305                 310                 315                 320

Lys Val Glu Tyr

<210> SEQ ID NO 6
<211> LENGTH: 846
<212> TYPE: DNA
<213> ORGANISM: Salmonella enterica

<400> SEQUENCE: 6
atgagcatca gcgtattggg tattggcgac aacgttgtcg ataaatacct gcattccggc      60
atcatgtacc ccggcggtaa tgcattaaat tttgctgtct atgcgaaatt agcagacatc     120
cccagcgcgt ttatgggggc gtttggcaat gacgacgccg cgcagcacgt acaggatgta     180
ttacaccagc tacagataga catctctcac agccgccatt ataccggcga aaatgggtat     240
gcctgtatcc gtctctcgca tggcgatcgg caatttgtcg ccagcaacaa aaacggcgta     300
ttgcgggaac atccttttag tctgtctgac gacgatcttc gctatatatc acaatttacc     360
ttagtccatt ccagtattaa cggccacctg gaatcggaac tggagaaaat taaacaacaa     420
accgtcttac tctcttttga ttttttccggg cgcggtacag acgactattt tgaaaaggta     480
tgcccgtggg tagattacgg atttatctcc tgtagcgggt tatcgccaga tgaaatcaaa     540
gtaaaactca ataaacttta tcgttatggc tgtcggcata ttattgccac ctgcgggcat     600
gaaaaagttt attatttttc cggcgcggat tatctggagt ggcaacctgc ttatatcgaa     660
cctgtcgata cgctgggcgc aggcgacgcc ttcttaaccg ttttttgct ttccattttg     720 caatcgggta tggcggaacc cgataaagaa agcgtgttac gcgccatgcg gcagggcggg     780
aaatcggcgg cgcaggtgtt atctcattac ggcgcatttg gttttggtaa accgtttgca     840
caatag                                                                846

<210> SEQ ID NO 7
<211> LENGTH: 281
<212> TYPE: PRT
<213> ORGANISM: Salmonella enterica

<400> SEQUENCE: 7

Met Ser Ile Ser Val Leu Gly Ile Gly Asp Asn Val Val Asp Lys Tyr
1               5                   10                  15

Leu His Ser Gly Ile Met Tyr Pro Gly Gly Asn Ala Leu Asn Phe Ala
            20                  25                  30

| | | | | | | | | | | | |
|---|---|---|---|---|---|---|---|---|---|---|---|
|Val|Tyr|Ala|Lys|Leu|Ala|Asp|Ile|Pro|Ser|Ala|Phe|Met|Gly|Ala|Phe|
| | |35| | | |40| | | |45| |

Gly Asn Asp Asp Ala Ala Gln His Val Gln Asp Val Leu His Gln Leu
        50                  55                  60

Gln Ile Asp Ile Ser His Ser Arg His Tyr Thr Gly Glu Asn Gly Tyr
65                  70                  75                  80

Ala Cys Ile Arg Leu Ser His Gly Asp Arg Gln Phe Val Ala Ser Asn
                85                  90                  95

Lys Asn Gly Val Leu Arg Glu His Pro Phe Ser Leu Ser Asp Asp Asp
            100                 105                 110

Leu Arg Tyr Ile Ser Gln Phe Thr Leu Val His Ser Ser Ile Asn Gly
        115                 120                 125

His Leu Glu Ser Glu Leu Glu Lys Ile Lys Gln Gln Thr Val Leu Leu
    130                 135                 140

Ser Phe Asp Phe Ser Gly Arg Gly Thr Asp Asp Tyr Phe Glu Lys Val
145                 150                 155                 160

Cys Pro Trp Val Asp Tyr Gly Phe Ile Ser Cys Ser Gly Leu Ser Pro
                165                 170                 175

Asp Glu Ile Lys Val Lys Leu Asn Lys Leu Tyr Arg Tyr Gly Cys Arg
            180                 185                 190

His Ile Ile Ala Thr Cys Gly His Glu Lys Val Tyr Tyr Phe Ser Gly
        195                 200                 205

Ala Asp Tyr Leu Glu Trp Gln Pro Ala Tyr Ile Glu Pro Val Asp Thr
    210                 215                 220

Leu Gly Ala Gly Asp Ala Phe Leu Thr Gly Phe Leu Leu Ser Ile Leu
225                 230                 235                 240

Gln Ser Gly Met Ala Glu Pro Asp Lys Glu Ser Val Leu Arg Ala Met
                245                 250                 255

Arg Gln Gly Gly Lys Ser Ala Ala Gln Val Leu Ser His Tyr Gly Ala
            260                 265                 270

Phe Gly Phe Gly Lys Pro Phe Ala Gln
        275                 280

<210> SEQ ID NO 8
<211> LENGTH: 1044
<212> TYPE: DNA
<213> ORGANISM: Salmonella enterica

<400> SEQUENCE: 8

```
atgaaaatta gagttttcat ggccaccgtg ttgctgctca tcagccactg tgtatttagc      60
acaacgtcac taccgcatat tgttattctc gcgacaggtg gtactatcgc cgggacggca     120
gccaataata cgcaaaccgc cggatataaa tctggtgaac ttggcgtgca aacattaata     180
aatgccgtgc cggaaatgaa taatatcgct cgcgttgacg gcgagcaggt ggcgaatatt     240
ggtagcgaaa atatgaccag cgatatcatc ctgaaacttt cacagaaggt gaatgcgtta     300
ttggcgcggg acgatgttga cggtgtggtt attactcatg gcactgacac gctcgatgaa     360
accgcctact ttcttaattt gaccgtgaaa agcgacaaac cggtggtgtt taccgctgca     420
atgcggcccg cgtcggcaat cagcgccgat ggcgcaatga acctgctgga agcggtcacg     480
gtggctgctg acccgaatgc gaagggacgc ggtgtgatgg tggttttaaa cgatcgtatt     540
ggttcggcgc gctttgtgac gaaaactaat gccacgactc tggataccgt taaagcgccg     600
gaagagggct atctggggt catcgttaat ggtcagccac agttcgaaac gcgggtggaa     660
aaaattcata ccctgcgatc tgttttttgac gtacgtaata tcaaaaaatt acccaatgtg     720
```

-continued

```
gtgattattt acggctatca ggacgacccg aatatatgt atgatgcggc gatcgcccat    780
cacgcggacg gtattattta tgccggaacc ggcgcaggtt cggtctcggt acgcagcgac    840
gcggggatta aaaagcgga gaaagccggg attatcgtgg tgcgcgcttc ccgcaccgga    900
aacggcgtcg taccgttgga taagggcag ccagggctgg tgtctgactc gctcaacccg    960
gcgaaggcgc gagtcttgct gatgacggca ttaactcaga cgcgtaatcc ggaactgatc   1020
cagagttatt tcagtacgta ttaa                                         1044
```

<210> SEQ ID NO 9
<211> LENGTH: 347
<212> TYPE: PRT
<213> ORGANISM: Salmonella enterica

<400> SEQUENCE: 9

```
Met Lys Ile Arg Val Phe Met Ala Thr Val Leu Leu Ile Ser His
1               5                   10                  15

Cys Val Phe Ser Thr Thr Ser Leu Pro His Ile Val Ile Leu Ala Thr
            20                  25                  30

Gly Gly Thr Ile Ala Gly Thr Ala Ala Asn Asn Thr Gln Thr Ala Gly
        35                  40                  45

Tyr Lys Ser Gly Glu Leu Gly Val Gln Thr Leu Ile Asn Ala Val Pro
    50                  55                  60

Glu Met Asn Asn Ile Ala Arg Val Asp Gly Glu Gln Val Ala Asn Ile
65                  70                  75                  80

Gly Ser Glu Asn Met Thr Ser Asp Ile Ile Leu Lys Leu Ser Gln Lys
                85                  90                  95

Val Asn Ala Leu Leu Ala Arg Asp Asp Val Asp Gly Val Val Ile Thr
            100                 105                 110

His Gly Thr Asp Thr Leu Asp Glu Thr Ala Tyr Phe Leu Asn Leu Thr
        115                 120                 125

Val Lys Ser Asp Lys Pro Val Val Phe Thr Ala Ala Met Arg Pro Ala
    130                 135                 140

Ser Ala Ile Ser Ala Asp Gly Ala Met Asn Leu Leu Glu Ala Val Thr
145                 150                 155                 160

Val Ala Ala Asp Pro Asn Ala Lys Gly Arg Gly Val Met Val Val Leu
                165                 170                 175

Asn Asp Arg Ile Gly Ser Ala Arg Phe Val Thr Lys Thr Asn Ala Thr
            180                 185                 190

Thr Leu Asp Thr Phe Lys Ala Pro Glu Glu Gly Tyr Leu Gly Val Ile
        195                 200                 205

Val Asn Gly Gln Pro Gln Phe Glu Thr Arg Val Glu Lys Ile His Thr
    210                 215                 220

Leu Arg Ser Val Phe Asp Val Arg Asn Ile Lys Lys Leu Pro Asn Val
225                 230                 235                 240

Val Ile Ile Tyr Gly Tyr Gln Asp Asp Pro Glu Tyr Met Tyr Asp Ala
                245                 250                 255

Ala Ile Ala His His Ala Asp Gly Ile Ile Tyr Ala Gly Thr Gly Ala
            260                 265                 270

Gly Ser Val Ser Val Arg Ser Asp Ala Gly Ile Lys Lys Ala Glu Lys
        275                 280                 285

Ala Gly Ile Ile Val Val Arg Ala Ser Arg Thr Gly Asn Gly Val Val
    290                 295                 300

Pro Leu Asp Lys Gly Gln Pro Gly Leu Val Ser Asp Ser Leu Asn Pro
305                 310                 315                 320
```

```
Ala Lys Ala Arg Val Leu Leu Met Thr Ala Leu Thr Gln Thr Arg Asn
            325                 330                 335

Pro Glu Leu Ile Gln Ser Tyr Phe Ser Thr Tyr
        340                 345
```

<210> SEQ ID NO 10
<211> LENGTH: 661
<212> TYPE: DNA
<213> ORGANISM: Salmonella enterica

<400> SEQUENCE: 10

```
atgatcgagc aacccgacag taaaagcgcc aaaccgcttt ataagcagct tgaagccgcc    60
ttaaaagagg ctattgcgcg tggagagtat aaaccaggcc agcagatccc gacggaaaat   120
gaactgagcg tgcgctggca ggtgagcagg gtcacggtcc gtaaggcgct ggatgcgctg   180
acgcgtgaaa atttgctgac ccgtgtctcc ggcaaaggca cctttgtctc tggtgagaaa   240
tttcagcgca gcatgaccgg catcatgagt ttcagcgagt tatgccagtc ccagggacgt   300
cgcccggggt cacgcaccat caaatccgtt tttgaatcgg tagacgatga gacaaaagcg   360
ttactgaata tgaacgatgg cgaaaaagcg gtcgtcattg aacgtatccg ctatgccgac   420
gatgtggcgg tatcgctgga aaccgtacat cttcccccac gttttgcgtt tttgctggac   480
gaagatctta ataatcactc tttgtatgaa tgcttacgcg agaaatacca tttatggttt   540
acccactccc gtaagatgat cgaactggtt tatgccagct tgaagtcgc ccattatctt    600
ggcgtcaacg agggttatcc gctgatcctg ataaaaagtg aaatgattga taacaaagga   660
g                                                                   661
```

<210> SEQ ID NO 11
<211> LENGTH: 239
<212> TYPE: PRT
<213> ORGANISM: Salmonella enterica

<400> SEQUENCE: 11

```
Met Ile Glu Gln Pro Asp Ser Lys Ser Ala Lys Pro Leu Tyr Lys Gln
1               5                   10                  15

Leu Glu Ala Ala Leu Lys Glu Ala Ile Ala Arg Gly Glu Tyr Lys Pro
            20                  25                  30

Gly Gln Gln Ile Pro Thr Glu Asn Glu Leu Ser Val Arg Trp Gln Val
        35                  40                  45

Ser Arg Val Thr Val Arg Lys Ala Leu Asp Ala Leu Thr Arg Glu Asn
    50                  55                  60

Leu Leu Thr Arg Val Ser Gly Lys Gly Thr Phe Val Ser Gly Glu Lys
65                  70                  75                  80

Phe Gln Arg Ser Met Thr Gly Ile Met Ser Phe Ser Glu Leu Cys Gln
                85                  90                  95

Ser Gln Gly Arg Arg Pro Gly Ser Arg Thr Ile Lys Ser Val Phe Glu
            100                 105                 110

Ser Val Asp Asp Glu Thr Lys Ala Leu Leu Asn Met Asn Asp Gly Glu
        115                 120                 125

Lys Ala Val Val Ile Glu Arg Ile Arg Tyr Ala Asp Asp Val Ala Val
    130                 135                 140

Ser Leu Glu Thr Val His Leu Pro Pro Arg Phe Ala Phe Leu Leu Asp
145                 150                 155                 160

Glu Asp Leu Asn Asn His Ser Leu Tyr Glu Cys Leu Arg Glu Lys Tyr
                165                 170                 175
```

His Leu Trp Phe Thr His Ser Arg Lys Met Ile Glu Leu Val Tyr Ala
            180                 185                 190

Ser Phe Glu Val Ala His Tyr Leu Gly Val Asn Glu Gly Tyr Pro Leu
        195                 200                 205

Ile Leu Ile Lys Ser Glu Met Ile Asp Asn Lys Gly Glu Leu Ser Cys
    210                 215                 220

Val Ser Gln Gln Leu Ile Val Gly Asp Lys Ile Arg Phe Thr Val
225                 230                 235

<210> SEQ ID NO 12
<211> LENGTH: 51
<212> TYPE: DNA
<213> ORGANISM: Artificial Sequence
<220> FEATURE:
<223> OTHER INFORMATION: forward primer, fraD lambda red mutagenesis

<400> SEQUENCE: 12
attgtaaaga caaacaagga ataatgatga tgtgtaggct ggagctgctt c            51

<210> SEQ ID NO 13
<211> LENGTH: 49
<212> TYPE: DNA
<213> ORGANISM: Artificial Sequence
<220> FEATURE:
<223> OTHER INFORMATION: reverse primer, fraD/fraBD lambda red
      mutagenesis

<400> SEQUENCE: 13
tacattgagg gacgtaacct attgtgcaaa catatgaata tcctccttag              49

<210> SEQ ID NO 14
<211> LENGTH: 60
<212> TYPE: DNA
<213> ORGANISM: Artificial Sequence
<220> FEATURE:
<223> OTHER INFORMATION: forward primer, fraA lambda red mutagenesis

<400> SEQUENCE: 14
aggaggaagt atgttttgga cggaattatg ttttatcctt gtgtaggctg gagctgcttc   60

<210> SEQ ID NO 15
<211> LENGTH: 60
<212> TYPE: DNA
<213> ORGANISM: Artificial Sequence
<220> FEATURE:
<223> OTHER INFORMATION: reverse prime, fraA/fraBDA lambda red
      mutagenesis

<400> SEQUENCE: 15
tgaataacaa tcaggccaga accatttttc ctattaacag catatgaata tcctccttag   60

<210> SEQ ID NO 16
<211> LENGTH: 50
<212> TYPE: DNA
<213> ORGANISM: Artificial Sequence
<220> FEATURE:
<223> OTHER INFORMATION: reverse primer, fra island lambda red
      mutagenesis

<400> SEQUENCE: 16
gcgcacaagc ctgcatgatt aatacgtact catatgaata tcctccttag              50

```
<210> SEQ ID NO 17
<211> LENGTH: 60
<212> TYPE: DNA
<213> ORGANISM: Artificial Sequence
<220> FEATURE:
<223> OTHER INFORMATION: reverse primer, fraE lambda red mutagenesis

<400> SEQUENCE: 17
gcctgcatga ttaatacgta ctgaaataac tctggatcag catatgaata tcctccttag    60

<210> SEQ ID NO 18
<211> LENGTH: 60
<212> TYPE: DNA
<213> ORGANISM: Artificial Sequence
<220> FEATURE:
<223> OTHER INFORMATION: forward primer, fraE lambda red mutagenesis

<400> SEQUENCE: 18
gaggaagaaa atgaaaatta gagttttcat ggccaccgtg gtgtaggctg gagctgcttc    60

<210> SEQ ID NO 19
<211> LENGTH: 60
<212> TYPE: DNA
<213> ORGANISM: Artificial Sequence
<220> FEATURE:
<223> OTHER INFORMATION: forward primer, fraR/fra island lambda red
      mutagenesis

<400> SEQUENCE: 19
atggatacaa atgatcgagc aacccgacag taaaagcgcc gtgtaggctg gagctgcttc    60

<210> SEQ ID NO 20
<211> LENGTH: 60
<212> TYPE: DNA
<213> ORGANISM: Artificial Sequence
<220> FEATURE:
<223> OTHER INFORMATION: reverse primer, fraR lambda red mutagenesis

<400> SEQUENCE: 20
aatgctgaca tcatacggta aaccgtattt tatcgccgac catatgaata tcctccttag    60

<210> SEQ ID NO 21
<211> LENGTH: 60
<212> TYPE: DNA
<213> ORGANISM: Artificial Sequence
<220> FEATURE:
<223> OTHER INFORMATION: forward primer, fraB lambda red mutagenesis

<400> SEQUENCE: 21
cctgatgtaa ttaatattcc actttccaca tatagcggcg catatgaata tcctccttag    60

<210> SEQ ID NO 22
<211> LENGTH: 60
<212> TYPE: DNA
<213> ORGANISM: Artificial Sequence
<220> FEATURE:
<223> OTHER INFORMATION: reverse primer, fraB, fraBDA, and fraBD lambda
      red mutagenesis

<400> SEQUENCE: 22
agaggaaagc atgatgggta tgaaagagac agttagcaat gtgtaggctg gagctgcttc    60

<210> SEQ ID NO 23
<211> LENGTH: 61
<212> TYPE: DNA
<213> ORGANISM: Artificial Sequence
```

```
<220> FEATURE:
<223> OTHER INFORMATION: Primer placing cat gene (camr) downstream of
      pagC

<400> SEQUENCE: 23
cttctttacc agtgacacgt acctgcctgt cttttctctt gtgtaggctg gagctgcttc    60
g                                                                    61

<210> SEQ ID NO 24
<211> LENGTH: 58
<212> TYPE: DNA
<213> ORGANISM: Artificial Sequence
<220> FEATURE:
<223> OTHER INFORMATION: Primer placing cat gene (camr) downstream of
      pagC

<400> SEQUENCE: 24
cgaaggcggt cacaaaatct tgatgacatt gtgattaaca tatgaatatc ctccttag     58

<210> SEQ ID NO 25
<211> LENGTH: 28
<212> TYPE: DNA
<213> ORGANISM: Artificial Sequence
<220> FEATURE:
<223> OTHER INFORMATION: Primer amplifyies fra island for insertion into
      vector

<400> SEQUENCE: 25
cgcagaatct atccgtccga caacgaac                                      28

<210> SEQ ID NO 26
<211> LENGTH: 30
<212> TYPE: DNA
<213> ORGANISM: Artificial Sequence
<220> FEATURE:
<223> OTHER INFORMATION: Primer amplies fra island for cloning into
      vector

<400> SEQUENCE: 26
gcaggttaag gctctccgta aaggccaatc                                    30

<210> SEQ ID NO 27
<211> LENGTH: 60
<212> TYPE: DNA
<213> ORGANISM: Artificial Sequence
<220> FEATURE:
<223> OTHER INFORMATION: Primer for placing aph gene (kanr) within fraB

<400> SEQUENCE: 27
cctgatgtaa ttaatattcc actttccaca tatagcggcg catatgaata tcctccttag    60

<210> SEQ ID NO 28
<211> LENGTH: 60
<212> TYPE: DNA
<213> ORGANISM: Artificial Sequence
<220> FEATURE:
<223> OTHER INFORMATION: Primer for placing aph gene (kanr) within fraB

<400> SEQUENCE: 28
agaggaaagc atgatgggta tgaaagagac agttagcaat gtgtaggctg gagctgcttc    60
```

METHODS FOR THE IDENTIFICATION, CHARACTERIZATION, AND USE OF INHIBITORS OF THE FRUCTOSE-ASPARAGINE UTILIZATION PATHWAY

RELATED APPLICATIONS

This Application is a Nation Stage Application of International Application PCT/US2016/039645, filed Jun. 27, 2016, which claims the priority benefit of U.S. Provisional Applications No. 62/185,538, filed Jun. 26, 2015, and No. 62/207,881, filed Aug. 20, 2015, each of which is incorporated fully herein by reference for all purposes.

GOVERNMENT LICENSE RIGHTS

This invention was made with government support under Grants No. AI073971, No. AI097116, and No. 1R01AI116119, awarded by the National Institutes of Health. The government has certain rights in the invention.

SEQUENCE LISTING

The instant application contains a Sequence Listing which has been submitted in computer-readable ASCII format via EFS-Web and is incorporated in its entirety into this Application by reference.

FIELD

The embodiments described herein relate to microbiology, microbial selection, microbial diagnostics, and inhibition of microbial growth. The embodiments provide for selective growth media for investigating, isolating, counting, and directly identifying Salmonella; and for identifying and using small molecules that target specific metabolic pathways of Salmonella.

BACKGROUND

Bacteria of the genus Salmonella are pathogens of significant concern in worldwide health. Salmonella species are among the most significant food-borne pathogens affecting both agriculture and humans, causing morbidity and mortality across the globe. In humans, the elderly, infants, and those with impaired immune systems are more likely to develop severe salmonellosis. In severe cases, the Salmonella infection may spread from the intestines to the blood stream and then to other body sites, and such infection often proves fatal if not treated with the appropriate antibiotics. Indeed, Salmonella is the leading cause of death from food-borne illness in the United States. Although in the United States most cases of salmonellosis are self-limiting, some people afflicted with salmonellosis later experience reactive arthritis, which can have long-lasting, disabling effects. Another form of Salmonella disease, called invasive non-typhoidal salmonellosis (iNTS), is emerging, especially in Africa where the disease is associated with malaria infection in children and HIV infection in adults. Typhimurium and Enteritidis serovars are the most medically significant serovars in the United States, and the most common serovars associated with iNTS.

In addition, Salmonella serovars have been implicated in a spectrum of other diseases, including enteric or typhoid fever (primarily from S. typhi and S. paratyphi), bacteremia, endovascular infections, focal infections (e.g., osteomyelitis), and enterocolitis (typically from S. typhimurium, S. enteritidis, and S. heidelberg). Currently, there are no human vaccines for the non-typhoidal Salmonella serovars. Antibiotics are not recommended for uncomplicated cases of Salmonella-mediated gastroenteritis, but are used to treat the very young or elderly, or when there are complications or invasive disease. Multiple drug resistance is prevalent and increasing, however, hence novel therapeutic approaches are needed for preventing or treating non-typhoidal salmonellosis.

The species S. enterica contains over 99% of the serovars that are capable of infecting cold and warm blooded animals, as well as humans. Indeed, more than 2500 serovars of S. enterica have been identified. S. enterica subspecies enterica includes typhoidal serovars that cause typhoid fever, and non-typhoidal serovars that cause gastroenteritis. These serovars can infect a remarkably broad range of host species, infecting a large number of different animals and even plants. In humans, S. enterica infection is usually contracted after eating, for example, contaminated or infected eggs, egg products, or milk that was not prepared, handled, or refrigerated properly; meat if it was prepared incorrectly or was contaminated with Salmonella after preparation; or contaminated fruits or vegetables. The Centers for Disease and Control and Prevention estimates that in the United States alone there are about 1.4 million cases per year of non-typhoidal salmonellosis. Because Salmonella-tainted foods often have no unusual look or smell, it is imperative that food sources can be tested efficiently for the presence of Salmonella. Moreover, accurate diagnosis of Salmonella infection that allows for treatment options, i.e., antibiotic therapy, is an important healthcare goal.

SUMMARY

The embodiments described herein provide for compositions and methods useful in the identification and inhibition of Salmonella. In particular, Salmonella can grow with fructose-asparagine (F-Asn) as sole nutrient source. Salmonella carries the genes for F-Asn utilization, located, for example, between the gor and treF genes at 77.7 centisomes of the Salmonella 14028 genome (ORFs STM14_4328 to STM14_4332). These genes as described herein are designated fra, and specifically fraB, fraD, fraA, fraE, and fraR. The expression of these genes may be regulated by a promoter region designated fra promoter and by an inverted repeat sequence and small RNA encoded near the 5' end of fraD. Deletion of the fraB, fraD, fraA, fraE, and fraR genes eliminates the ability of Salmonella to grow on F-Asn. The fra locus is not present in E. coli, and other organisms are not able use this nutrient as a sole source. Phylogenetic analysis suggests that the Salmonella serovars that cause gastroenteritis are likely to use F-Asn. The ability of Salmonella to grow on F-Asn in growth medium provides a novel diagnostic marker to identify Salmonella. Minimal media including F-Asn as a nutrient source provides a highly selective and inexpensive composition for the enrichment, identification, and isolation of Salmonella.

Accordingly, in at least one aspect, the present embodiments provide for a Salmonella-selective bacterial growth media comprising F-Asn. Surprisingly, Salmonella can grow in a medium in which F-Asn is the sole nutrient source, while non-Salmonella bacteria are substantially eliminated in this medium. This is a novel ability among bacteria and provides a way to distinguish Salmonella from other bacteria. F-Asn-based minimal medium is more selective and may be substantially less expensive than current commercially available media. F-Asn utilization is specific to *Salmonella*, making it highly diagnostic. In some embodiments, a F-Asn medium is used to identify *Salmonella*. In some embodiments, F-Asn is the sole nutrient in a minimal medium, such as M9 medium. In some embodiments, F-Asn is a nutrient added to a minimal media comprising thiosulfate and iodine. In some embodiments, F-Asn is a nutrient added to a minimal media comprising tetrathionate. In some embodiments, F-Asn is a nutrient added to a rich media comprising tetrathionate and additional iodine. For example, F-Asn can be added to tetrathionate broth.

At least one embodiment provides a minimal medium comprising F-Asn as a sole nutrient source. At least one embodiment provides a minimal medium comprising F-Asn, thiosulfate, and iodine. At least one embodiment provides a minimal medium comprising F-Asn, tetrathionate, and iodine. At least one embodiment provides a minimal medium comprising F-Asn and tetrathionate. At least one embodiment provides a rich medium comprising F-Asn and tetrathionate or thiosulfate and iodine. Related embodiments provide for F-Asn-containing media that also includes other features, e.g., compounds or dyes as are known in the art that can be combined in F-Asn-containing medium to further identify, select, or enrich for *Salmonella*, or distinguish *Salmonella* from other microbes in a mixed population. For example, F-Asn can be added to MacConkey agar to make this a more selective medium.

A related aspect provides methods of identifying *Salmonella*, comprising inoculating a suspected *Salmonella* isolate into or onto a bacterial growth minimal medium comprising F-Asn as a nutrient source and incubating the medium. In particular embodiments, F-Asn is the sole nutrient source in the minimal medium. In particular embodiments, F-Asn is the sole carbon source in the medium. In particular embodiments, F-Asn is the sole nitrogen source in the minimal medium. In other embodiments, F-Asn is combined with other nutrient sources useful for distinguishing or selecting *Salmonella* or another bacterium or bacteria.

At least one embodiment provides a method of identifying whether a sample contains *Salmonella*, comprising placing a sample into or onto a bacterial growth minimal media comprising F-Asn as a nutrient source (or such minimal media in which F-Asn is the sole carbon, nitrogen, or nutrient source). For example, the sample can be a clinical sample such as a stool sample, a biological sample, a foodstuffs sample, or an environmental sample. The *Salmonella* may be *S. enterica*.

In some embodiments, F-Asn is used as a nutrient source in a minimal enrichment broth, or as a nutrient source in a solid medium (e.g., agar plates or stabs) as positive selection for *Salmonella*. In some embodiments, the media (e.g., minimal enrichment broth) is used to selectively expand a population of *Salmonella*. In some embodiments, F-Asn is the sole nutrient source in the medium. In some embodiments, F-Asn is the sole carbon source in the medium. In some embodiments, F-Asn is the sole nitrogen source in the medium. In particular embodiments, the *Salmonella* is *Salmonella enterica*. Increasing the expression of the F-Asn utilization locus and its corresponding proteins provides efficient access to additional potential therapeutic targets.

Another embodiment provides a method of distinguishing typhoidal serovars of *Salmonella* from non-typhoidal serovars, comprising inoculating a suspected *Salmonella* isolate into or onto a bacterial growth media comprising F-Asn as a nutrient source, wherein the non-typhoidal serovars grows in the medium, but the typhoidal serovars may not grow in the medium. In particular embodiments, F-Asn is the sole nutrient source in the medium.

A related aspect of the present embodiments provides diagnostic kits that include a *Salmonella*-selective medium as described herein. For example, the kit can include at least one unit of the *Salmonella*-selective growth medium in liquid (e.g., tube or vial) or solid form (e.g., agar slab or plate). A *Salmonella*-selective growth medium may also contain, in addition to F-Asn, other components useful for identifying *Salmonella* or other microbes. The kit may further include other media units useful in identifying *Salmonella* or other microbes.

Another aspect of the present embodiments provides a method for identifying the presence of F-Asn utilization genes as an approach to identifying or diagnosing *Salmonella*. For example, the fra genes are not present in *E. coli*—another bacterium with pathogenic potential. The fra gene identified by this method may be at least one of the fraB, fraD, fraA, fraE, or fraR genes, or the fra promoter. The genetic assay may identify a fra gene via its DNA (e.g., fraR or any one of fraBDAE) or mRNA (e.g., mRNA from any one of fraBDAE). In particular, the genetic assay may use a primer or probe comprising at least ten contiguous nucleotides selected from the fra genetic elements having the nucleotide sequence as shown in SEQ ID NO:1, SEQ ID NO:2, SEQ ID NO:4, SEQ ID NO: 6, SEQ ID NO:8, or SEQ ID NO:10, or complements thereof, or a nucleotide sequence with sufficient homology to provide complementary binding to the fra genetic element. Additionally, the genetic assay may use a primer or probe having at least ten contiguous nucleotides selected from the molecule having the nucleotide sequence of SEQ ID NO:12 to SEQ ID NO:28, or complements thereof, or a nucleotide sequence with sufficient homology to provide complementary binding to the fra genetic element. The genetic screening identification can be qualitative or quantitative.

Another aspect of the present embodiments provides a method for identifying the presence of F-Asn utilization proteins, such as at least one of FraB, FraD, FraE, FraA, or FraR in a sample, for example by immunoassay (e.g., and antibody test). For example, an expression cassette as described herein provides a recombinant F-Asn utilization protein that can be used, for example, to generate an antibody (or antibodies) or as a positive control in an immunoassay. For example, an antigen binding molecule useful in an immunoassay method may be an antibody or a portion of an antibody generated against an antigenic portion of a protein having an amino acid sequence of SEQ ID NO:3, SEQ ID NO:5, SEQ ID NO:7, SEQ ID NO:9, or SEQ ID NO:11. The immunoassay can be qualitative or quantitative.

Yet another aspect of the present embodiments provides a recombinant gene cassette. The recombinant gene cassette can include at least one of the fra promoter, fraB, fraD, fraA, fraE, or fraR genes, or ORFs STM14_4328 to STM14_4332 of the *Salmonella* strain 14028 genome. The recombinant gene cassette can further include a marker. The recombinant gene cassette can further include regulatory elements, such as regulatory elements heterologous to the fra open reading frame(s). The recombinant gene cassette can be an expression cassette in which at least one of the fra genes is expressed as a protein. The recombinant gene cassette can be part of a genetic vector such as a plasmid. The recombinant gene cassette can be part of a recombinant microbial genome, including a heterologous genome. The recombinant gene cassette can be part of a recombinant bacterium or other microbe that may be within a different or the same genus or species of bacterium but otherwise does not include functional fra genes in its native state. In particular, the recombinant gene cassette can be used to generate probes, proteins, or other aspects useful in identifying or diagnosing *Salmonella*. Proteins produced in a recombinant host can be isolated or purified by any number of techniques known in the art.

A related embodiment provides a recombinant vector constructed such that a heterologous gene (i.e., a gene that is not a *Salmonella enterica Typhimurium* fra gene) is placed under control of the fra promoter. The fra promoter is induced by placing the recombinant host in a media comprising F-Asn as a nutrient (an inducible promoter). Heterologous proteins that may be expressed via the fra-inducible promoter include hormones, enzymes, growth factors, cytokines, antigens, immunogens, antibodies, fusion proteins, or other biologics.

Another aspect of the present embodiments provides methods and compositions that inhibit *Salmonella* by targeting the F-Asn utilization pathway, i.e., at least one fra gene(s) or its gene product(s), such as the fraB gene and its product FraB. For example, high throughput screening allows identification of small molecules that target FraB. In particular, inhibition of *Salmonella* fraB results in toxic accumulation of 6-P—F-Asp; accordingly, fraB (e.g., FraB) provides at least one drug target, a prospect strengthened by the absence of the fra island in most of the gut microbiota. Accordingly, a particular embodiment provides for FraB as a drug target. In a particular embodiment, the activity of FraB is antagonized, causing toxic accumulation of F-Asn or 6-P—F-Asp in the affected *Salmonella* cell. In a particular embodiment, the expression of fraB is inhibited, causing toxic accumulation of F-Asn or 6-P—F-Asp in the affected *Salmonella* cell.

Accordingly, at least one embodiment provides a method of selecting an agent that inhibits the growth of *Salmonella enterica Typhimurium* comprising: evaluating whether the agent inhibits the expression of fraB or the function of FraB; and selecting the agent that inhibits the expression of fraB or the function of FraB. At least one embodiment provides a method of selecting an agent that inhibits the growth of *Salmonella enterica Typhimurium* comprising: evaluating whether the agent inhibits the expression of fraE or the function of FraE; and selecting the agent that inhibits the expression of fraE or the function of FraE. At least one embodiment provides a method of selecting an agent that inhibits the growth of *Salmonella enterica Typhimurium* comprising: evaluating whether the agent inhibits the expression of fraD or the function of FraD; and selecting the agent that inhibits the expression of fraD or the function of FraD. At least one embodiment provides a method of selecting an agent that inhibits the growth of *Salmonella enterica Typhimurium* comprising: evaluating whether the agent induces the expression of fraR or the function of FraR; and selecting the agent that induces the expression of fraR or the function of FraR. At least one embodiment provides a method of selecting an agent that inhibits the growth of *Salmonella enterica Typhimurium* comprising: evaluating whether the agent inhibits the function of fra promoter. Because an identified drug is specific for the F-Asn utilization pathway, which is present in *Salmonella* but only rarely present in other bacteria and no fraB homolog exists in mammals, an agent targeting the Fra pathway is a narrow-spectrum agent. Unlike broad-spectrum antibiotics that may disrupt the normal microbiota in the gut microbiome, targeting the Fra utilization pathway offers *Salmonella*-specific therapeutic agents that do not disrupt an otherwise healthy microbiome.

At least one embodiment provides a method of inhibiting the growth of *Salmonella enterica Typhimurium* in vitro comprising introducing at least one of purified or isolated enzymes FraE, FraD, or FraB in vitro. At least one embodiment provides a method of inhibiting the growth of *Salmonella enterica Typhimurium* in vivo comprising introducing or administering at least one of purified or isolated enzymes FraE, FraD, or FraB in vivo.

As disclosed herein, the apparent species-specificity of the F-Asn utilization system, and the severity of the fitness defect associated with mutants that cannot metabolize F-Asn, indicate that the Fra utilization pathway represents a specific and valuable therapeutic target for a therapeutic agent. The knowledge that *Salmonella* utilizes F-Asn further allows for additional characterization of other members of the normal microbiota (or microbiota in a diseased host) that may compete with *Salmonella* for F-Asn and other Amadori products (e.g., *E. coli* for F-Lys). Additionally, the embodiments described herein facilitate the determination of the role of each gene in the fra locus with regard to F-Asn metabolism. Similarly, embodiments described herein facilitate the determination of the mechanism by which the proposed transcription factor, FraR, regulates F-Asn metabolism. In at least one embodiment, the drug target is fraB/FraB. These structure-function studies further facilitate small molecule drug screens targeting F-Asn utilization.

Because of the implications to food sources as carriers of *Salmonella*, the present embodiments further allow comparison with the concentration of F-Asn and other Amadori products in a wide variety of food sources to determine if Amadori products can affect disease susceptibility, and provide the possibility of preventing *salmonellosis* or other infections by removing Amadori products from specific food products or from the diet in general. The present embodiments also provide a model for the discovery of other utilization systems: additional Amadori products are likely awaiting discovery, and these may play important roles in microbial ecology and human health.

DESCRIPTION OF THE DRAWINGS

FIG. 2E is a graph showing complementation of a fraB1::kan mutation with plasmid pASD5006 encoding the fra island (ASD6000) or the vector control, pWSK29 (ASD6010). Each point represents the mean of three cultures with error bars indicating standard deviation. FIG. 2A to FIG. 2C: ● wild-type; ○ fraB mutant; FIG. 2D: ● Glucose wild-type; ○ Glucose fraB mutant; □ No carbon source; ● Sterility; ◇ Asn wild-type; * Arg wild-type; × Lys wild type; FIG. 2E: ○ Glucose fraB mutant+pASD5006; ● Glucose fraB mutant+vector; ■ F-Asn fraB mutant+pASD5006; F-Asn fraB mutant+vector; y-axis: $OD_{600}$; x-axis: time (hours).

FIG. 4A to FIG. 4D show growth of *Salmonella* on F-Asn in the presence or absence of tetrathionate or oxygen. Growth of wild-type MA43 and fraB1::kan mutant MA59 on 5 mM F-Asn or 5 mM glucose anaerobically (FIG. 4A and FIG. 4B) or aerobically (FIG. 4C and FIG. 4D) in the presence (FIG. 4A and FIG. 4C) or absence (FIG. 4B and FIG. 4D) of 40 mM tetrathionate (S406 22). Bacteria were grown overnight in LB at 37° C. shaking, centrifuged, resuspended in water, and subcultured 1:1000 into NCE medium containing the indicated carbon source. The optical density at 600 nm was then read at time points during growth at 37° C. with shaking. Each point represents the mean of four cultures with error bars indicating standard deviation. ● F-Asn wild-type; ■ F-Asn fraB mutant; ▲ Glucose wild-type; ▼ Glucose fraB mutant; x-axis: time (hours); y-axis: $OD_{600}$.

FIG. 10A to FIG. 10D outline transposon site hybridization (TraSH) screening. Polymerase T7 is used to generate transcripts (FIG. 10A to FIG. 10C). FIG. 10D shows in vivo testing of fitness genes identified in the TraSH screening and further characterization using microarrays in which the negative spot in output indicates mutant gene "x". The Tn-seq approach is similar, but the T7 transcripts are sequenced instead of hybridized to microarrays for analysis.

FIG. 17 is a diagram of a G6PD-based coupled assay to measure *Salmonella* deglycase activity.

FIG. 18A to FIG. 18C illustrate the structure of the YurP protein from *Bacillus subtilis*, a FraB homolog. FIG. 18A shows the monomer consists of two a/b subdomains, each having a flavodoxin-like fold. FIG. 18B shows the putative active-site cleft, bound with citrate and glycerol, is located at the dimer interface. FIG. 18C show several likely catalytic residues.

FIG. 19 shows Crystals of FraB. Crystals were grown by hanging drop vapor diffusion from solutions of 20% PEG 3350, 0.2 M potassium sulfate, pH 6.8.

FIG. 24A and FIG. 24B present mass spectrometry (MS) data in which each point represents MS-based measurement of the levels of 6-P—F-Asp (y-axis: nmol) in one biological replicate. Samples were prepared by taking a one-fifteenth aliquot from the cell pellet of a 20-ml culture of *Salmonella* wild-type (14028), ΔfraB::kan (HMB206), or Δfra island deletion (HMB215) mutant. Two transitions were measured to confirm quantitation; data from one transition are shown in FIG. 24A and data from a second transition are shown in FIG. 24B. The values provided are the mean±standard deviation from three biological replicates. The lowest concentration on the standard curve was 20 nmol, so the values for wild-type and Δfra island deletion are very low, yet they indicate the reproducible absence of 6-P—F-Asp in these two strains.

FIG. 25 reflects the determination of the $IC_{50}$ and $IC_{90}$ of F-Asn to a fraB mutant. Wild-type (strain 14028, ●), ΔfraB::kan (HMB206, □) or Δfra island (HMB205, ▲) were grown in M9 minimal medium containing 5 mM glucose and varying concentrations of F-Asn. The data points represent the optical density obtained after 15 hours of growth at 37° C. (three biological replicates with three technical replicates in each (nine total replicates); error bars representing standard deviation. $IC_{50}$ and $IC_{90}$ were calculated and plotted plus/minus the 95% confidence intervals. The $IC_{50}$ is 19 μM (9 to 40 μM) and the $IC_{90}$ is 174 μM (82 to 368 μM).

DETAILED DESCRIPTION

Figure 1:
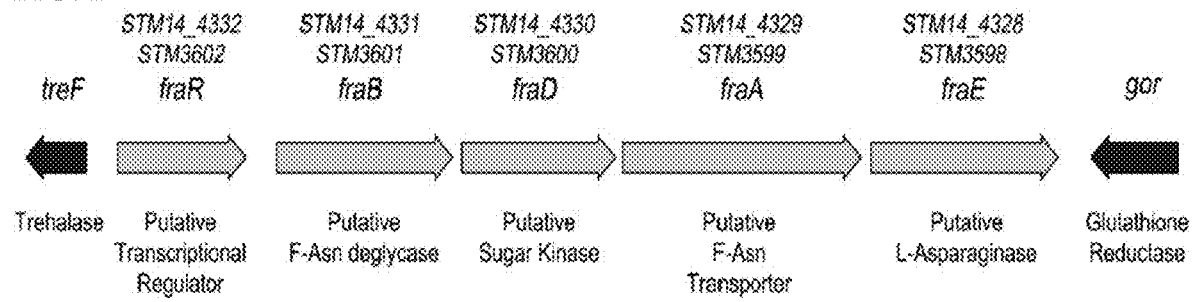
FIG. 1 is a map of the fra locus of *Salmonella enterica*. The five genes of the fra locus are shown as grey arrows. The gor and treF genes are shown as black arrows and are conserved throughout the Enterobacteriaceae, although the fra locus is not; suggesting horizontal acquisition of the fra locus. The proposed functions and names of each gene are shown below and above the arrows, respectively. The names are based upon the distantly related frl locus of *E. coli*. For example, the deglycase enzyme of the frl locus is encoded by frlB so the putative deglycase of the fra locus is named fraB. The fra locus has no frlC homolog, and the frl locus does not have an asparaginase. Therefore, the name fraC was not used, and the asparaginase-encoding gene was named fraE. The locus tags using the *Salmonella* nomenclature for strains 14028 (STM14 numbers) and LT2 (STM numbers) are shown above the gene names.

The details of one or more embodiments are set forth in the present description and figures. Other features, objects, and advantages of the embodiments will be apparent from the description and drawings, and from the claims. It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms "a," "an," and "the" include the plural reference unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." The term "about" when used in connection with percentages may mean±1%. Unless defined otherwise, all technical and scientific terms used herein have the same meaning as those commonly understood to one of ordinary skill in the art to which this invention pertains.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

There are many requirements for methods of screening for specific bacteria, particularly those present in low numbers and in specific environments; for example, human bacterial pathogens in contaminated foods. Public health and quality control organizations demand accurate, rapid bacterial detection methods having suitable specificity. The present embodiments enable a medium that provides accurate and rapid detection of *Salmonella*. Moreover, the present embodiments facilitate agents that specifically target *Salmonella* without compromising the normal microbiota.

*Salmonella* is a foodborne pathogen that causes significant morbidity and mortality in both developed and economically emerging countries. Gordon, 24 Curr. Op. Infect. Dis. 484 (2011); Chen et al., 54 Pediatrics Neonatol. 147 (2013). It was widely believed that there were no undiscovered drug targets in *Salmonella enterica*, largely due to the high number of nutrients available during infection and redundancy in metabolic pathways. Becker et al., 440 Nat. 303 (2006); Steeb et al., 9 PLoS Pathol. e1003301 (2013). To acquire nutrients in the intestine, *Salmonella* initiates inflammation, which disrupts the microbiota and causes an oxidative burst that leads to the formation of tetrathionate. Gordon, 2011; Chen et al., 2013; Becker et al., 2006; Stecher et al., 5 PLoS Biol. 2177 (2007); Winter et al., 467 Nat. 426 (2010); Serkirov et al., 1 Gut Microbes 30 (2010).

It was known that *Salmonella* uses tetrathionate as a terminal electron acceptor for the anaerobic respiration of carbon compounds that otherwise would not be metabolized. Thiennimitr et al., 108 PNAS 17480 (2011). One of these carbon sources is ethanolamine, which is derived from host phospholipids. Ethanolamine can be respired by *Salmonella*, but not fermented. Thiennimitr et al., 2011. *Salmonella* actively initiates inflammation using two Type 3 Secretion Systems (T3SS), each encoded within a distinct, horizontally acquired pathogenicity island. SPI1 (*Salmonella* Pathogenicity Island 1) contributes to invasion of host cells and elicitation of inflammation in the host. SPI2 (*Salmonella* Pathogenicity Island 2) is required for survival within macrophages and contributes to intestinal inflammation. *Salmonella* strains lacking SPI1 and SPI2 cause very little intestinal inflammation. Stecher et al., 2007; Winter et al., 2010; Thiennimitr et al., 2011; Hapfelmeier et al., 174 J. Immunol. 1675 (2005).

It had long been thought that the nutrient utilization systems of *Salmonella* would not make effective drug targets because there are simply too many nutrients available to *Salmonella* in the intestine. Surprisingly, the present embodiments reflect the discovery that *Salmonella* can rely on fructose asparagine (F-Asn) as a carbon source (FIG. 2A, FIG. 3), consumed by *Salmonella* in addition to tetrathionate respiration (see FIG. 4A, FIG. 4B) during the host inflammatory response, and indeed F-Asn can be used as the sole nutrient during growth in the inflamed intestine. A mutant of *Salmonella* that cannot obtain F-Asn or lacked the F-Asn utilization system was severely attenuated particular models, suggesting that F-Asn may be a nutrient used by *Salmonella* during inflammation in that model. No other organism has been reported to synthesize or utilize this biological compound.

As described herein, F-Asn is a compound that is used during *Salmonella*-mediated inflammation of the intestine. F-Asn is a glycosylamine (aminodeoxysugar), IUPAC name (2R)-4-amino-4-oxo-2-[[(3S,4R,5R)-2,3,4,5-tetrahydroxyoxan-2-yl]methylamino]butanoic acid, with the structure (CAS No. 34393-27-6):

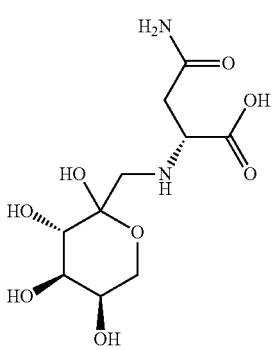 [SMILES: NC(=O)C[C@@H](NCC1(O)OC[C@@H](O)[C@@H](O)[C@@H]1O)C(=O)O]

F-Asn is an Amadori compound (also known as a glycation product), formed spontaneously (non-enzymatically) by a reaction between a glucose in its open chain form with the alpha amino group of asparagine, followed by a rearrangement that gives the fructose derivative.

Figure 16:
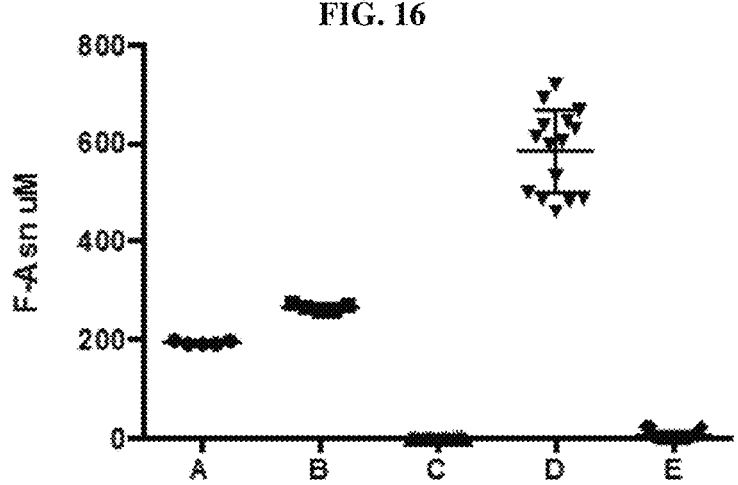
FIG. 16 shows the concentration of F-Asn in mouse chow and mouse cecum contents. Error bars represent ±SD. F-Asn was measured in mouse chow and mouse intestinal contents using liquid chromatography coupled with mass spectrometry (MS). A: autoclaved; B: irradiated mouse chow; C: cecum contents conventional mouse; D: cecum contents germ-free mouse; E: cecum content germ-free+*Salmonella*.

Until the embodiments described herein, no organism had been shown to synthesize or utilize F-Asn. It was discovered in the early 2000s that acrylamide is present in many fried foods, especially French fries and potato chips. After the acrylamide discovery, numerous papers measured acrylamide concentration; and the precursor molecules—glucose and asparagine—in foods. F-Asn was identified as a precursor to acrylamide. Vivanti et al., 71 J. Food Sci. C81 (2006); Stadler et al., 52 J. Agric. Food Chem. 5550 (2004); Surdyk et al., 52 J. Agric. Food Chem. 2047 (2004); Yaylayan et al., 51 J. Agric. Food Chem. 1753 (2003); Mottram et al., 419 Nat. 448 (2002); Tareke et al., 50 J. Agric. Food Chem. 4998 (2002); Tareke et al., 13 Chem. Res. Toxicol. 517 (2000); Elmore & Mottram, JIFSAN Acrylimide in Food Workshop (2002). The concentration of F-Asn in a few fruits and vegetables has been measured. Anet & Reynolds, 10 Aust. J. Chem. 182 (1957); Eichner et al., ACS Symp. Ser. 543 (Washington, D C, 1994). The concentrations are surprisingly high, ranging between 0.1% (carrot) and 1.4% dry weight (asparagus). Eichner et al., 1994. F-Asn is also present in commercial mouse chow (0.2 mM). See FIG. 16. Factors that influence these F-Asn concentrations are time, temperature, pressure, and perhaps less obviously, moisture content. Mossine & Mawhinney, 64 Adv. Carbohydr. Chem. Biochem. 291 (2010). Indeed, any reducing sugar and any amino acid (or other amines) can form compounds analogous to F-Asn.

It should be noted that these Amadori compounds, such as F-Asn, are not ultimate products because with further time and heating they decompose to a large variety of other products, some of which are responsible for a variety of flavors, and the brown color, in cooked foods. Mossine & Mawhinney, 2010; Mottram, in FLAVOURS & FRAGRANCES at 269 (Springer, Berlin, Heidelberg, Germany); Anet 10 Aust. J. Chem. 193 (1957). In fact, glycation products form spontaneously in the human body and provide an indication of glucose concentration over time. Tessier et al., 58 Pathol. Biol. 214 (2010); Bodiga et al., 19 Heart Fail. Rev. 49 (2013); Kato et al., 32 J. Gastronenterol. Hepatol. 5140 (2008); Brownlee, 46 Ann. Rev. Med. 223 (1995). A common diabetes test measures the glycation of the N-terminal valine of hemoglobin. Tessier et al., 2010.

F-Asn can be chemically synthesized or purified from certain natural sources that contain it in high concentration. For example, F-Asn can be synthesized by refluxing D-glucose with sodium bisulfite in methanol, then adding L-asparagine, and then adding acetic acid or malonic acid. See Example 1, herein. Additionally, as noted above F-Asn can be formed by way of the Maillard reaction when cooking food. Ion exchange resins or other appropriate techniques can separate the F-Asn product from other impurities. F-Asn is available from commercial sources (e.g., Abcam plc, Cambridge, Mass. Toronto Research Chemicals, Toronto, Canada). Before the present embodiments, F-Asn synthesis pathway had not been fully characterized in any organism.

The novelty of this nutrient and the apparent lack of F-Asn utilization systems in mammals and other bacteria suggest that the F-Asn utilization system represents not only a specific therapeutic target for *Salmonella*, but also a means for selecting, identifying, and diagnosing *Salmonella* by using novel compositions, i.e., F-Asn-based bacterial growth media. Minimal media are culture media that contain only the minimal necessities for growth; inorganic salts, a carbon source (e.g., glucose), and water. Many such media are available commercially or otherwise known in the art, and are adaptable for *Salmonella* growth with the inclusion of F-Asn. Selective media are used to allow growth of only particular microorganisms. Because *Salmonella* can grow with F-Asn as a nutrient source, the novel selective medium in which F-Asn is carbon or nitrogen source, or even the sole carbon or nitrogen source, provides a way to distinguish *Salmonella* from other bacteria. Selective growth media can also be used to ensure the survival or proliferation of target organisms with certain properties, the presence of a specific gene, locus, or an allele that confers upon the organism the ability to grow in the selective medium. In such cases, the gene is termed a marker. In the field of microbial diagnostics, F-Asn can serve as such a marker. F-Asn-based media can be used as an enrichment broth, or as a nutrient source in broth or agar plates as a selection for *Salmonella*. Currently, a commonly used enrichment broth for *Salmonella* is tetrathionate enrichment broth. This medium can be made more specific to *Salmonella* by removing many of its components and adding F-Asn, or by adding F-Asn to the tetrathionate enrichment broth. Additionally, minimal agar plates containing F-Asn can be used to directly select for *Salmonella*.

The name of the genetic locus that provides F-Asn utilization in *Salmonella* is designated fra (for fructose-asparagine utilization) (FIG. 1). Accordingly, the genes that enable *Salmonella* F-Asn utilization can be used as a genetic screen to identify *Salmonella*. This fra locus has a promoter and five genes: fraR (a regulator), fraB a fructose-asparagine deglycase, fraD a sugar kinase, fraA a fructose-asparagine transporter, and fraE a L-asparaginase. See FIG. 1, FIG. 6. Expression of fra may be further regulated by a promoter region, designated fra promoter, and by an inverted repeat sequence and small RNA encoded near the 5' end of fraD. These genes may also be designated herein as fraBDAE and fraR. Without being bound by theory, it appears that the fra locus represents a horizontal acquisition inserted between the gor and treF genes at centisome 77.7 of the *Salmonella* 14028 chromosome (ORFs STM14_4328 to STM14_4332). Deletion of the fra locus eliminates the ability to grow on F-Asn. There are other similar operons in *Salmonella*, and in other genomes, presumably for utilization of related glycation products.

Phylogenetic analysis suggests that only those serovars of *Salmonella* capable of causing gastroenteritis are likely to use F-Asn: *Salmonella* serovars that are capable of causing Typhoid fever do not appear to have the ability to use F-Asn. The ability of *Salmonella* to grow on F-Asn is a novel finding and indicates that the use of F-Asn in growth medium can be used as a diagnostic marker to identify *Salmonella*. The diagnosis of *Salmonella* can further inform treatment options for the infected patient. Additionally, the specificity of the fra genes in *Salmonella* offers a convenient and selective target for small molecules that either antagonize this pathway or otherwise inhibit *Salmonella*. This approach potentiates development of therapeutics for non-typhoidal *salmonellosis* and invasive non-typhoidal *salmonellosis*, such as a therapeutic agent or drug that could dramatically decrease the duration and severity of an acute *Salmonella* infection while leaving the remaining microbiota intact.

Figure 11A:
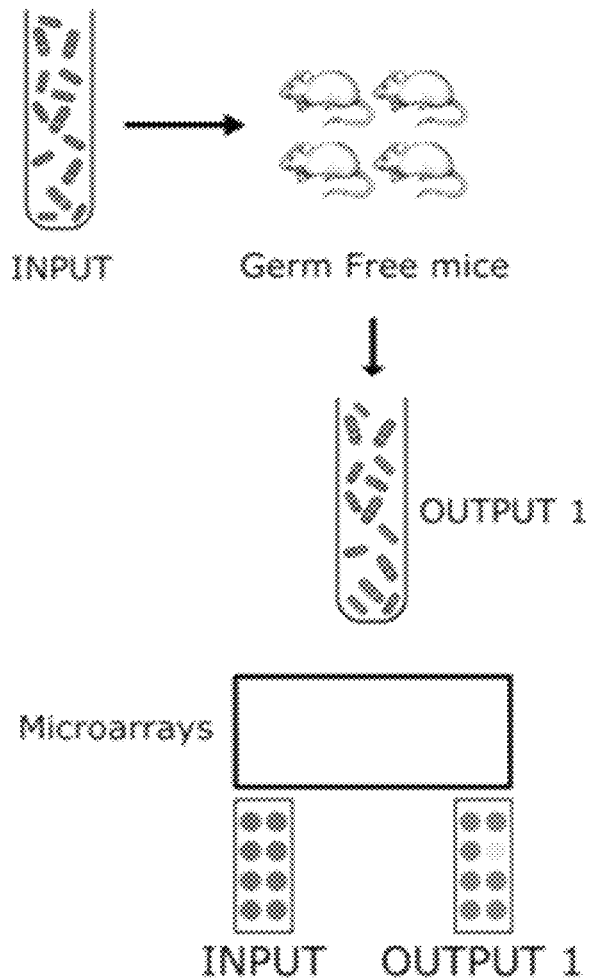
FIG. 11A and FIG. 11B compare in vivo experiments that use germ-free mice (FIG. 11A) with experiments that use germ-free mice colonized with *Enterobacter* (FIG. 11B). The microarrays with the negative spot in output 1 indicating mutant gene "x" in FIG. 11A, and the negative spot in output 2 indicating mutant gene "y" in FIG. 11B. As with FIG. 10, the location of the Tn insertion and what the mutant was selected against is correlated with microarray data in screening for fitness genes.

By way of context, the mechanisms by which microbes interact with each other in the gastrointestinal tract are largely unknown. It is known that quorum sensing is the regulation of gene expression in response to fluctuations in cell-population density. Quorum sensing bacteria produce, release, and respond to chemical signal molecules called autoinducers, which are analogous to pheromones, and may increase in concentration as a function of cell density. N-Acyl homoserine lactones (abbreviated as AHLs or N-AHLs) are a class of signaling molecules involved in bacterial quorum sensing. *Escherichia* and *Salmonella* encode SdiA, a transcription factor of the LuxR family that regulates genes in response to AHLs produced by other species of bacteria. For example, quorum sensing allows *Salmonella* to sense the presence of *Yersinia*. Genes regulated by chromosomal sdiA or AHLs were screened by random transposon-based luciferase fusions in *E. coli* K-12 and *E. coli* O157:H7 for responses to AHL, then tested for sdiA-dependence. Dyszel et al., 5 PLoS ONE e8946 (2010).This method of demonstrating quorum sensing in *Salmonella* works well on motility agar, but poorly in liquid, top agar, or solid agar growth media. See Ahmer et al., 52 Molec. Microbiol. 933 (2004); Smith & Ahmer, 185 J. Bacteriol. 1357 (2003). Such studies provided a strategy for genetic screening to identify novel microbial interaction systems, such as using parallel screening methods (TraSH or Tn-seq) to identify genes required for fitness within the gastrointestinal tract. This generates a list of hundreds of genes, from which a second screen that differs in only one variable provides a list of differentially required genes which is comparatively quite small. An outline of these screening methods is shown in FIG. 10A to FIG. 10D; FIG. 11.

Figure 11B:
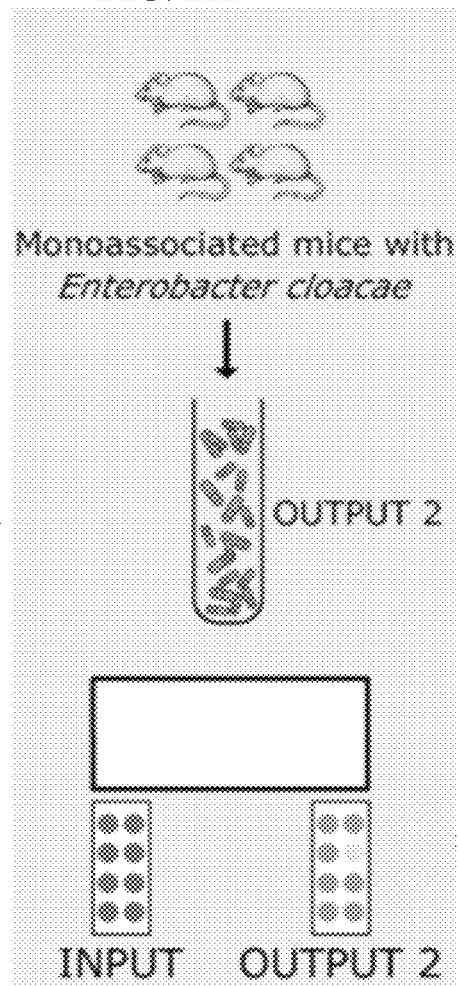
Figure 12A:
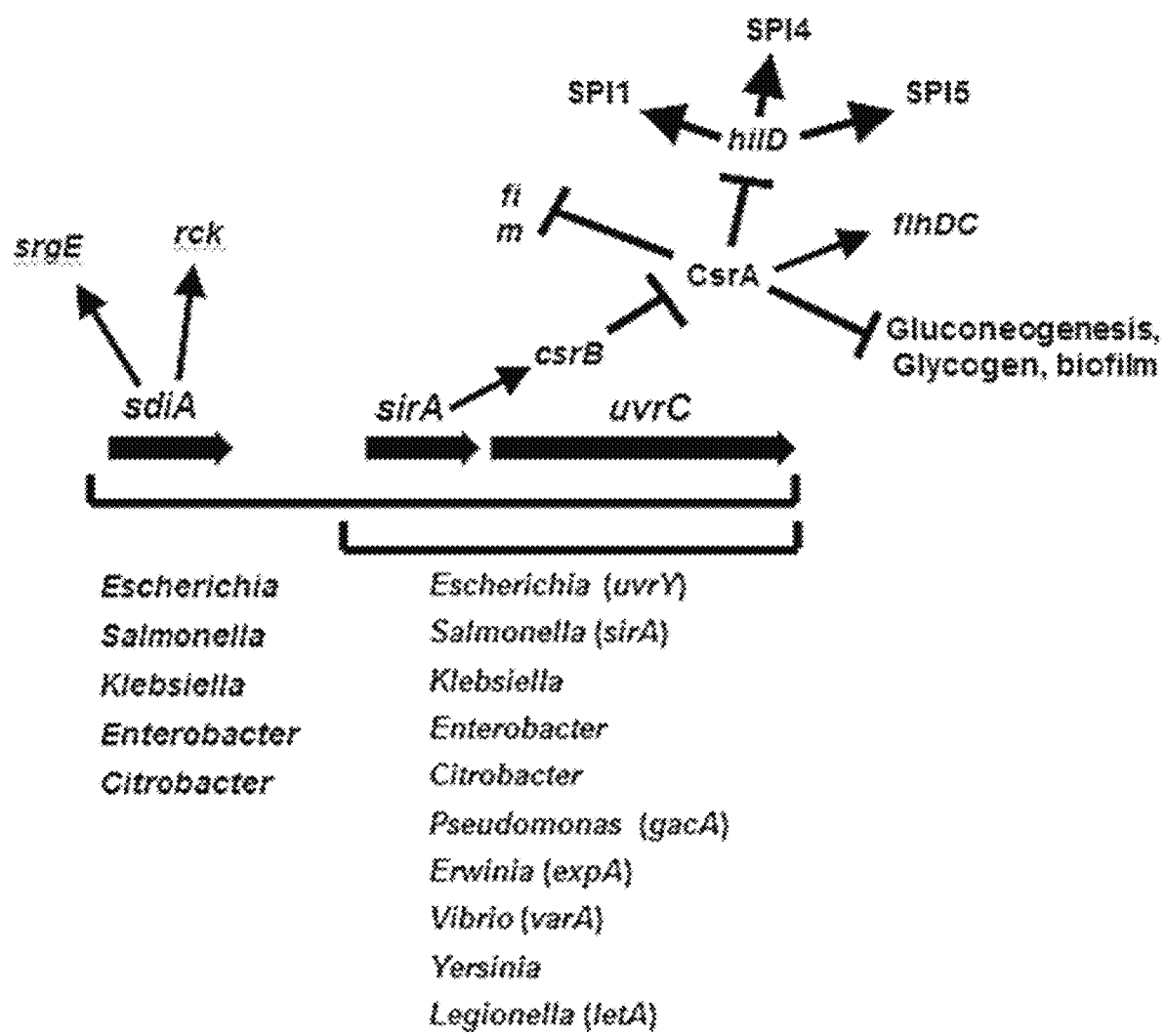
FIG. 12A diagrams the results of a fitness screen in which five genes were identified as being differentially required. See Table 1. The top two genes identified in the screen were sirA/barA genes.
Figure 12B:
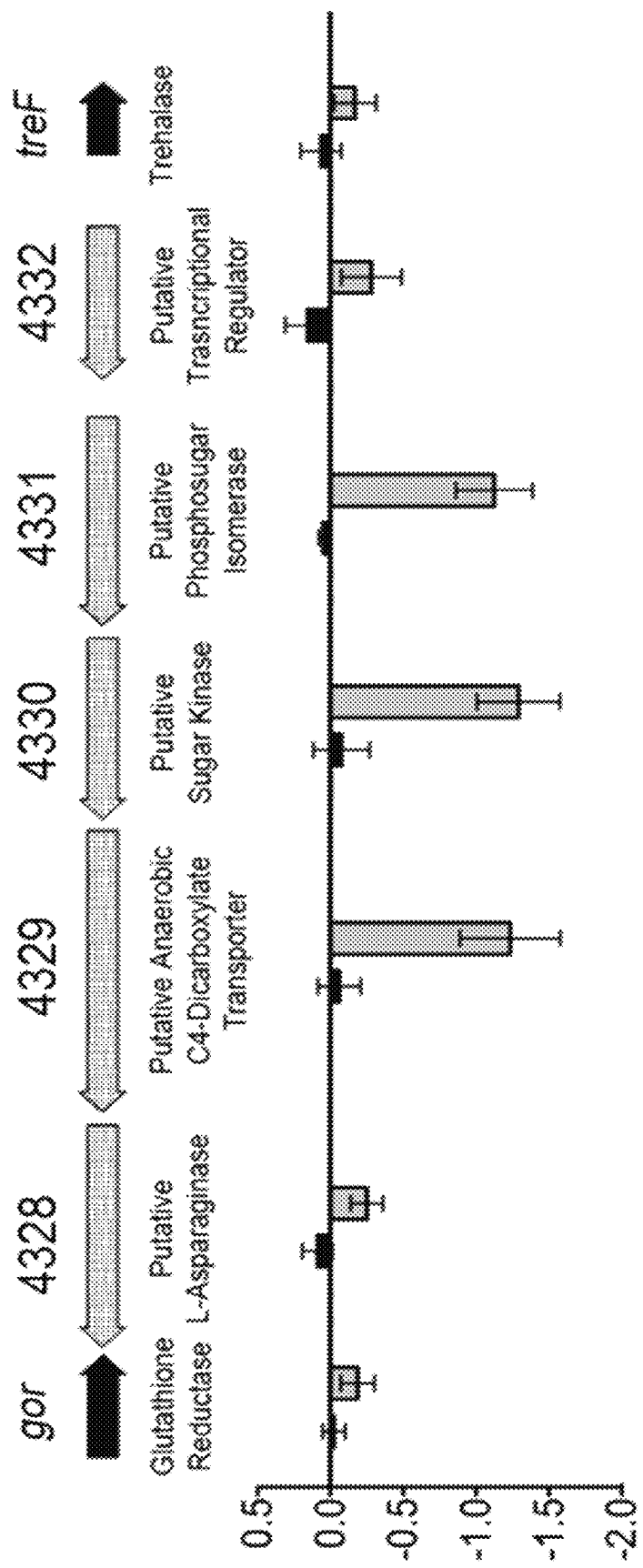
FIG. 12B shows the genes involved in nutrient uptake locus that was also identified in the screen. y-axis: $Log_2$ (Input/Output). The differential requirement for sirA/barA in germ-free mice versus *Enterobacter*-monoassociated mice could be due to one environment being gluconeogenic (germ-free) and the other being glycolytic (Entero) (Table 1). This can be tested by adding glucose to drinking water, which makes the competition favor wild-type, as if Entero were present.
Figure 12C:
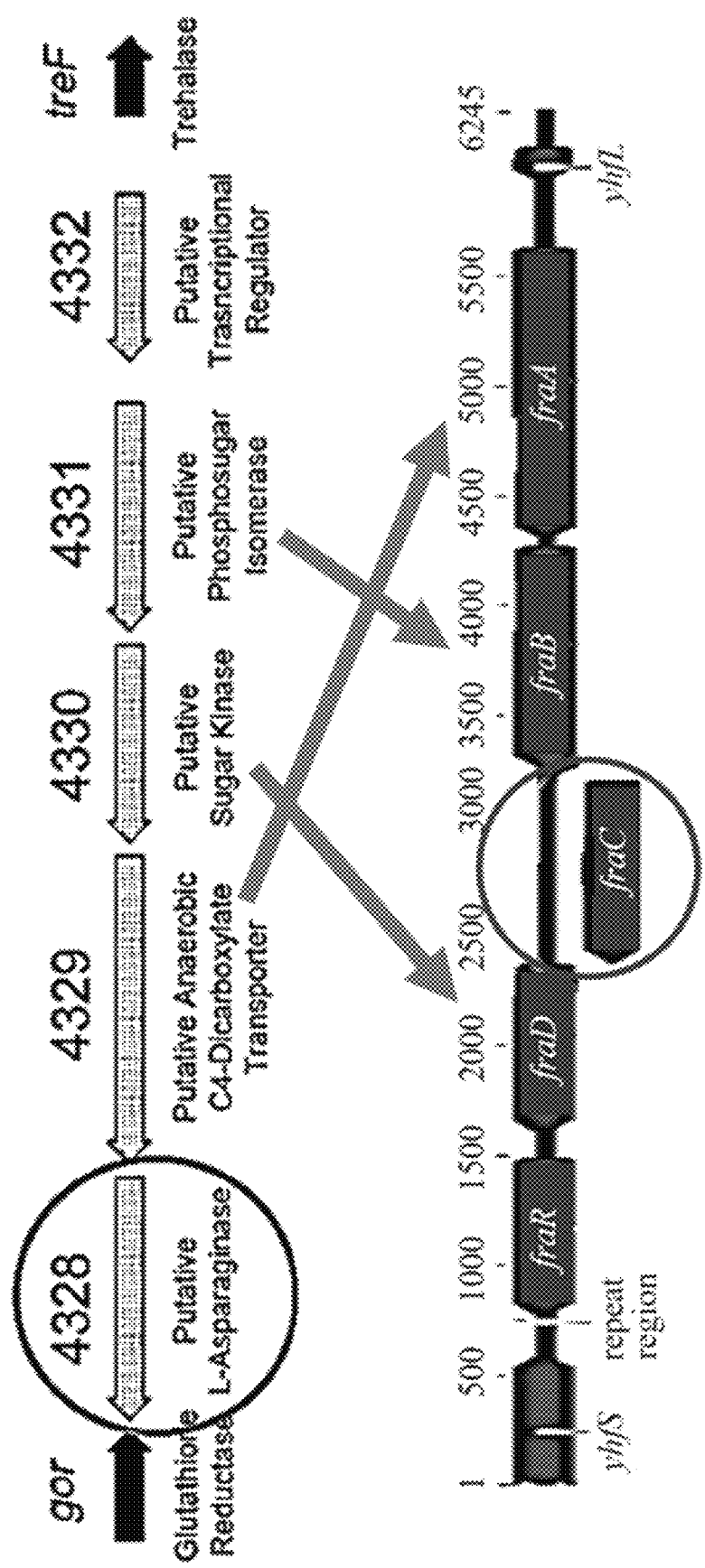
FIG. 12C diagrams how a substrate of the nutrient uptake locus was identified in *E. coli*, in particular the *E. coli* frl locus that enables fructose-lysine (F-Lys) utilization. Adapted from Wiame et al., 277 J. Biol. Chem. 42523 (2002).
Figure 14:
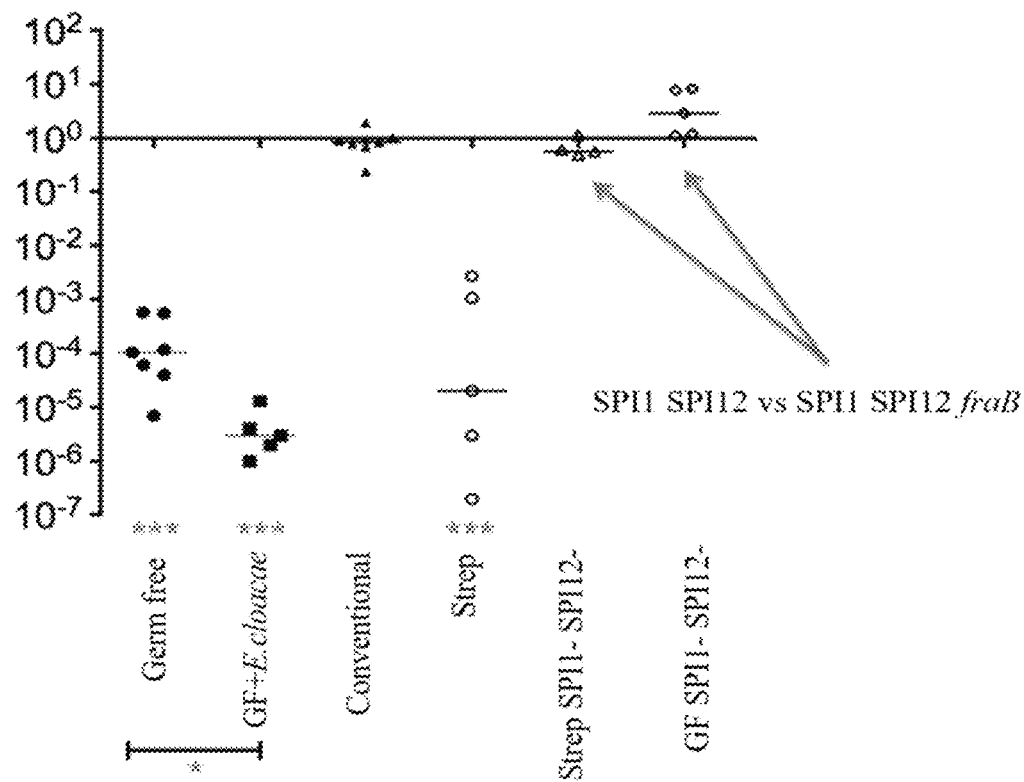
FIG. 14 demonstrates that loss of SPI1 and SPI2 resulted in loss of phenotype. y-axis: competitive index; *$P<0.05$; ***$P<0.001$.
Figure 15:
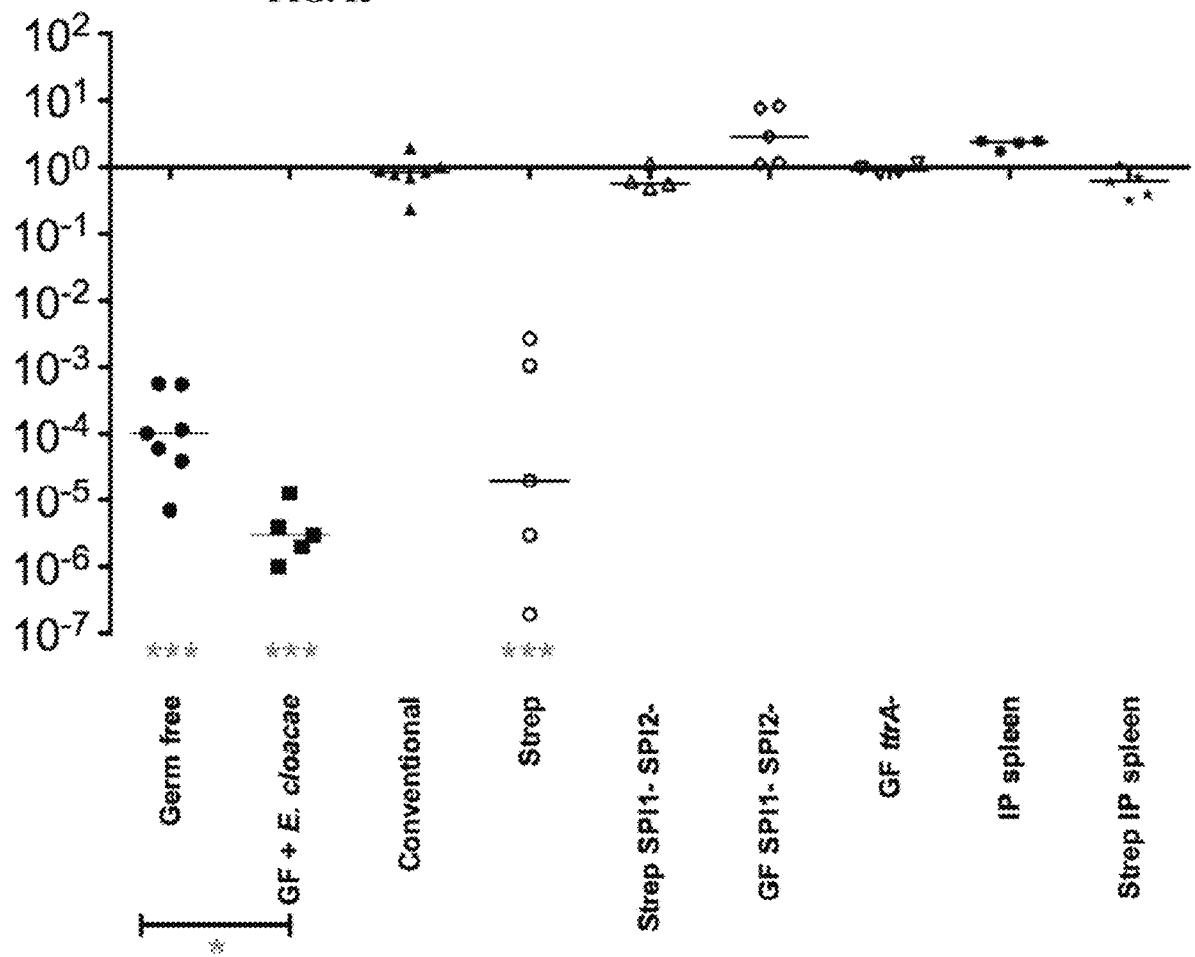
FIG. 15 demonstrates that there is no phenotype exhibited during systemic *Salmonella* infection. The competitive index conclusion is that the fraB mutant is attenuated in germ-free, strep-treated, IL-10 mice, and humanized mouse models. The locus is not required in conventional mice, or during systemic infection; and the locus requires SPI1, SPI2, to provide benefit for *Salmonella*. y-axis: competitive index; *$P<0.05$; $P<0.01$; *$P<0.001$.

Screening large libraries of bacterial mutants for fitness defects in animals with defined microbiota can be used to identify those genes that are only required in the presence of specific members of the microbiota. Goodman et al., 6 Cell Host Microbe. 279 (2009). The embodiments described herein reflect a highly reductionist approach and screen for genes that were differentially required in germ-free mice versus ex-germ-free mice colonized with a single, commensal *Enterobacter cloacae* isolate. See FIG. 11A; FIG. 11B; FIG. 12A to FIG. 12C; FIG. 14; FIG. 15. This approach identified only five genes that were differentially required: a two component response regulatory pair, barA/sirA, and three genes within the fra locus, as shown in Table 1:

Individual sirA and fraB mutants were used to confirm the findings. The sirA gene was required for fitness in the presence of *E. cloacae* but not in its absence. The fra locus was required for fitness in both situations, but the phenotype was more severe in the presence of *E. cloacae*. Thus, the differential screening strategy was successful in identifying genes that are more important in the presence of other bacteria within the gastrointestinal tract. See FIG. 12C. The reason(s) that sirA is required in the presence, but not the absence, of *E. cloacae* is uncertain. It is thought that BarA detects short chain fatty acids produced by the normal microbiota and then phosphorylates SirA. SirA then activates the transcription of two small RNAs, csrB and csrC, which antagonize the activity of the CsrA protein (scheme in FIG. 12A). Martinez et al., 80 Mol. Microbiol. 1637 (2011); Lawhon et al., 46 Microbiol. 1451 (2002); Liu et al., 272 J. Biol. Chem. 17502 (1997); Teplitski et al., 296 Int'l J. Med. Microbiol. 449 (2006); Fortune et al., 74 Infect. Immun. 331 (2006); Martinez 196 J. Bacteriol. 325 (2014).

Additionally, the CsrA protein is an RNA-binding protein that regulates the stability and translation of hundreds of mRNAs involved with metabolism and virulence. Romeo et al., 2013; Lawhon et al., 2003; Edwards et al., 80 Mol. Microbiol. 1561 (2011). A possible reason that sirA affects fitness differentially in the two mouse models discussed herein may be that the *Enterobacter*-colonized mouse offers an environment richer in carboxylic acids that act as stimuli for BarA-SirA signaling, with resulting effects on metabolism and growth. Hung et al., 87 Mol. Microbiol. 1045 (2013); Chavez et al., 192 J. Bacteriol. 2009 (2010); Huang et al., 190 J. Bacteriol. 4233 (2008); Lawhon et al., 2002. Further, the fitness effects could also be due to the regulation of genes involved in the induction of inflammation or serovar metabolism including SPI1, SPI2, ethanolamine utilization, and vitamin B12 biosynthesis by CsrA. Lawhon et al., 2003; Martinez et al., 2011; Bustamante et al., 105 PNAS 14591 (2008); Altier et al. 35 Mol. Microbiol. 635 (2000); Johnston et al., 22 Mol. Microbiol. 715 (1996); Ahmer et al., 31 Mol. Microbiol. 971 (1999). Finally, SirA or CsrA may regulate the fra locus itself.

The fra locus had been annotated previously as a C4 dicarboxylate uptake system. As described herein, however, the fra locus played no role in the utilization of C4 dicarboxylates. BLAST searches revealed that the operon is similar to the frl locus of *E. coli*, which is required for the utilization of fructose-lysine (F-Lys). The frl locus of *E. coli* has a different genomic context than the fra locus of *Sal-*

TABLE 1

Genes differentially required in germ-free mice and ex-germ-free mice monoassociated with *Enterobacter cloacae*

| Locus tag[a] | Symbol | Description | Germ-free mice[b] | *Enterobacter* monoassociated mice[c] | Difference[d] |
|---|---|---|---|---|---|
| STM14_2365 | sirA | response regulator | 1.88 | −0.27 | −2.15 |
| STM14_3566 | barA | hybrid sensory histidine kinase | 1.09 | −0.55 | −1.64 |
| STM14_4330 | fraD | putative sugar kinase | −0.07 | −1.29 | −1.22 |
| STM14_4331 | fraB | putative phosphosugar isomerase | 0.05 | −1.12 | −1.18 |
| STM14_4329 | fraA | putative transporter | −0.06 | −1.23 | −1.17 |

[a] The locus tag is from the *Salmonella* serovars *Typhimurium* strain 14028 genome (accession number NC_016856.1);
[b] The $\log_2$ hybridization intensity of this locus after recovery of the *Salmonella* library from germ-free mice;
[c] The $\log_2$ hybridization intensity of this locus after recovery of the *Salmonella* library from germ-free mice that had been previously monoassociated with *Enterobacter cloacae*;
[d] The difference in $\log_2$ hybridization intensity of this locus between *Enterobacter* monoassociated mice and germ-free mice.

Figure 2A:
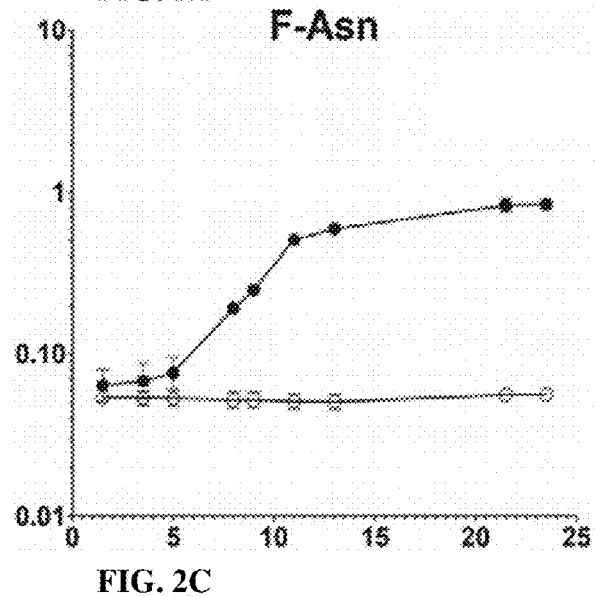
FIG. 2A to FIG. 2E are graphs showing growth of wild-type and fraB1::kan mutant *Salmonella* on Amadori products. Growth of wild-type MA43 and fraB1::kan mutant MA59 on F-Asn (FIG. 2A), F-Arg (FIG. 2B), F-Lys (FIG. 2C), asparagine, arginine, lysine, or glucose (FIG. 2D). Bacteria were grown overnight in Luria Bertani (LB) broth at 37° C. with shaking, centrifuged, resuspended in water, and subcultured 1:1000 into minimal "no carbon E" (NCE) medium (containing trace metals) and the indicated carbon source at 5 mM. The optical density at 600 nm was then read at time points during growth at 37° C. with shaking. Controls included NCE with no carbon source, and NCE with glucose that was not inoculated, as a sterility control (FIG. 2D).
Figure 2B:
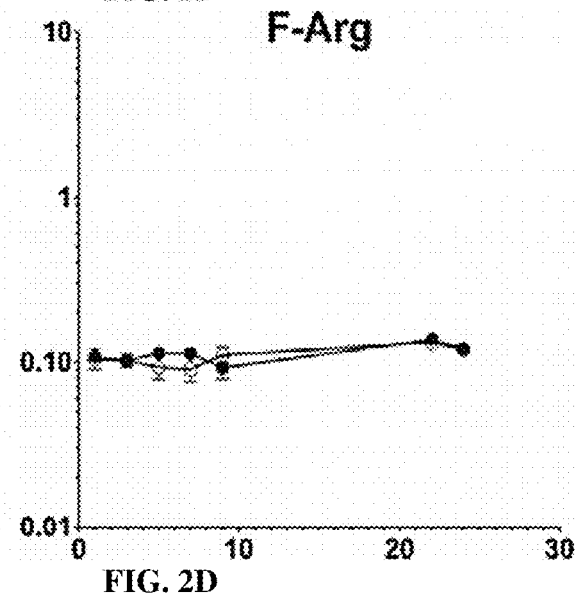
Figure 5:
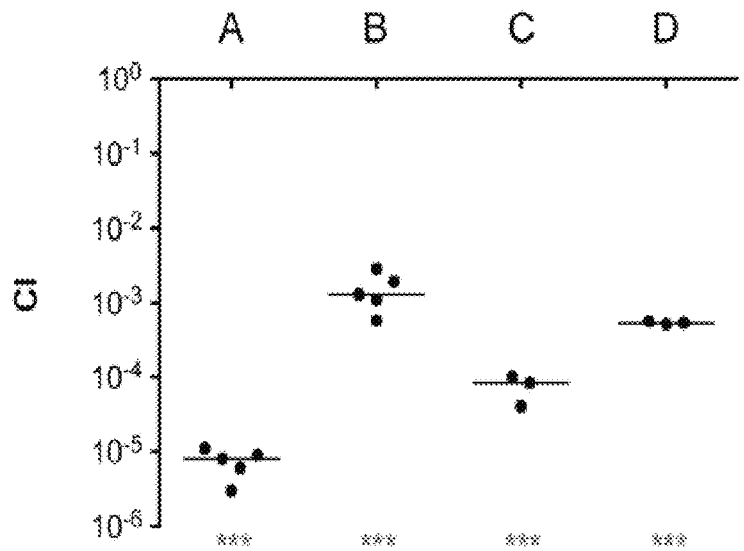
FIG. 5 is a plot showing competitive index (CI) measurements of a fraB1::kan mutant during in vitro growth. Cultures were grown overnight in LB, pelleted and washed in water, subcultured 1:10,000 and grown for 24 hours at 37° C. in NCE minimal medium containing 5 mM F-Asn, aerobically or anaerobically, in the presence or absence of tetrathionate ($S_4O_6^{2-}$), as indicated. Column A shows anaerobic growth in the presence of tetrathionate; column B shows anaerobic growth in the absence of tetrathionate; column C shows aerobic growth in the presence of tetrathionate; column D shows aerobic growth in the absence of tetrathionate. Each data point represents the CI from one culture with the median shown by a horizontal line. Statistical significance of each group being different than 1 was determined by using a one sample Student's t test. Statistical significance between select groups was determined using a Mann-Whitney test. Statistical significance between Column A and Column B: P value<0.01. ***=P value<0.001.
Figure 6:
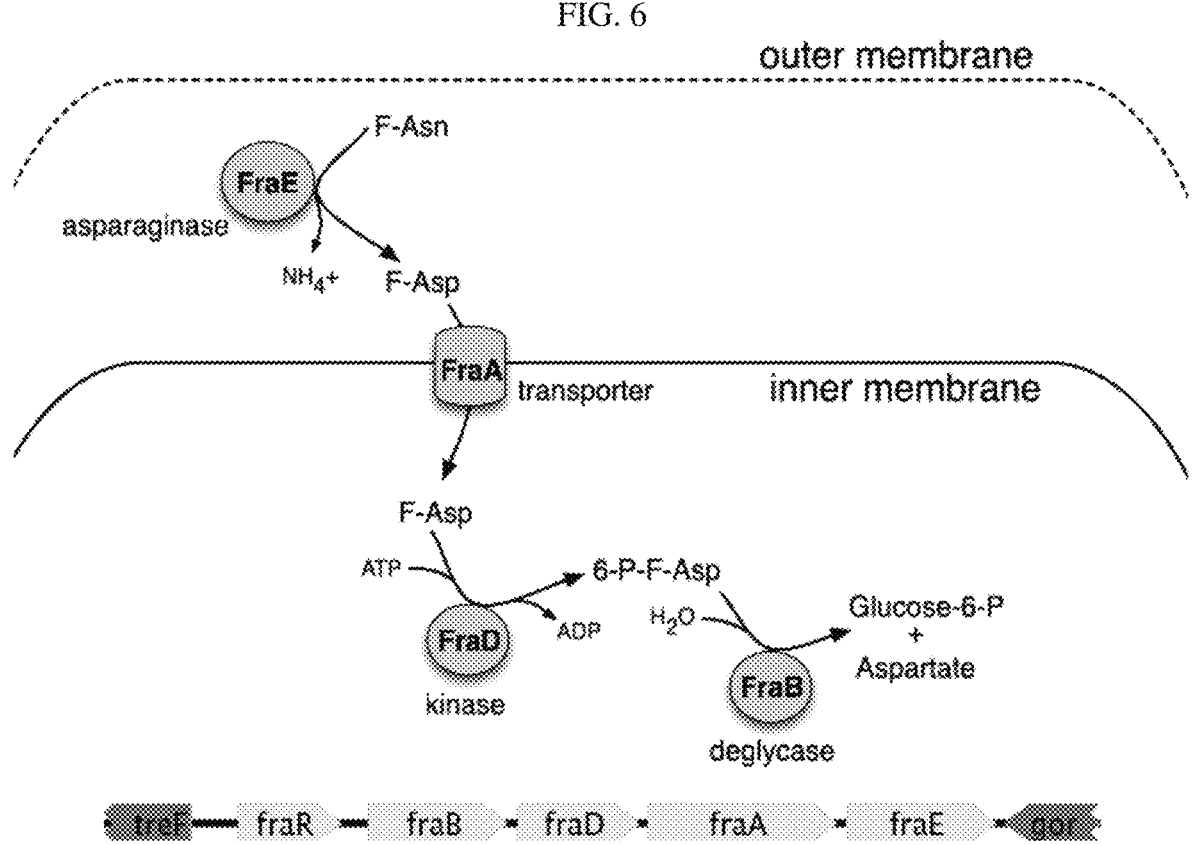
FIG. 6 is a proposed model of Fra protein localization and functions. A proteomic survey of subcellular fractions of *Salmonella* identified FraB (the deglycase) as cytoplasmic and FraE (the asparaginase) as periplasmic. Therefore, it is possible that F-Asn is converted to F-Asp in the periplasm by FraE and that FraA (the transporter) and FraD (the kinase) actually use F-Asp as substrate rather than F-Asn. The FraD kinase of *Salmonella* shares 30% amino acid identity with the FrlD kinase of *E. coli*. FrlD phosphorylates F-Lys to form F-Lys-6-P. Therefore, FraD may phosphorylate F-Asp to form F-Asp-6-P. The FrlB deglycase of *E. coli* shares 28% amino acid identity with FraB of *Salmonella*. In *E. coli*, the FrlB deglycase converts F-Lys-6-P to lysine and glucose-6-P (see Wiame et al., 277 J. Biol. Chem. 42523 (2002)); similarly, FraB of *Salmonella* may convert F-Asp-6-P to aspartate and glucose-6-P.
Figure 7A:
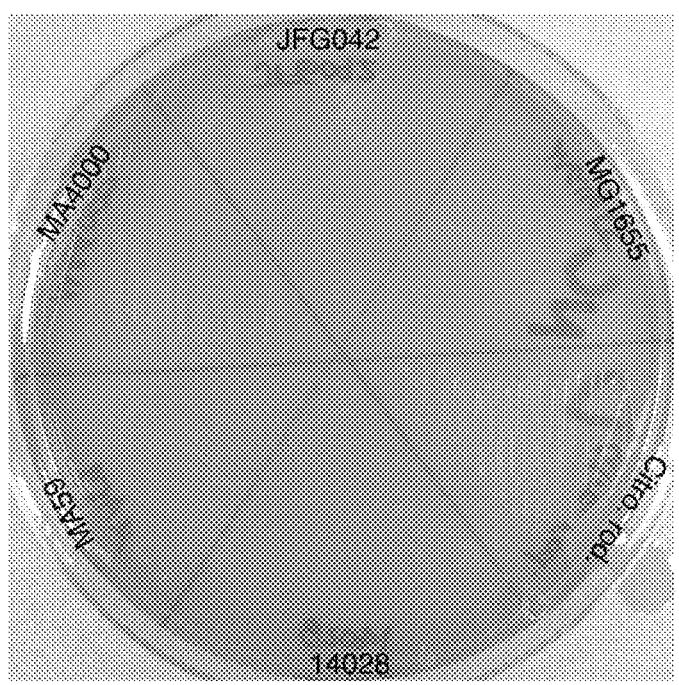
FIG. 7A is a photograph of wild-type *Salmonella* and mutants unable to utilize F-Asn streaked onto an agar plate comprising M9 minimal medium agar and phenol red but no carbon source.
Figure 7B:
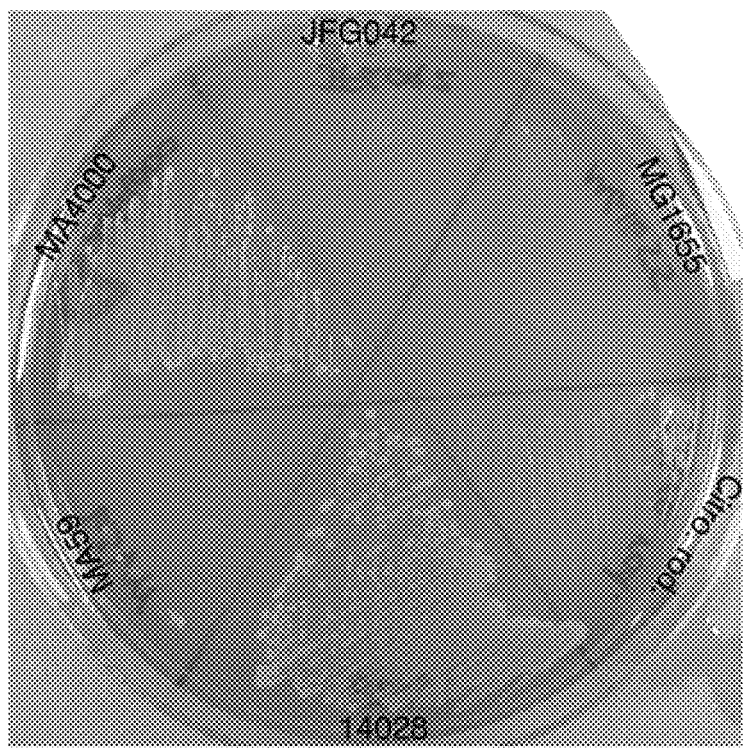
FIG. 7B is a photograph of wild-type *Salmonella* (14028) able to use F-Asn, and *Salmonella* mutants (MA59) and *Citrobacter* (Citro. rod.) unable to use F-Asn as a nutrient on an agar plate comprising M9 minimal medium agar and phenol red, with F-Asn as a carbon source. Phenol red is a pH indicator used frequently in microbiology, changing from red to yellow as the pH value decreases (indicative of fermentation in aerobic environment).
Figure 9:
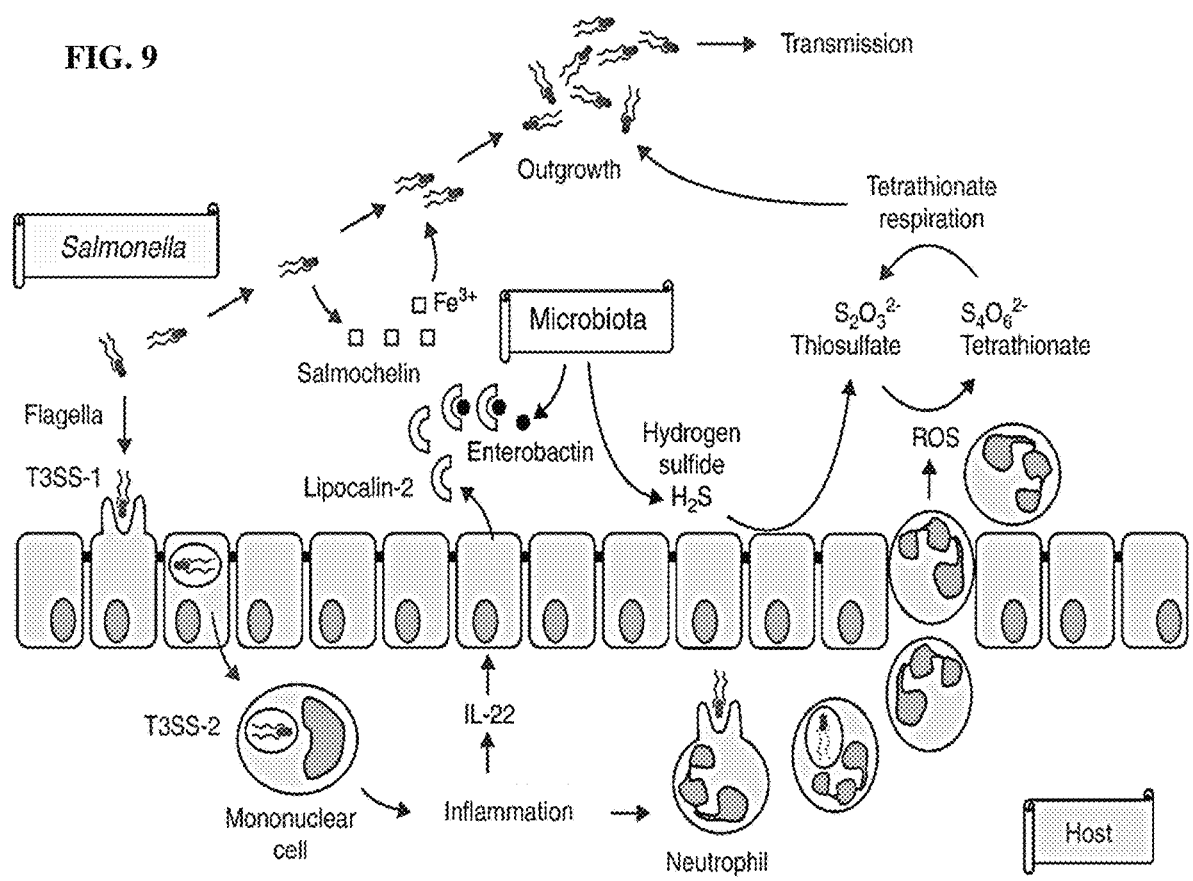
FIG. 9 is an illustration of *Salmonella* inflammation, infection, and host immune responses; which lead to tetrathionate respiration by *Salmonella*. T3SS1 is required for invasion; T3SS2 is required for survival in phagocytes; T3SS effectors, (particularly T3SS-2) induce inflammation, leading to oxidative burst that oxidizes thiosulfate to tetrathionate, which *Salmonella* then respires; thus T3SS effectors are involved in *Salmonella* inflammation and survival. Adapted from Baumler, 15 Current Op. Microbiol. 108 (2012).
Figure 13A:
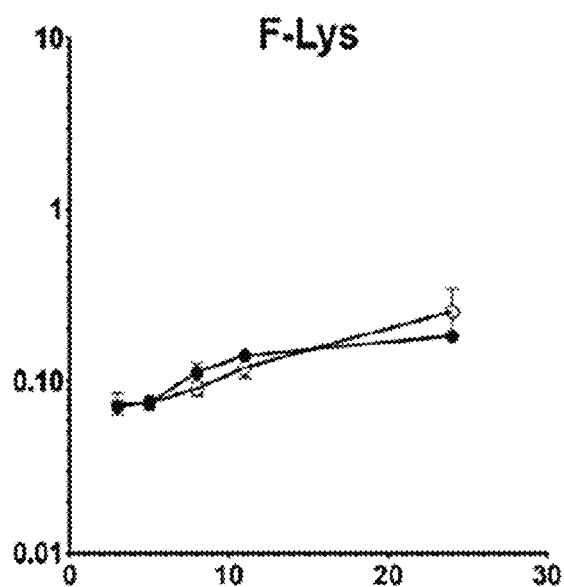
FIG. 13A is graph showing that F-Lys was not the substrate required by *Salmonella*.
Figure 13B:
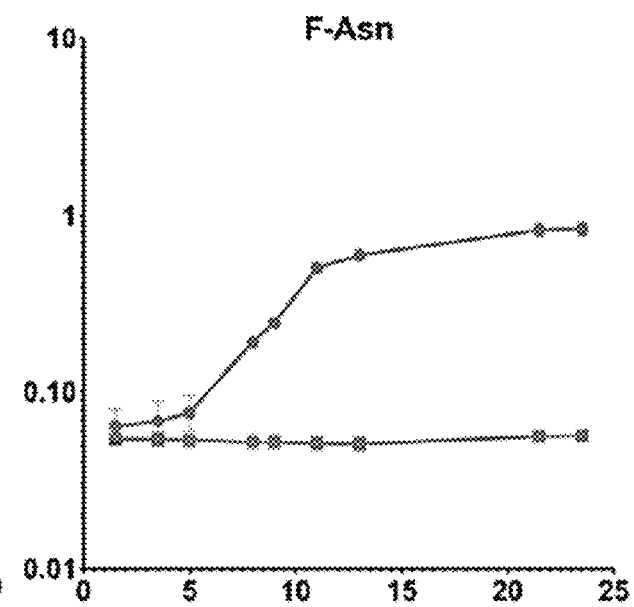
FIG. 13B demonstrates that F-Asn was the substrate for the *Salmonella* nutrient uptake locus identified in the screen. x-axis: time (hours); y-axis: $OD_{600}$.

*monella*, however, and is only distantly related: the fra locus of *Salmonella* plays no role in the utilization of F-Lys (FIG. 2C), nor F-Arg (FIG. 2B). The presence of an asparaginase in the fra locus (fraE), but not the frl locus, led to the hypothesis that F-Asn may be the correct nutrient, and indeed, this was the case. Compare FIG. 13A and FIG. 13B. Wild-type *Salmonella* can grow equally well on F-Asn and glucose, and this ability is dependent upon the fra locus (FIG. 2A to FIG. 2E; FIG. 4A to FIG. 4D). Although previously the individual members of the fra operon had not been characterized fully, the present embodiments confirm their functions are as shown in FIG. 6. F-Asn differs from ethanolamine in that it can be fermented (FIG. 4B; FIG. 7B), which would be consistent with the proposed release of glucose-6-P by FraB (FIG. 6). Yet, although F-Asn can be fermented, it may provide a fitness advantage in vivo when it can be respired (FIG. 4; FIG. 5), possibly because of the much greater energy yield from respiration versus fermentation. In contrast, *E. cloacae* grows very poorly on F-Asn and does not include or express the fra locus. Therefore, *E. cloacae* may exacerbate the fra phenotype of *Salmonella* by competing for other nutrients. See FIG. 9.

The severity of the Fra fitness phenotype would suggest that F-Asn may be a primary nutrient used by *Salmonella* during growth in the inflamed intestine. For perspective, in streptomycin (strep)-treated mice the fitness defect of a fra mutant is 1000-fold, while mutants unable to utilize ethanolamine or sialic acid are attenuated 10-fold and 2-fold, respectively. A fra operon was identified by transcription profiling as upregulated by Fur under anaerobic conditions. Other genes activated under the same conditions included ethanolamine utilization (eut), and a regulator of SPI1 expression (hilA). Both of these loci are associated with induction of inflammation or growth during inflammation. See Thiennimitr et al., 108 PNAS 17480 (2011); Ng et al., 502 Nat. 96 (2013); Troxell et al., 11 BMC Microbiol. 236 (2011). The fra locus is present among most *Salmonella* serovars, but is disrupted in serovars *Typhi* and Paratyphi A, consistent with the marked degradation of numerous loci involved with anaerobic respiration among these extraintestinal serovars. Nuccio & Baumer, 5 MBio e00929 (2014). Interestingly, a putative fra locus may be present in *Citrobacter rodentium* (but see FIG. 7B showing *C. rod.* did not grow on F-Asn medium) and *C. freundii*, but not in numerous other non-pathogenic *Citrobacter* species; and a putative fra locus may be present in Clostridia. The frl locus, encoding the ability to utilize F-Lys is present in *E. coli*, *Shigella*, and *Cronobacter*. The knowledge that *Salmonella* utilizes F-Asn enables further characterization of other members of the microbiota that may compete with *E. coli* and *Salmonella* for Amadori products.

The *Salmonella* F-Asn utilization system was discovered during a genetic screen designed to identify novel microbial interactions between *Salmonella* and the normal microbiota. Transposon site hybridization (TraSH) was used to measure and compare the relative fitness of *Salmonella* transposon insertion mutants after oral inoculation and recovery from the cecum of two types of gnotobiotic mice, differing from each other by a single intestinal microbial species (FIG. 10A to FIG. 11B). See Chaudhuri et al., 5 PLoS Pathog. e1000529 (2009); Santiviago et al., 5 PLoS Pathog. e1000477 (2009); Lawley et al., 2 PLoS Pathog. ell (2006); Badarinarayana et al., 19 Nat. Biotechnol. 1060 (2001); Sassetti et al., 98 PNAS 12712 (2001); Goodman et al., 6 Cell Host Microbe. 279 (2009). The two types of mice were germ-free and ex-germ-free colonized by a single member of the normal microbiota, *Enterobacter cloacae*.

The bacterium *E. cloacae* was chosen because it is a commensal isolate from laboratory mice, easily cultured, genetically tractable, and it protects mice against *Salmonella* infection. In total, five genes conferred a greater fitness defect in the mice containing *Enterobacter* than in the germ-free mice (see Table 1, above). Two of these genes, barA and sirA (uvrY), encode a two-component response regulator pair that is conserved throughout the c-proteobacteria. Teplitski et al., in GLOBAL REG. NETWORKS IN ENTERIC BACTERIA, at 107 (Pruss, Ed., 2005); Romeo et al., 15 Environ. Microbiol. 313 (2013); Lapouge et al., 67 Molec. Microbiol. 241 (2008). BarA/SirA control the activity of the CsrA protein (carbon storage regulator) that coordinates metabolism and virulence by binding to and regulating the translation or stability of mRNAs for numerous metabolic and virulence genes, including those encoding SPI1, SPI2, and glgCAP (glycogen biosynthesis). Romeo et al., 2013; Lawhon et al., 48 Molec. Microbiol. 1633 (2003); Martinez et al., 80 Molec. Microbiol. 1637 (2011).

The fitness of the BarA/SirA regulatory system phenotype was confirmed by performing competition experiments in which wild-type *Salmonella* was mixed in a 1:1 ratio with an isogenic sirA mutant and inoculated orally into germ-free mice and ex-germfree mice colonized by *Enterobacter*. The results of TraSH analysis suggested that the sirA mutant would be at a greater growth disadvantage in *Enterobacter* mono-associated mice than in germ-free mice (Table 1; see also FIG. 12A to FIG. 12C). Results of the competition experiment confirmed this prediction.

The other three genes identified by TraSH analysis had not been characterized previously, and are located together in a putative operon. Genome annotation suggested that they encode a C4 dicarboxylate transporter, a sugar kinase, and a phosphosugar isomerase (see FIG. 12B). A putative asparaginase lies at the end of the operon, and a separate gene upstream of the operon encodes a putative transcriptional regulator of the GntR family. These genes are not present in *E. coli*, and appear to represent a horizontal acquisition inserted between the gor and treF genes at centisome 77.7 of the *Salmonella* 14028 genome (ORFs STM14_4328 to STM14_4332). These genes are designated fraBDAE and fraR for the reasons described herein.

A fraB1::kan mutation was constructed and tested for fitness in germ-free and *Enterobacter*-colonized mice using 1:1 competition assays against the wild-type *Salmonella*. The TraSH results suggested that this locus would exhibit a differential fitness phenotype in germ-free mice and *Enterobacter* mono-associated mice. Indeed, disruption of the fra locus caused a severe fitness defect in germ-free mice and a more severe defect in *Enterobacter*-colonized mice.

Competition experiments indicated that the fra locus conferred a fitness advantage during inflammation and anaerobic respiration in this model. More specifically, competition experiments between wild-type and the fraB1::kan mutant were performed using conventional mice (with normal microbiota) and mice treated orally with streptomycin (strep-treated) one day earlier to disrupt the microbiota. Conventional mice do not become inflamed from *Salmonella*, while strep-treated mice (or germ free) do become inflamed. Stecher et al., 2007; Winter et al., 2010; Thiennimitr et al., 2011; Barthel et al., 71 Infect. Immun. 2839 (2003); Woo et al., 3 PLoS ONE e1603 (2008); Garner et al., 77 Infect. Immun. 2691 (2009); Kaiser et al., 245 Immunol. Rev. 56 (2012). Disruption of the fra locus caused no fitness defect in conventional mice, but caused a severe defect in the strep-treated mice at one and four days post-infection. The phenotype in strep-treated mice was confirmed by complementation. It is expected that the fraB1::kan mutation is polar on the remainder of the fraBDAE operon. Therefore, the fraB1::kan mutation was complemented with a low copy number plasmid encoding the entire fra island. The phenotype was confirmed again using a separately constructed mutation, fraB4::kan, and complementation. In both instances, greater than 99% of the phenotype was restored.

The observation of a phenotype in germ-free and strep-treated mice, but not conventional mice, suggested initially that *Salmonella* might require inflammation in order to acquire or utilize the fra-dependent nutrient source. It is known that inflammation causes the accumulation of tetrathionate in the lumen, a terminal electron acceptor that allows *Salmonella* to respire anaerobically. Winter et al., 2010. Histopathology results indicated that infection with *Salmonella* caused inflammation in the germ-free and strep-treated mice, but not in the conventional mice. To test whether *Salmonella* must induce inflammation for fra to affect the phenotype, the competition experiments were repeated in a *Salmonella* genetic background lacking SPI1 and SPI2, so that both the wild-type and the fra mutant would be defective for induction of inflammation. See FIG. 14; FIG. 15. The severe fitness phenotype of the fra mutant was not observed in these strains, however, and histopathology results confirmed that inflammation was indeed low during these experiments.

The electron acceptor tetrathionate allows *Salmonella* to grow anaerobically on ethanolamine or 1,2-propanediol by using endogenously synthesized B12. Genes involved in this metabolism include the ttr operon, which encodes tetrathionate reductase. This operon is globally regulated by OxrA (Fnr) and induced anaerobically by a two-component system in response to tetrathionate. *Salmonella* reduces tetrathionate to thiosulfate, which it can further reduce to H2S, by using enzymes encoded by the genes phs and asr. The genes for 1,2-propanediol degradation (pdu) and B12 synthesis (cob), along with the genes for sulfur reduction (ttr, phs, and asr), constitute more than 1% of the *Salmonella* genome and are absent from *E. coli*. Price-Carter et al., 2001.

Competition experiments confirmed that the fra locus is not required during the systemic phase of disease. More specifically, competition experiments were performed between the wild-type and the fra mutant after intraperitoneal inoculation of conventional or antibiotic-treated mice, with bacterial recovery from the spleen. The fra mutant had no fitness defect during systemic infection. The fra phenotype was first observed using C57BL/6 mice transgenic for the Nramp1 locus (Govoni et al. 64 Infect. Immun. 2923 (1996)) as a host. This required that the mice be either germ-free or streptomycin-treated (strep-treated) so that *Salmonella* could induce inflammation. The significance of the fra locus may be determined in a model that is not mutated and does not require strep-treatment or a germ-free status. In comparison, humans with a complete microbiota are quickly inflamed by *Salmonella* infection when conventional mice are not; and more recently it was discovered that germ-free mice colonized with human fecal microbiota ("humanized" mice) become inflamed from *Salmonella* infection without disturbance of the gut microbiota by streptomycin. Chung et al., 149 Cell 1578 (2012).

Therefore, germ-free Swiss Webster Nramp1$^{+/+}$ mice were humanized with human feces obtained from a healthy adult donor from the Ohio State University fecal transplant center. Competition experiments were then performed between wild-type and fra mutant *Salmonella* in these mice. Histopathology results confirmed the presence of mild inflammation during these experiments, and the fra locus had a greater than 10,000-fold fitness phenotype.

Additionally, IL10-knockout mice were used as another method to facilitate *Salmonella*-induced inflammation without using streptomycin. See Stecher et al., 2007. Histopathology results indicated that, unexpectedly, there was not very much inflammation in these mice by day 3 post-infection although the fra locus still had a modest fitness phenotype (greater than 100-fold). The phenotypes of the fra locus in IL10 knockout mice and in the humanized Swiss Webster mice demonstrate that the Fra phenotype is not limited to germ-free or streptomycin-treated mice. See also FIG. 24.

Further, whether these severe fra mutant phenotypes were the result of interaction between the wild-type and fra mutant during infection was examined in experiments in which strep-treated C57BL/6 Nramp1$^{+/-}$ heterozygous mice were infected separately with *Salmonella* wild-type, *Salmonella* fra mutant, or *Salmonella* complemented with fra mutant. The strains were quantitated in the feces each day post-infection for four days at which point the mice were sacrificed and the strains were quantitated in the cecum. The fra mutant was recovered in 30-fold lower numbers than wild-type on the fourth day in the feces and 98-fold lower in the cecum. This defect was restored by complementation with the fra locus on a plasmid in the cecum, although in the feces the restoration did not reach statistical significance.

Importantly, the fra locus is required for growth on F-Asn. FraA is homologous to the Dcu family of dicarboxylate transporters. Authentic dicarboxylate acquisition loci do not, however, encode a sugar kinase or phosphosugar isomerase. Furthermore, none of the dicarboxylates tested (malate, fumarate, or succinate) provided a growth advantage to the wildtype strain vs. a fraB1::kan mutant, suggesting that they are not substrates of the Fra pathway. BLAST searches using the entire operon revealed that the closest homolog is the frl operon of *E. coli*, although the frl operon is at a different location within the genome and does not encode an asparaginase (and the *Salmonella* fra locus does not encode a frlC homolog). The products of the *E. coli* frl operon transport and degrade the Amadori product fructose-lysine (F-Lys). Wiame et al., 378 Biochem. J. 1047 (2004); Wiame et al., 277 J. Biol. Chem. 42523 (2002).

Amadori products most often result from a spontaneous reaction between a carbonyl group (often of glucose, although numerous other compounds can also react) and an amino group of an amino acid in vivo, and are then referred to as non-enzymatic glycation products. Zhang et al., 8 J. Proteome. Res. 754 (2009); Tessier, 58 Pathol. Biol. 214 (2010). With F-Lys and fructose-arginine (F-Arg) this can happen with the free amino acid, or the side groups of the lysine and arginine residues of a protein. In contrast, fructose-asparagine (F-Asn) can only result from reaction of glucose with the alpha amino group of free asparagine or the N-terminal asparagine of a protein. Three different Amadori products, F-Asn, F-Arg, and F-Lys, were synthesized and used as sole carbon sources during growth experiments. The preparations were free of glucose but contained some free amino acid. Control experiments demonstrated, however, that *Salmonella* was unable to grow on any of the three amino acids alone, so these contaminants are inconsequential.

Figure 2C:
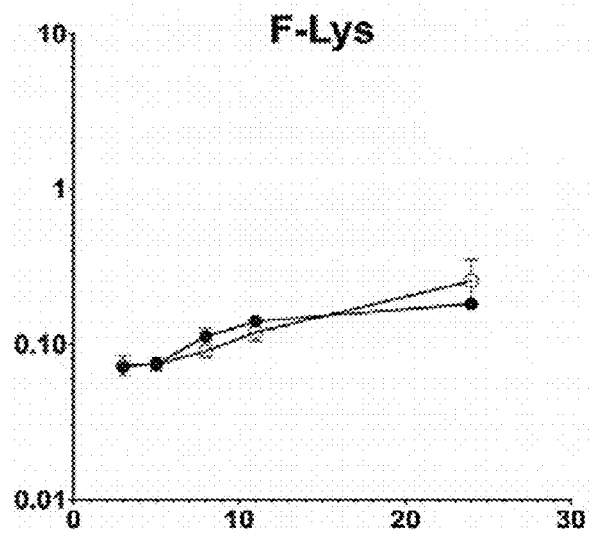
Figure 2D:
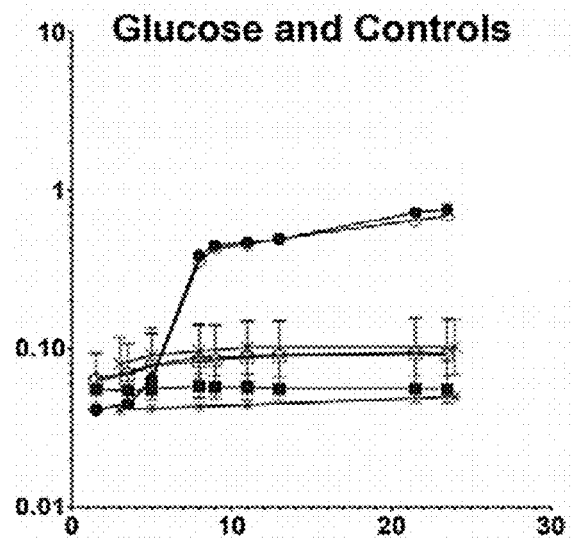
Figure 2E:
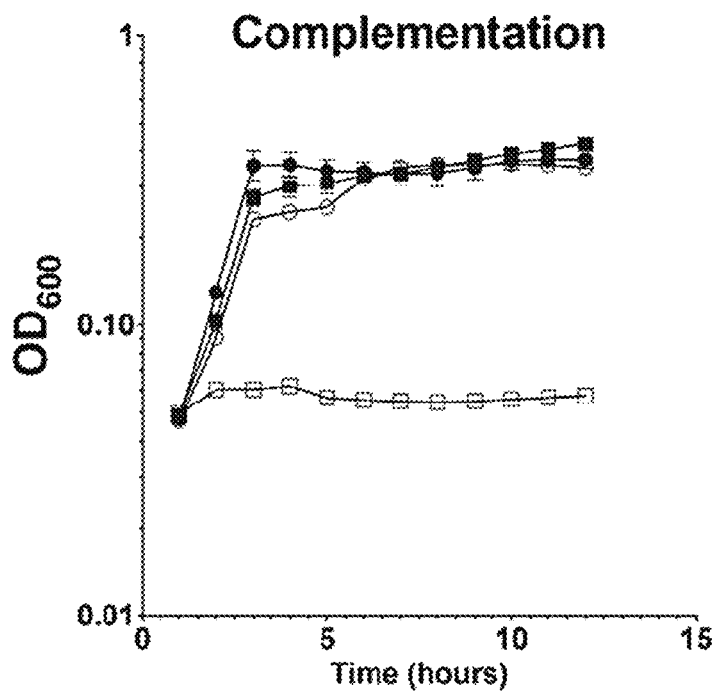
Figure 3:
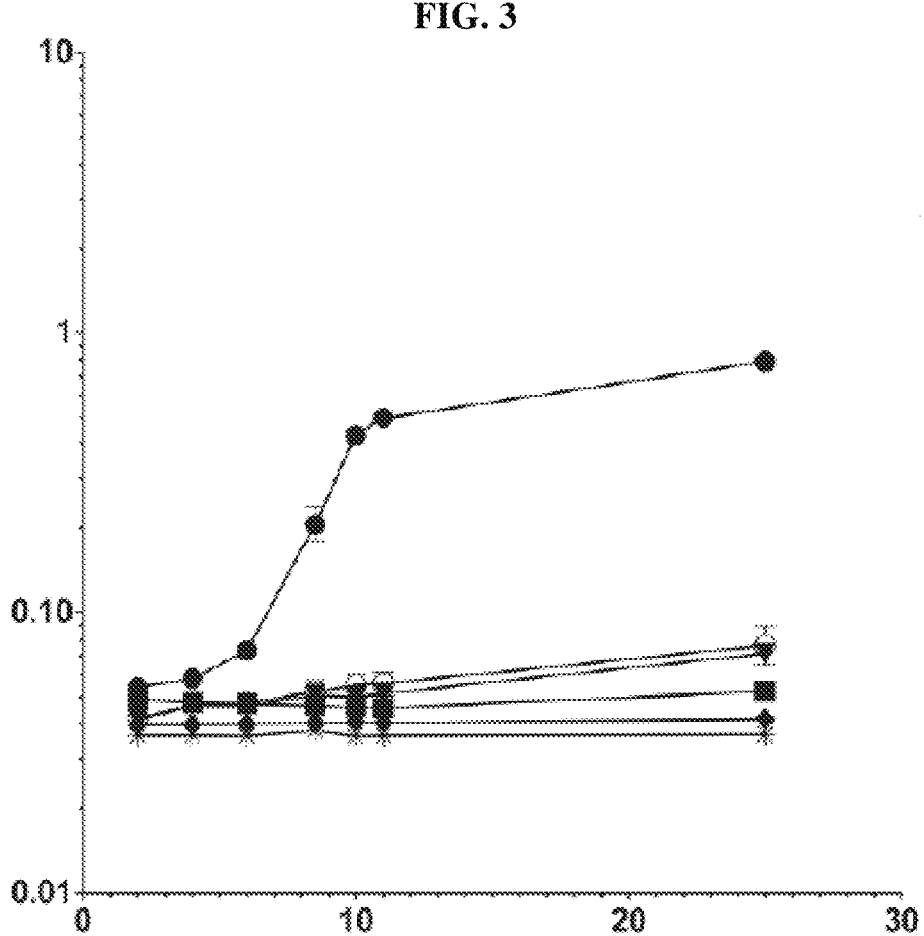
FIG. 3 is a graph showing growth of *Salmonella* wild-type MA43 and fraB1::kan mutant MA59 on F-Asn as sole nitrogen source (see also FIG. 7B). Bacteria were grown overnight in LB at 37° C. shaking, centrifuged, resuspended in water, and subcultured 1:1000 into NCE medium lacking a nitrogen source (NCE-N) but containing the indicated carbon source at 5 mM. The optical density at 600 nm was then read at time points during growth at 37° C. with shaking. Controls included NCE-N with no carbon source, NCE-N with 5 mM glucose, and NCE-N with glucose that was not inoculated, as a sterility control. Each point represents the mean of four cultures and error bars represent standard deviation. ● F-Asn wild-type; ■ F-Asn fraB mutant; ○ Glucose wild-type; ▼ Glucose fraB mutant; ◆ No carbon source; * Sterility; x-axis: time (hours); y-axis: $OD_{600}$.

*Salmonella* was unable to grow on F-Arg, and grew slowly and with low yield on F-Lys (FIG. 2B, FIG. 2C). The growth on F-Lys was independent of the fra locus. In contrast, *Salmonella* grew as well on F-Asn as on glucose, and growth on F-Asn was dependent upon the fra locus (hence the name fra, for fructose-asparagine utilization) (FIG. 2A). A commercial source of F-Asn was obtained, and it also allowed *Salmonella* to grow in a fra-dependent manner. Complementation of the fraB1::kan mutant with a plasmid encoding the fra island restored the ability of the mutant to grow on F-Asn (FIG. 2E). In addition to serving as a sole carbon source, F-Asn, also served as sole nitrogen source (FIG. 3).

Growth with F-Asn was tested under aerobic and anaerobic conditions in the presence or absence of the terminal electron acceptor tetrathionate (FIG. 4A to FIG. 4D). The F-Asn was utilized under all conditions, but respiratory conditions were superior with *Salmonella* doubling times of 1.6±0.1 hours aerobically with tetrathionate; 2.0±0.3 hours aerobically without tetrathionate; 1.9±0.1 hours anaerobically with tetrathionate; and 2.9±0.4 hours anaerobically without tetrathionate. Competition experiments in which the wild-type and fraB1::kan mutant were grown in the same culture were performed in minimal medium containing F-Asn. As expected, the mutant was severely attenuated during aerobic and anaerobic growth, and in the presence or absence of tetrathionate (FIG. 5). Indeed, the attenuation was most severe during anaerobic growth in the presence of tetrathionate.

Hence, the present embodiments provide a culture medium for investigating, isolating, counting, and directly identifying *Salmonella*. The medium promotes the growth of *Salmonella*, but not the growth of non-*Salmonella* organisms. The present embodiments provide a *Salmonella*-selective medium comprising F-Asn as a nutrient. The present embodiments also provide a *Salmonella*-selective medium comprising F-Asn as the sole nutrient. The use of the term "sole" does not refer to 100% absence of other nutrient sources, but rather a substantial absence of other nutrients such that the *Salmonella*-selective activity of the medium is exhibited. The base media may be any minimal media, as these are well-known in the art, such as M9 Minimal medium or Minimal Medium NCE, in which no additional nutrient or carbon source, such as glucose, has been added. Alternatively, the base minimal medium can include glucose and F-Asn, particularly when that medium is used to screen anti-fraB actives as described herein. Additionally, F-Asn can be used with other selective or enrichment components to enhance the features of that media. For example, F-Asn can be added to MacConkey agar to increase its selective function.

The concentration of F-Asn contained in the *Salmonella*-selective medium of the present embodiments can range from about 1 mM to about 40 mM F-Asn, inclusive, such as about 1 mM to about 20 mM F-Asn, inclusive, in a medium in which F-Asn is the sole nutrient source in the medium. For example, the concentration of F-Asn can be from about 5 mM to about 10 mM, inclusive. A typical concentration of F-Asn as a nutrient in a minimal medium is about 5 mM. In some embodiments, 5 mM F-Asn is included as the sole nutrient in the medium. Often, as is known in the art, the amount of F-Asn in a liquid media (enrichment both) can be increased compared with solid media (agar plates) to increase the growth rate and yield of a bacterial culture.

In another embodiment, a *Salmonella* selective culture medium can further include solid support or other means for collecting bacteria from the media. For example, U.S. Pat. No. 8,383,353 refers to suspending microbeads coated with β2GPI proteins in a growth media, culturing a bacterial population in the media, and then collecting the beads to which bacteria have adhered.

The embodiments described herein also provide diagnostic kits that include a *Salmonella*-selective medium as described herein. For example, a kit can include at least one unit of the selective growth medium in liquid or solid form (e.g., agar slab or plate). The *Salmonella*-selective F-Asn medium provided in a kit may be sterile, "ready-to-use" medium, or may be in the form of a concentrated version that can be diluted with sterile water, such as sterile distilled water. Alternatively, the *Salmonella*-selective F-Asn medium provided in a kit may be dried or lyophilized medium that can be reconstituted with sterile water, such as sterile distilled water. Alternatively, the kit may provide an amount, such as an ampule, of sterilized F-Asn that can be added conveniently to a variety of minimal media.

In another embodiment, a kit may further include other media units useful in identifying *Salmonella* or other microbes. The additional media in the kit can be those appropriate for selection of enteric bacteria, or that can serve as a control medium, or provide additional diagnostic information. Such media include, for example: eosin methylene blue (EMB) media, that contains dyes that are toxic for Gram positive bacteria and bile salts which are toxic for Gram negative bacteria other than coliforms (EMB is therefore considered a selective and differential medium for coliforms); MacConkey agar, Hektoen enteric agar (HE), or xylose lysine desoxycholate (XLD) media, all of which are selective for Gram-negative bacteria; or Rappaport-Vassiliadis *Salmonella* enrichment broth. See Rappaport et al., 9 J. Clin. Pathol. 261 (1956); Vassiliadis et al., 44 J. Appl. Bacteriol. 233 (1978).

Alternative kits of the present embodiments include components for genetic- or protein-based identification or diagnosis. For example, kits may include nucleic acid molecules for the identification at least one fra island nucleic acid. Armed with the knowledge provided herein that a functioning fra island is unique *Salmonella*, particularly in the context of suspected *salmonellosis*, the sequence information provided herein, and level of skill in the art, any manner of genetics-based kit can be envisioned and manufactured for the detection of *Salmonella* on the basis of genetic profile. As another example, kits may include antigen-binding molecules such as antibodies, and other components required for immunoassays. As noted, the present embodiments provide for recombinant *Salmonella* Fra proteins that can be used as immunogens to derive antigen binding molecules useful in immunoassays. Because Fra proteins are located within the cell, such kits may include lysis buffers or other means to expose the intracellular milieu to the antigen-binding molecule of the kit. Additionally, the present embodiments provide a recombinant source for Fra proteins useful as a positive control in immunoassays. Further, these proteins can be used in competition assays to titer the amount of *Salmonella* Fra proteins in a sample. The assays of kits comprising the components described herein may be quantitative or qualitative assays.

The kits of the present embodiments may also include devices, containers, or other materials appropriate for the collection of a sample to be tested for the presence of *Salmonella*. The sample may be a biological sample, which may include or be derived from biological tissue, liquid, or solid, capable of containing bacteria. The biological sample may be a stool sample, such as a stool sample from a human or non-human animal. The sample may be a foodstuff or a beverage sample, or a sample obtained from the production or storage of a foodstuff or beverage, including an agricultural sample.

The terms "isolated" or "purified" as used herein refer to a compound, bacterium, nucleic acid, or amino acid that is removed from at least one component with which it is naturally associated.

The terms "promoter" refers to a nucleic acid sequence that functions to direct transcription of a downstream gene, and may be used interchangeably herein with "fra promoter" that directs transcription of the downstream fra gene. As used herein, the term "gene" means the portion or segment of DNA involved in producing a polypeptide chain. The promoter, together with other transcriptional and translational regulatory nucleic acid sequences (also termed "control sequences"), are necessary to express a given gene. In general, the transcriptional and translational regulatory sequences include, but are not limited to, promoter sequences, ribosomal binding sites, transcriptional start and stop sequences, translational start and stop sequences. In particular embodiments, the fra promoter is an inducible promoter, induced by F-Asn. The fra promotor sequence is a DNA sequence recognized by the host organism for expression purposes. *Salmonella* can be engineered such that heterologous proteins are expressed via inducible promotors. See, e.g., U.S. Pat. No. 8,703,153. Those skilled in the art are aware that a natural promoter can be modified by replacement, substitution, addition or elimination of one or more nucleotides without changing its function. The practice of this embodiment is not constrained by such alterations to the promoter as long as it retains some function as an inducible fra promoter.

"Induction" refers to the increased transcription of a gene resulting in the synthesis of a protein of interest in a cell or organism at a markedly increased rate in response to the presence of an "inducer." An "inducer" is a compound that causes cells to produce larger amounts of enzymes or other substances than they would otherwise produce if the inducer was absent. For example, F-Asn is the inducer for the fra promoter. To measure the induction of a protein of interest, cells grown with F-Asn are compared to control samples without F-Asn. For example, control samples (untreated with F-Asn) are assigned a relative protein expression of 100%. Induction of a recombinant gene is achieved when the expression of the recombinant product, relative to the control (no F-Asn), is greater than 100% to 500% or more (i.e., two to five fold higher relative to the control), or even 1000% to 3000% more than the non-induced expression. Expression can be measured by quantity or activity of the recombinant protein.

A nucleic acid is "operably linked" when it is placed into a functional relationship with another nucleic acid sequence. A promoter is operably linked to a coding sequence if it affects the transcription of the sequence. Typically, "operably linked" means that the DNA sequences being linked are contiguous and in reading frame. Recombinant linking is accomplished by ligation at convenient restriction sites. Alternatively, synthetic oligonucleotide adaptors or linkers can be used in accordance with conventional practices, which are well-known in the art.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous," when used with reference to portions of a nucleic acid, indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source (fra) and a coding region from another source. Similarly, a heterologous protein will often refer to two or more subsequences that are not found in the same relationship to each other in nature (e.g., a fusion protein).

The gene operably linked to the inducible fra promoter may encode therapeutically significant proteins or peptides, such as growth factors, cytokines, ligands, receptors, inhibitors, antigens, or antibodies. The gene may encode commercially important industrial proteins or peptides, such as an enzymes or antibodies. The gene of interest may be a naturally occurring gene, a mutated gene or a synthetic gene.

"Antibody" refers broadly to a polypeptide-based antigen binding molecule that comprises a region capable of binding specifically to an antigen. Because the antigen-binding region of an antibody, or its functional equivalent, is typically most critical in specificity and affinity of binding, the term antibody includes antigen-binding portions or fragments of antibodies including all variations of recombinant antigen-binding molecules. The far-inducible promoter is not limited to expression of any particular antibody. Similarly, antigen binding proteins generated against the *Salmonella* Fra proteins described herein are not limited to a particular epitope of the Fra protein or type of antigen binding molecule.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient expression. Additional elements of the cassette may be included. In addition to a promoter sequence, the expression cassette should also contain a transcription termination region downstream of the structural gene to provide for efficient termination. The termination region may be obtained from the same gene as the promoter sequence (i.e., fra) or may be obtained from different genes.

The particular expression vector used to transport the genetic information into the recombinant host cell is not particularly critical. Any of the conventional vectors used for expression in prokaryotic cells may be used. Standard bacterial expression vectors include bacteriophages λ and M13, as well as plasmids such as pBR322 based plasmids, pSKF, and pET23D. Fusion expression systems such as MBP, GST, and LacZ are useful. Additional amino acids to ease purification, such as epitopes or $(His)_6$ tag-recombinant polypeptides, can be included in the heterologous protein. Elements typically included in expression vectors include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable; but because of the selective nature of F-Asn, additional selection markers may not be required if a functional far locus is included in the vector or otherwise expressed in the host cell.

Any of the well-known procedures for introducing foreign nucleotide sequences into host cells may be used. After the expression vector is introduced into the host microbes, the bacteria are cultured in F-Asn-based media under conditions favoring expression of genes under control of the fra promoter sequences. Large batches of transformed host bacteria can be cultured. Finally, product is recovered from the culture using standard techniques. Thus, the some embodiments provide for the expression of desired polypeptides whose expression is under control of the fra gene promoter sequences, including naturally occurring fra genes, fusion DNA sequences, and various heterologous polypeptide constructs. Optimal conditions for the production of recombinant proteins may vary with the choice of both the host cell and the protein to be expressed, but one skilled in the art can make such adjustments without undue experimentation.

Accordingly, a particular embodiment provides for a method for producing a recombinant protein comprising: (a) introducing into a *Salmonella* host cell an expression vector encoding a recombinant protein under the control of an inducible fra promoter to form a recombinant bacterial cell; (b) introducing the recombinant *Salmonella* cell into a culture medium to form a cell culture; (c) adding F-Asn to the cell culture, optionally as a continuous feed, optionally with an additional nutrient as a continuous feed (d) monitoring cell growth in the cell culture for achievement of a threshold optical density ($OD_{600}$); (e) adding F-Asn as the sole nutrient as an inducer of the inducible promoter to the cell culture as a continuous feed once the threshold optical density ($OD_{600}$) is achieved, wherein the total amount of F-Asn inducer added to the culture is from 5 mM to 40 mM; and (f) isolating the recombinant protein.

Another aspect of the present embodiments provides a target for inhibiting *Salmonella* growth. An "inhibitor" refers to an agent capable of blocking, neutralizing, inhibiting, abrogating, reducing or interfering with one or more of the activities of a target or reducing the expression of the target protein (or the expression of nucleic acids encoding the target protein). Inhibitors include antibodies, polypeptides, peptides, nucleic acid molecules, short interfering RNAs (siRNAs) and other inhibitory RNAs, small molecules (e.g., small inorganic molecules), polysaccharides, polynucleotides, antisense oligonucleotides, aptamers, and peptibodies. An inhibitor may decrease the activity or expression of a target protein by at least 10% (e.g., by at least 15%, 20%, 25%, 30%, 35%, 40%, 45%, 50%, 55%, 60%, 65%, 70%, 75%, 80%, 85%, 90%, or even 100% decrease) as compared to the expression or activity of the target protein that is untreated with the inhibitor.

For example, a FraB inhibitor would intoxicate *Salmonella* in the presence of F-Asn. Accordingly, in some embodiments, an inhibitor of FraB reduces the deglycase activity of FraB. Deglycase activity may be inhibited by any mechanism, such as interfering with the active site of FraB, interfering with target recognition, altering the conformation of FraB, interfering with proper intracellular localization of FraB, etc. In some embodiments, an inhibitor of FraB inhibits expression of fraB, such as inhibiting transcription of the fraB gene into mRNA or inhibiting translation of fraB mRNA. In some embodiments, an inhibitor of FraB expression reduces the level of FraB protein by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or 100%. Such inhibitors include antisense oligonucleotides, short interfering RNAs (siRNAs), antibodies, peptides, peptibodies, aptamers, and small molecules. Methods of identifying and exploiting such inhibitors are known in the art. See, e.g., Li et al., 20 Med. Res. Rev. 231 (2007); Supuran, 23 Exp. Op. Thera. Pats. (2013); Cotter et al., 11 Nat. Rev. Microbiol. 95 (2013); Felice et al., 41 Alimentary Pharm. Thera. 26 (2015).

The term "therapeutic agent" as used herein refers to any therapeutically active substance (drug) that is administered to a subject to produce a desired, usually beneficial, effect. The term therapeutic agent includes, e.g., classical low molecular weight therapeutic agents commonly referred to as small molecule drugs; and biologics including antibodies or functionally active portions thereof, peptides, lipids, protein drugs, protein conjugate drugs, fusion proteins, enzymes, nucleic acids, ribozymes, genetic material, and vaccines. A therapeutic agent can also be a pro-drug, which is metabolized into the desired therapeutically active substance at or after administration to a subject. In some aspects, the therapeutic agent is a prophylactic agent. In addition, the therapeutic agent can be pharmaceutically formulated. A therapeutic agent can be an agent activated by other molecules that can be administered, typically orally. For example, a therapeutically effective amount of a drug can inhibit *Salmonella* (lessen the severity of or eliminate the occurrence of *salmonellosis*), prevent or lessen any one of the symptoms of a disorder associated with *Salmonella* as known in the art or described herein. A therapeutically effective amount of a drug may also be one in which any toxic or detrimental effects of the active agent or dosage form are outweighed by the therapeutically beneficial effects.

EXAMPLES

Example 1. Synthesis of Amadori Products

As noted above, F-Asn can be synthesized by organic chemistry. Three fructosyl amino acids were synthesized using amino acids asparagine, lysine, and arginine. See Hodge & Fisher, 2 Meth. Carbohydrate Chem. 99 (1963); Mossine & Mawhinney, 64 Adv. Carbohydr. Chem. Biochem. 291 (2010); Wang et al., 43 J. Mass. Spectrom 262 (2008). The reaction with asparagine was slow because asparagine is sparingly soluble in methanol. By contrast, the reaction with a-Boc-lysine is fast. The reaction with arginine proceeded at an intermediate rate. Additional syntheses of F-Asn have been reported. See, e.g., Stadler et al., 52 J. Agric. Food Chem. 5550 (2004); Wang et al., 2008; Miura et al., 37 Agric. Biol. Chem. 2669 (1973).

The synthesis method of Wang et al., 2008, was further developed after trying a number of different protocols described for other amino acids. See Keil et al., 39 Acta Chem. Scand. B Org. Chem. Biochem. 191 (1985); Krause et al., 216 Eur. Food Res. Technol. 277 (2003); Srinivas et al., 60 J. Agric. Food Chem. 1522 (2012); Weitzel et al., 90 Chem. Ber. 1153 (1957). Wang et al., 2008, describes only a general method, however, and asparagine presents some particular problems with that method, the most important of which is the poor solubility of asparagine in methanol. Bisulfite was added to the reaction mixture to reduce the formation of colored by-products. See Anet, 10 Aust. J. Chem. 193 (1957). Excess glucose was removed by use of a cation-exchange column according to reported methods. See, e.g., Mossine & Mawhinney, 2010. For the synthesis of F-Asn, using methanol as the sole solvent and refluxing for 24 hr resulted in product at approximately 10% to 15% yield, together with recovery of about 90% of the asparagine. Although this yield was low, the starting materials are inexpensive; and the insolubility of asparagine proved advantageous because F-Asn, which is quite soluble in methanol, emerges from the ion exchange column almost free of asparagine. This approach produced a free-flowing, off-white, non-hygroscopic solid product. This approach has also provided large scale, inexpensive syntheses of several Amadori compounds, including F-Asn, F-Lys, F-Arg, F-Asp, and $^{13}$C-labeled F-Asn.

The $^1$H-NMR spectrum of these Amadori compounds was complex because of the equilibrating mixture of alpha- and beta-pyranose and furanose forms (Mossine & Wawhinney, 2010); but integration of the up-field resonances due to the asparagine moiety and the down-field resonances due to the sugar moiety were in the proper ratio. The synthesized material was also characterized by its specific rotation and infrared (IR) spectrum: $[\alpha]^{23}_D$–48° (c=0.1, water) (see Miura et al., 1973; –40°, c=1, water); IR (Nujol): 3350, 3155, 1668, 1633, 1455, 1408, 1080 cm$^{-1}$. Preparations were compared with results in previous reports. Hodge & Fisher, 1963; Miura et al., 1973.

Although fructose-asparagine was synthesized with a reaction carried out in refluxing methanol, yields were somewhat low due to the poor solubility of asparagine in methanol. Prof. Valeri Mossine (Univ. Missouri) suggested a modification of the protocol to avoid this solubility issue by dissolving the components in a small amount of water, adding glycerol (or ethylene glycol), removing the water by rotary evaporation, and heating to carry out the reaction. With this method, all of the components remained in solution, and following the reaction the product can be recovered using propanol precipitation. More specifically, glucose (1 g, 5.5 mmol) and potassium L-aspartate (0.2 g, 1.2 mmol) were dissolved in 3 mL H$_2$O. Glycerol (3 g) was added and the mixture rotary evaporated at 50° C. to remove the water. The viscous homogeneous solution was heated at 60° C. in an un-stoppered flask for 36 hr. Glycerol was removed by dissolution in isopropanol. The precipitated product was dissolved in water and applied to a Dowex-50 column in the hydrogen ion form as above. Mass spectrometry in the negative ion mode showed [fructose aspartic acid]—at m/z 294 (100%) and [aspartic acid]—at m/z 132 (40%). 6-Phosphofructose-aspartate (6-P—F-Asp) was made by this glycerol (or ethylene glycol) procedure because the starting material, glucose-6-phosphate, is insoluble in methanol. The resulting 6-P—F-Asp was characterized by mass spectrometry, and by proton NMR and $^{13}$C NMR.

A similar approach can be used to make F-Asn, 6-PF-Asn, 6-PF-Asp, F-Asp, and further Amadori products. For example, D-glucose (4.1 g, 22 mmol), L-asparagine (0.5 g, 3.7 mmol), NaHSO$_3$ (0.2 g, 2 mmol), and CH$_2$(COOH)$_2$ (0.2 g, 2 mmol) were dissolved with gentle heating in 5 mL H$_2$O. Ethylene glycol (15 mL) was then added to form a homogeneous solution. About 80% of the water was removed by rotary evaporation at ~50° C. The solution was incubated, uncovered, at 70° C. for about 17 hr to yield a pale yellow solution. Longer heating formed brown degradation products that made purification difficult. Ethylene glycol was removed by precipitating the crude product with 1-propanol. The precipitated material was dissolved in H$_2$O and applied to 15 g of a Dowex 50 (200e400 mesh, hydrogen ion form) column (2.5×8 cm). The column was washed with ~500 mL of water; then the product, with some asparagine, was eluted with 0.4 M NH$_3$(aq). The relevant fractions were evaporated at RT to remove excess NH$_3$, minimizing the formation of diglucosyl amine. Product was then further evaporated at 50° C., followed with a final drying by azeotroping with EtOH. A flask pre-treated with Si(CH$_3$)$_2$Cl$_2$ facilitated removal of the product. The yield was about 60% to 70% of off-white free-flowing powder, having an approximate composition F-Asn.0.25 NH$_4^+$ and containing about 10% asparagine as measured by proton NMR using the ratio of the intensity of the 30'-doublet at 54.1 to the integration of the resonances from δ2.7e2.9 due to the beta protons of asparagine and the asparagine residue of F-Asn. Mixtures of asparagine and F-Asn were separated by TLC on silica using 1:1 water:1-propanol, or by methanol extraction of F-Asn. Hansen & Behrman, 431 Carbo. Res. 1 (2016).

As another example of the methanol approach to F-Asn synthesis, glucose (2 g, 11.1 mmol), L-asparagine (1 g, 7.6 mmol), NaHSO$_3$ (1 g, 9.3 mmol), and CH$_2$(COOH)$_2$ (1 g, 9.6 mmol) were suspended in 20 mL MeOH and refluxed for 19 hr, treated with norite, cooled, and the excess asparagine filtered off. Five volumes of acetone were stirred into this solution. The precipitate was filtered by suction and washed with acetone. Alternatively, the methanol can be removed by rotary evaporation. The crude material was dissolved in small volume of water and applied to a 2.5×8 cm column of about 10 g of Dowex 50 in the hydrogen ion form and washed thoroughly with water to remove the excess glucose. F-Asn and a small amount of asparagine were then eluted with dilute ammonia (4 mL conc. ammonium hydroxide in 100 mL water, ca. 0.7 M). F-Asn elutes just as the effluent from the column begins to turn alkaline and it is accompanied by some yellow impurities. The remaining steps are the same as described above. The yield was about 400 mg (18%-22%) of a yellow free-flowing powder. Hansen & Behrman, 431 Carbo. Res. 1 (2016).

Example 2. Preparation of Selective Media

Minimal medium NCE (no carbon essential), supplemented with magnesium and trace metals was used as a minimal medium base to which F-Asn was added. F-Asn is destroyed in autoclaving, so the F-Asn was filter-sterilized. At the outset, one liter of 50×NCE salts was prepared by heating 330 mL of distilled H$_2$O (dH$_2$O) on a stirring block, without allowing the contents to boil. Chemicals were dissolved one-at-a-time in the following order, allowing each to dissolve completely before adding the next: 197 g KH$_2$PO$_4$; 323 g K$_2$HPO$_4$.3H$_2$O (246.6 g for anhydrous); and 175 g NaNH$_4$HPO$_4$.4H$_2$O. After the salts were completely dissolved, the volume was adjusted to 1000 mL with dH$_2$O. This 50× concentrate can then be filter-sterilized or autoclaved. In theory, nothing should grow in the concentrated salts without a carbon source; however, one may plate a few drops of the stock solution, if it is not autoclaved or filtered, to ensure sterility. The 50× concentrate should be stored at 4° C. or otherwise refrigerated to limit loss of ammonium ions as ammonia. Additionally, a solution of 10,000× trace elements was also prepared, the stock solution containing 30 mM CaCl$_2$, 10 mM ZnSO$_4$, 4.5 mM FeSO$_4$, 20 mM Na$_2$Se$_2$O$_3$, 20 mM Na$_2$MoO$_4$, 200 mM MnSO$_4$, 10 mM CuSO$_4$, 300 mM CoCl$_2$, and 10 mM NiSO$_4$. This solution can also be autoclaved or filter-sterilized, and stored at room temperature. See Price-Carter et al., 2001. Finally, a sterile solution of 1M MgSO$_4$ was prepared by dissolving 24.65 g MgSO$_4$ in dH$_2$O to a final volume of 100 ml, and autoclaving. Filter-sterilization is also appropriate, and this stock solution can be stored at room temperature.

One liter of minimal medium NCE was then prepared by mixing 20 mL of the 50×NCE salts, 1 mL of the trace elements concentrate, and 1 mL of 1M MgSO$_4$. F-Asn was included at a concentration of 5 mM. Sterile dH$_2$O was used to adjust the volume to 1000 mL. The NCE minimal medium was not—and should not be—autoclaved, even before addition of F-Asn, because the salts may precipitate; so either the components must be sterilized before mixing, or the entire solution can be filter-sterilized. Growth of wild-type and fraB mutant *Salmonella* in NCE with glucose or F-Asn is compared in FIG. 3.

M9 Minimal medium containing F-Asn as the sole nutrient was made by first preparing a stock solution of 10×M9 salts (500 mL: 30 g $Na_2HPO_4$ (anhydrous), 15 g $KH_2PO_4$, 2.5 g NaCl, and 5.0 g $NH_4Cl$, distilled $H_2O$ ($dH_2O$), adjusted to pH 7.4 with NaOH, then autoclaved).

About 100 mL of M9 Minimal media plus F-Asn was prepared by mixing 90 mL $dH_2O$, 10 mL 10×M9 salts, 200 µL of 1 M $MgSO_4$ (2 mM final), 10 µL of $CaCl_2$ (0.1 mM final), 10 µL of 10,000× trace elements (prepared as above), and 1 µL of 1M vitamin B1 (thiamine). The M9 Minimal media was autoclaved. F-Asn is heat labile, so F-Asn was filter-sterilized and then added at a concentration of 5 mM after the M9 base medium had cooled to room temperature.

Medium containing 1.5% Bacto Agar (Difco) can be used as solid F-Asn nutrient medium. Bacteria in natural circumstances, such as biological or food samples, are almost always found as mixtures of many species. For most purposes, it is necessary to isolate the various organisms in pure culture before they can be identified and studied. A typical technique for this purpose is "streaking out" on the surface of a solid nutrient medium, the principle being that a single organism, physically separated from others on the surface of the medium (a colony-forming-unit), will multiply and give rise to a localized colony of descendants. Thus, this technique is used to isolate a pure strain from a single species of microorganism, often bacteria. Further samples can then be taken from the resulting colonies and a microbiological culture can be grown on a new plate so that the organism can be identified, studied, or tested. Thus, a *Salmonella*-selective solid F-Asn nutrient medium allows the isolation of a single pure strain of *Salmonella* from a given sample.

Another minimal medium consists of (pH 7.2-pH 7.4) contains: 2.6 g/L $(NH4)_2SO_4$, 1.0 g/L $NH_4Cl$, 0.5 g/L NaCl, 15.0 g/L $Na_2HPO_4.12H_2O$, 3.0 g/L $KH_2PO_4$, 50.0 mg/L $FeCl_3.6H_2O$, 1.8 mg/L $ZnSO_4.7H_2O$, 1.8 mg/L $CuSO_4.5H_2O$, 1.2 mg/L $MnSO_4.H_2O$, 1.8 mg/L $CoCl_2.6H_2O$, 2.0 mM $MgSO_4$, 0.2 mM $CaCl_2$, 0.3 µM thiamine.HCl, and, optionally, 0.003 g/L $FeSO_4$. The carbon source for this medium is 5 mM F-Asn, rather than the standard 20 mM glucose. The components are prepared and sterilized separately, then mixed aseptically as follows: (1) phosphates, sodium chloride, and ammonium; (2) iron chloride; (3) copper, zinc, cobalt, and manganese salts; (4) magnesium salt; (5) calcium salt; and (6) F-Asn.

Example 3. Bacterial Growth and Construction of *Salmonella* Mutants

Bacteria were grown in Luria-Bertani (LB) culture medium, e.g., in LB broth or on LB agar plates (EM Science), unless otherwise noted. LB medium typically comprises 10 g Bacto tryptone; 5 g Yeast extract; 10 g NaCl; pH 7.5 Water qsf 1,000 g. The minimal medium used was NCE (no carbon E) containing trace metals. See Example 2; Price-Carter et al., 2001. Chloramphenicol (cam) (30 mg/ml), streptomycin (strep) (200 mg/ml), or kanamycin (kan) (60 mg/ml) were added when appropriate. F-Asn was either synthesized, as described in Example 1, or purchased from Toronto Research Chemicals (catalog # F792525).

Anaerobic growth was performed in a Bactron 1 anaerobic chamber containing 90% N2, 5% CO2, and 5% H2 (Shel Lab).

Strains and plasmids used are described in Table 2:

TABLE 2

Bacterial strains and plasmids

| Strain or plasmid | Genotype or description |
|---|---|
| 14028 | wild-type *Salmonella enterica* serovar *Typhimurium* |
| ASD6000 | MA59 fraB1::kan + pASD5006 (amp$^r$, fraR$^+$, fraBDAE$^+$) |
| ASD6010 | MA59 fraB1::kan + pWSK29 (amp$^r$) |
| ASD6040 | CS1032fraB4::kan + pASD5006 (amp$^r$) |
| ASD6090 | IR715 + pWSK29 (amp$^r$) |
| IR715 | 14028 nal$^r$ |
| JLD400 | wild-type *Enterbacter cloacae* isolated from a lab. mouse |
| JLD1214 | 14928 IG (pagC-STM14_1502)::cam |
| MA43 | IR715 phoN1::aadA |
| MA45 | IR715 sirA2::kan |
| MA59 | IR715 fraB1::kan |
| CS1032 | IR715 fraB4::kan |
| MA4301 | 14028 Δ(avrA-invH)1 ssaK::kan |
| MA4310 | MA43 ttrA1::cam |
| MA5900 | 14028 Δ(avrA-invH)1 ssaK::kan fraB1::cam |
| MA5910 | IR715 fraB1::kan ttrA1::cam |
| pASD5006 | pWSK29 fraRBDAE + amp$^r$ |
| pWSK29 | pSC101 cloning vector amp$^r$ |
| pCP20 | cI857 λPR flp pSC101 oriTS (amp$^r$, cam$^r$) |
| pKD3 | FRT-cam-FRT oriR6K (amp$^r$) |
| pKD4 | FRT-kan-FRT oriR6K (amp$^r$) |

*Enterobacter cloacae* strain JLD400 was isolated in by plating fecal samples from a conventional BALB/c mouse onto LB agar plates. This particular *E. cloacae* isolate was chosen because it is easy to culture and genetically manipulable (the strain can be electroporated, maintains ColE1-based plasmids, and can act as a recipient in RP4-mediated mobilization of a suicide vector used to deliver mTn5-luxCDABE). The species identification was performed using a Dade Microscan Walkaway 96si at the Ohio State University medical center. Additionally, genomic DNA sequences have been obtained that flank mTn5-luxCDABE insertions in JLD400 and these DNA sequences match the draft genome sequence of *E. cloacae* NCTC 9394.

A transposon mutant library was constructed in *S. enterica* serovars *Typhimurium* strain 14028. EZ-Tn5<T7/kan> transposomes from Epicentre Technologies were delivered to *Salmonella* by electroporation. This transposon encodes kanamycin resistance and has a T7 RNA Polymerase promoter at the edge of the transposon pointed outward. The resulting library contains between 190,000 and 200,000 independent transposon insertions and is referred to as the JLD200k library. The insertion points of this library have been determined previously by next-generation sequencing. Canals et al., 13 BMC Genomics 212 (2012). It is estimated that approximately 4400 of the 4800 genes in the *Salmonella* genome are non-essential with regard to growth on LB agar plates. Id. Therefore, the JLD200k library is saturated with each gene having an average of forty-three independent transposon insertions.

A FRT-kan-FRT or FRT-cam-FRT cassette, generated using PCR with the primers listed in Table 3 and pKD3 or pKD4 as template, was inserted into each gene of interest (replacing all but the first ten and last ten codons) using lambda red mutagenesis of strain 14028+pKD46 followed by growth at 37° C. to remove the plasmid. Datsenko & Warner, 97 PNAS 6640 (2000). A temperature sensitive plasmid encoding FLP recombinase, pCP20, was then added to each strain to remove the antibiotic resistance marker. Id.

The pCP20 plasmid was cured by growth at 37° C. A fraB4::kan mutation was constructed using primers BA2552 and BA2553 (Table 3). A FRT-cam-FRT cassette was placed in an intergenic region downstream of pagC using primers BA1561 and BA1562 (deleting and inserting between nucleotides 1342878 and 1343056 of the 14028 genome sequence (accession number NC_016856.1) (Table 3).

mice in the presence or absence of *E. cloacae* strain JLD400. Four mice were inoculated intragastrically (i.g.) with $10^7$ cfu of *E. cloacae* strain JLD400 that had been grown overnight in LB shaking at 37° C. After 24 hours, these mice and an additional four germ-free mice, were inoculated with $10^7$ cfu of the JLD200k library that had been grown overnight in shaking LB kan at 37° C. Prior to inoculation of the mice,

TABLE 3

Oligonucleotides used

| Gene targeted | Primer name | Description | Sequence |
|---|---|---|---|
| pagC | BA1561 | Used for lambda red mutagenesis in which the cat (cam$^r$) gene was placed | CTTCTTTACCAGTGACACGTACCTGCCTGTCT TTTCTCTTGTGTAGGCTGGAGCTGCTTCG (SEQ ID NO: 23) |
| pagC | BA1562 | downstream of pagC in a neutral site using pKD3 as PCR template. | CGAAGGCGGTCACAAAATCTTGATGACATTGT GATTAACATATGAATATCCTCCTTAG (SEQ ID NO: 24) |
| fra island | BA2228 | Used for amplifying the fra island and cloning it into a | CGCAGAATCTATCCGTCCGACAACGAAC (SEQ ID NO: 25) |
| fra island | BA2229 | complementation vector, resulting in pASD5006. | GCAGGTTAAGGCTCTCCGTAAAGGCCAATC (SEQ ID NO: 26) |
| fraB | BA2552 | Used for lambda red mutagenesis in which the aph (kan$^r$) gene was placed within | CCTGATGTAATTAATATTCCACTTTCCACATA TAGCGGCGCATATGAATATCCTCCTTAG (SEQ ID NO: 27) |
| fraB | BA2553 | the fraB gene using pKD4 as PCR template. | AGAGGAAAGCATGATGGGTATGAAAGAGACAG TTAGCAATGTGTAGGCTGGAGCTGCTTC (SEQ ID NO: 28) |

Example 4. Animal Experiments and Mouse-Derived Bacterial Strains

All animal work was performed in accordance with the protocols approved by the Ohio State University Institutional Animal Care and Use Committee (OSU 2009A0035). The IACUC ensures compliance of the protocols described herein with the U.S Animal Welfare Act, Guide for Care and Use of Laboratory Animals and Public Health Service Policy on Humane Care and Use of Laboratory Animals. Human fecal material was obtained from an anonymous healthy donor at the Ohio State University fecal transplant center in accordance with the protocol approved by our Institutional Review Board (OSU 2012H0367).

Germ-free C57BL/6 mice were obtained from Balfour Sartor of the NIH gnotobiotic resource facility at the University of North Carolina, and from Kate Eaton at the University of Michigan. Germ-free Swiss Webster mice were obtained from Taconic Farms. The mice were bred and maintained under germ-free conditions in sterile isolators (Park Bioservices). Periodic Gram-staining, 16s PCR, and pathology tests performed by the Ohio State University lab animal resources department and by the present inventors were used to confirm that the mice contained no detectable microorganisms. Conventional C57BL/6 mice were obtained from Taconic Farms. C57BL/6 mice that were heterozygous for the Nramp1 gene were generated by breeding the standard Nramp1$^{-/-}$ mice from Taconic Farms with C57BL/6 Nramp1$^{+/+}$ mice from Greg Barton. Arpaia et al., 144 Cell 675 (2011). IL10 knockout mice (B6.129P2-IL10$^{tm1Cgn}$/J) were obtained from Jackson Laboratory. Germ-free Swiss Webster mice were "humanized" by intragastric inoculation of 200 μL of human feces obtained from an anonymous healthy donor from the OSU fecal transplant center.

For transposon site hybridization (TraSH), a JLD200k transposon mutant library was grown in germ-free C57BL/6 the library was spiked with an additional mutant, JLD1214, at a 1:10:000 ratio. This mutant contains a chloramphenicol resistance (cam$^r$) gene at a neutral location in the chromosome in the intergenic region downstream of pagC. See Gunn et al., 68 Infect. Immun. 6139 (2000).

After inoculation of mice with the spiked library, the inoculum was dilution plated to quantitate the kanamycin resistant (kan$^r$) *Salmonella* library members and the cam$^r$ spike strain. The remainder of the inoculum was pelleted and saved as the "input" for hybridization to microarrays. After 24 hours of infection with the JLD200k library, the mice were euthanized and organs were harvested (small intestine, cecum, large intestine, and spleen). One germ-free mouse died prior to organ harvest and was not used. All samples were homogenized and dilution plated to determine *Salmonella* counts. The remainder of the homogenate was added to 25 ml LB kan and grown overnight with shaking at 37° C. to recover the library members. Each culture was then pelleted and frozen as a potential "output" sample for microarray analysis.

The kan$^r$ and cam$^r$ colony counts recovered from each organ indicated that the spike ratio of 1:10,000 was maintained in the intestinal samples but not in the spleen samples. This indicates that the library underwent a population bottleneck on the way to the spleen so microarray analysis of spleen samples would not be informative. The cecum samples were chosen for microarray analysis. There was one "input" sample for all arrays. There were seven separate "output" samples for the arrays; four from the cecums of *Enterobacter*-associated mice and three from germ-free mice. The output from each mouse was compared to the input on a single array. S single "in vitro" array experiment was also conducted in which the JLD200k library was grown in the presence of *Enterobacter* in liquid LB broth shaking at 37° C.

Genomic DNA was isolated from the input and output bacterial pellets. The purity and concentration of the DNA samples was assessed using a NANODROP spectrophotometer and the quality of the DNA was assessed via agarose gel electrophoresis. All seven samples had high quality intact genomic DNA. The DNA was digested using a restriction endonuclease (RsaI). Labeled RNA transcripts were obtained from the T7 promoter by in vitro transcription. A two-color hybridization strategy was employed. RNA transcripts from the output samples were fluorescently labeled with Cyanine-5 (Cy5, red), while the input sample was labeled with Cyanine-3 (Cy3, green). Equal molar concentrations of the output and input sample were combined and hybridized to genome-wide tiling microarrays printed commercially by Agilent Technologies. Agilent's SUREPRINT technology employs phosphoramadite chemistry in combination with high performance Hewlett Packard inkjet technology for in situ synthesis of 60-mer oligonucleotides. Agilent eArray, an easy-to-use, web-based application, was used to synthesize the arrays used by Chaudhuri et al., that completely tiled both the sense and anti-sense strands of the Salmonella SL1344 genome (AMADID 015511). See Chaudhuri et al., 5 PLoS Pathog e1000529 (2009). Each slide contained 2 arrays, each array with 105,000 features, densely tiling the entire genome. The strain of Salmonella used in the experiments was 14028, and its genome sequence was only recently published (GenBank Nucleotide Accession CP001363 (complete genome) and CP001362 (plasmid)). As such, each of the 60-mer probes described elsewhere (Chaudhuri et al., 2009) were mapped to the 14028 genome using BLAST, and then annotated with any open reading frames (ORFs) spanned by the probe. A total of 96,749 probes were mapped to the 14028 genome, with a median gap between each probe of 35 nucleotides on both strands.

After purification, the labeled samples were denatured and hybridized to the array overnight. Microarray slides were then washed and scanned with an Agilent G2505C Microarray Scanner, at 2 mm resolution. Images were analyzed with Feature Extraction 10.5 (Agilent Technologies, CA). Median foreground intensities were obtained for each spot and imported into the mathematical software package "R", which was used for all data input, diagnostic plots, normalization and quality checking steps of the analysis process using scripts developed specifically for this analysis. In outline, the intensities were not background corrected as this has been shown to only introduce noise. The dataset was filtered to remove positive control elements and any elements that had been flagged as bad, or not present in the 14028 genome. Using the negative controls on the arrays, the background threshold was determined and all values less than this value were flagged. Finally, the Log 2 ratio of output Cy5/input Cy3 (red/green) was determined for each replicate, and the data was normalized by the loess method using the LIMMA (Linear models for microarray data) package in "R" as described elsewhere. See Smyth et al., 31 Methods 265 (2003); Smyth et al., 224 Methods Mol. Biol. 111 (2003).

Complete statistical analysis was then performed in "R". Insertion mutants where the ORF is essential for survival are selected against, and thus a negative ratio of Cy5/Cy3 (red/green) is observed in the probes adjacent to the insertion point, resulting from higher Cy3 (green) signal from the input. Conversely, insertion mutants that were advantageous to growth in the output samples would have a positive ratio, resulting from the higher Cy5 (red) signal in the output. Mutants having no effect on growth would have equal ratios in both the output and input samples (yellow).

The TraSH data from germ-free mice and germ-free mice monoassociated with E. cloacae. A normalized Log 2 ratio of output/input hybridization intensity was determined for each replicate. Insertion mutants where the ORF is essential for survival were selected against, and thus yielded a negative ratio in the probes adjacent to the insertion point. Conversely, insertion mutants that were advantageous to growth in the output samples yielded a positive ratio. The average ratio for all probes and all replicates for each locus are shown in a spreadsheet for germ-free mice and germ-free mice monoassociated with E. cloacae. The difference column shows the difference of the ratios for that locus between the two mouse groups to facilitate the identification of differentially required genes. The spreadsheet has two tabs, one sorted by locus tag and one sorted by difference. The spreadsheet is available for free via hyperlink in the on-line version of Ali et al., Fructose-Asparagine is a Primary Nutrient during Growth of Salmonella in the Inflamed Intestine, 10 PLOS Pathog. e1004209 (2014); see also PCT/US15/60141.

Example 5. Competition Assays and Complementation Assays

Competition assays were performed in which a mutant strain was mixed in a 1:1 ratio with an isogenic wild-type and inoculated by the intragastric (i.g.) or intraperitoneal (i.p.) route to mice. Fecal samples, intestinal sections, spleen and liver were recovered at specific times post-infection, homogenized and plated on selective plates. The wild-type and mutant strains were differentiated by antibiotic resistance. The competitive index was calculated as CI=(cfu of mutant recovered/cfu w.t. recovered)/(cfu mutant input/cfu w.t. input). If the mutant is defective compared to the wild-type it will have a CI of less than 1.

For complementation assays, the fra island was PCR-amplified from purified Salmonella strain 14028 genomic DNA with primers BA2228 and BA2229 using Phusion polymerase (New England Biolabs). The PCR product was cloned into pPCR-Blunt II-TOPO (Invitrogen). The resulting clones were digested with EcoRI (New England Biolabs), run on an agarose gel, and the 8.6 kbp fra fragment was gel purified (Qiagen). This purified DNA fragment was ligated overnight at 4° C. into EcoRI-digested pWSK29 using T4 DNA ligase (New England Biolabs). The ligation reaction was transformed into DH5a and plated on LB containing ampicillin at 37° C. The resulting plasmid, pASD5006, or the vector control pWSK29, were electroporated into the appropriate strains.

Example 6. DNA and Amino Acid Sequences of the Fra Locus

In some embodiments, the DNA of the fra locus is the fra promoter, which is located in the fra locus beginning at the nucleotide right after the stop codon of fraR and ending at the nucleotide right before the start codon of fraB, the fra promoter having the following DNA sequence:

```
                                              (SEQ ID NO: 1)
TGTCAGCATTACGCTAACGAAGAGCAGGCTGAATCGGGATCCAGATCGCG

GATCCCGATTTTTTTTGGTTTCCATCTTGATCAAATGTCTTTAAATGTCA

TATAAAAATAATAATACATTATGAGTCATTTATGGCGAATCCTCGCCTGT

ATCATTG.
```

In some embodiments, the fra promoter has a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:1.

In some embodiments, the fraA gene has the following DNA sequence:

(SEQ ID NO: 2)
ATGTTTTGGACGGAATTATGTTTTATCCTTGTGGCCCTGATGATAGGCGC

CAGGATCGGCGGCGTATTTTTAGGGATGGTCGGCGGGTTAGGCGTCGGCG

TGATGGTTTTTATTTTTGGCCTGACGCCTTCTACGCCACCGATTGATGTT

ATTCTGATTATTCTTTCTGTTGTCCTGGCGGCCGCTTCTTTACAGGCCTC

CGGCGGGCTGGATTTACTGGTCAAACTGGCGGAAAAAATTCTGCGTCGCC

ACCCGCGTTACATTACGTTATTAGCGCCGTTTATCTGTTATATCTTCACT

TTTATGTCAGGAACGGGGCATGTCGTTTATAGCTTGCTACCGGTTATTTC

TGAAGTCGCACGGGATTCAGGTATTCGACCGGAACGTCCTTTATCTATTT

CCGTTATCGCATCGCAACAGGCGATCACCGCCAGTCCTATATCTGCCGCC

ATGGCGGCGATGATTGGTTTAATGGCGCCGTTGGGCGTCTCTATTTCAAC

CATTATGATGATTTGCGTGCCCGCCACGTTAATCGGCGTAGCGATGGGGG

CAATAGCGACCTTTAATAAAGGAAAAGAGTTAAAAGACGATCCGGAATAT

CAACGTCGGCTTGCTGAAGGGTTAATTAAACCTGCGCAGAAAGAAAGTAA

AAATACGGTGGTCACTTCGCGCGCCAAATTGTCGGTGGCGTTATTTCTGA

CCAGTGCGATCGTTATCGTTCTGTTAGGACTGATTCCGGCGCTGCGGCCC

ATGGTGGAAACAGCGAAAGGGCTACAACCGCTTTCGATGTCCGCCGCTAT

CCAGATTACGATGCTCTCTTTTGCCTGCCTGATTGTGTTGTTATGCCGAC

CGCAGGTCGATCAAATTATCAGCGGTACGGTATTTCGGGCGGGCGCGCTG

GCGATTGTCTGCGCCTTCGGCCTGGCCTGGATGAGTGAGACGTTCGTGAA

TGGTCATATCGCGTTGATTAAGGCAGAAGTGCAAACTCTATTGCAACAGC

ATACCTGGCTTATCGCCATTATGATGTTTTTTGTGTCCGCTATGGTCAGC

AGCCAGGCGGCAACGACGTTAATTCTGTTGCCGCTGGGGCTGGCGTTAGG

GTTGCCCGCTTATGCATTAATCGGCTCCTGGCCTGCCGTTAACGGCTATT

TCTTTATTCCGGTGGCGGGGCAGTGTCTGGCGGCGCTGGCGTTTGACGAT

ACCGGTACGACGCGTATTGGCAAATATGTGCTTAACCATAGTTTTATGCG

TCCGGGATTAGTTAACGTGATTGTCTCGGTCATTGTCGGGCTGTTAATAG

GAAAAATGGTTCTGGCCTGA.

In some embodiments, the fraA gene has a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:2.

In some embodiments, the fraA gene encodes a protein having this amino acid sequence:

(SEQ ID NO: 3)
MFWTELCFILVALMIGARIGGVFLGMVGGLGVGVMVFIFGLTPSTPPIDV

ILIILSVVLAAASLQASGGLDLLVKLAEKILRRHPRYITLLAPFICYIFT

FMSGTGHVVYSLLPVISEVARDSGIRPERPLSISVIASQQAITASPISAA

MAAMIGLMAPLGVSISTIMMICVPATLIGVAMGAIATFNKGKELKDDPEY

QRRLAEGLIKPAQKESKNTVVTSRAKLSVALFLTSAIVIVLLGLIPALRP

MVETAKGLQPLSMSAAIQITMLSFACLIVLLCRPQVDQIISGTVFRAGAL

AIVCAFGLAWMSETFVNGHIALIKAEVQTLLQQHTWLIAIMMFFVSAMVS

SQAATTLILLPLGLALGLPAYALIGSWPAVNGYFFIPVAGQCLAALAFDD

TGTTRIGKYVLNHSFMRPGLVNVIVSVIVGLLIGKMVLA.

In some embodiments, the fraA gene encodes a protein having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:3.

In some embodiments, the fraB gene has the following DNA sequence:

(SEQ ID NO: 4)
ATGATGGGTATGAAAGAGACAGTTAGCAATATTGTGACCAGCCAGGCAGA

GAAAGGAGGCGTTAAACACGTCTATTACGTGGCGTGCGGCGGTTCTTATG

CGGCGTTCTATCCGGCGAAAGCATTTTTAGAAAAAGAAGCGAAAGCGTTG

ACTGTCGGTCTGTATAACAGCGGAGAATTTATTAACAACCCGCCGGTAGC

GCTGGGAGAAAATGCCGTTGTGGTTGTCGCCTCCCACAAAGGTAATACGC

CAGAGACAATTAAAGCGGCTGAAATCGCCCGTCAGCACGGCGCGCCGGTC

ATTGGTTTAACCTGGATAATGGATTCACCGTTGGTGGCGCATTGCGACTA

TGTGGAAACGTACACGTTTGGCGACGGTAAAGATATTGCCGGAGAGAAAA

CGATGAAAGGCCTGCTGAGTGCGGTCGAACTGCTCCAGCAGACGGAAGGG

TATGCGCACTACGACGATTTTCAGGATGGCGTCAGCAAAATCAACCGTAT

CGTCTGGCGCGCTTGCGAGCAGGTAGCGGAGCGTGCGCAGGCGTTCGCGC

AGGAATATAAAGACGATAAAGTCATTTATACCGTCGCCAGCGGCGCGGGC

TATGGCGCAGCCTACCTACAGAGCATCTGCATCTTTATGGAAATGCAATG

GATACATTCCGCCTGTATTCATAGCGGTGAGTTTTTCCACGGGCCGTTTG

AAATTACCGATGCGAATACGCCTTCTTCTTCCAGTTTTCCGAGGGCAAT

ACGCGGCGGTGGATGAACGCGCGTTAAACTTCCTGAAAAAATATGGCCG

CCGGATTGAAGTTGTCGATGCGAAAGAACTGGGGCTATCGACCATTAAAA

CCACGGTTATTGATTACTTTAACCACTCTCTCTTTAATAACGTTTATCCC

GTTTACAATCGGGCGTTAGCTGAGGCGCGTCAGCATCCGTTAACGACGCG

CCGCTATATGTGGAAAGTGGAATATTAA.

In some embodiments, the fraB gene has a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:4.

In some embodiments, the fraB gene encodes a protein having the following amino acid sequence:

(SEQ ID NO: 5)
MGMKETVSNIVTSQAEKGGVKHVYYVACGGSYAAFYPAKAFLEKEAKALT

VGLYNSGEFINNPPVALGENAVVVVASHKGNTPETIKAAEIARQHGAPVI

-continued

```
GLTWIMDSPLVAHCDYVETYTFGDGKDIAGEKTMKGLLSAVELLQQTEGY

AHYDDFQDGVSKINRIVWRACEQVAERAQAFAQEYKDDKVIYTVASGAGY

GAAYLQSICIFMEMQWIHSACIHSGEFFHGPFEITDANTPFFFQFSEGNT

RAVDERALNFLKKYGRRIEVVDAKELGLSTIKTTVIDYFNHSLFNNVYPV

YNRALAEARQHPLTTRRYMWKVEY.
```

In some embodiments, the fraB gene encodes a protein having an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:5.

In some embodiments, the fraD gene has the following DNA sequence:

```
(SEQ ID NO: 6)
ATGAGCATCAGCGTATTGGGTATTGGCGACAACGTTGTCGATAAATACCT

GCATTCCGGCATCATGTACCCCGGCGGTAATGCATTAAATTTTGCTGTCT

ATGCGAAATTAGCAGACATCCCCAGCGCGTTTATGGGGGCGTTTGGCAAT

GACGACGCCGCGCAGCACGTACAGGATGTATTACACCAGCTACAGATAGA

CATCTCTCACAGCCGCCATTATACCGGCGAAAATGGGTATGCCTGTATCC

GTCTCTCGCATGGCGATCGGCAATTTGTCGCCAGCAACAAAAACGGCGTA

TTGCGGGAACATCCTTTTAGTCTGTCTGACGACGATCTTCGCTATATATC

ACAATTTACCTTAGTCCATTCCAGTATTAACGGCCACCTGGAATCGGAAC

TGGAGAAAATTAAACAACAAACCGTCTTACTCTCTTTTGATTTTTCCGGG

CGCGGTACAGACGACTATTTTGAAAAGGTATGCCCGTGGGTAGATTACGG

ATTTATCTCCTGTAGCGGGTTATCGCCAGATGAAATCAAAGTAAAACTCA

ATAAACTTTATCGTTATGGCTGTCGGCATATTATTGCCACCTGCGGGCAT

GAAAAAGTTTATTATTTTTCCGGCGCGGATTATCTGGAGTGGCAACCTGC

TTATATCGAACCTGTCGATACGCTGGGCGCAGGCGACGCCTTCTTAACCG

GTTTTTTGCTTTCCATTTTGCAATCGGGTATGGCGGAACCCGATAAAGAA

AGCGTGTTACGCGCCATGCGGCAGGGCGGGAAATCGGCGGCGCAGGTGTT

ATCTCATTACGCGCATTTGGTTTTGGTAAACCGTTTGCACAATAG.
```

In some embodiments, the fraD gene has a DNA sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:6.

In some embodiments, the fraD gene encodes a protein having the following amino acid sequence:

```
(SEQ ID NO: 7)
MSISVLGIGDNVVDKYLHSGIMYPGGNALNFAVYAKLADIPSAFMGAFGN

DDAAQHVQDVLHQLQIDISHSRHYTGENGYACIRLSHGDRQFVASNKNGV

LREHPFSLSDDDLRYISQFTLVHSSINGHLESELEKIKQQTVLLSFDFSG

RGTDDYFEKVCPWVDYGFISCSGLSPDEIKVKLNKLYRYGCRHIIATCGH

EKVYYFSGADYLEWQPAYIEPVDTLGAGDAFLTGFLLSILQSGMAEPDKE

SVLRAMRQGGKSAAQVLSHYGAFGFGKPFAQ.
```

In some embodiments, the fraD encodes a protein having an amino acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:7.

In some embodiments, the fraE gene has the following DNA sequence:

```
(SEQ ID NO: 8)
ATGAAAATTAGAGTTTTCATGGCCACCGTGTTGCTGCTCATCAGCCACTG

TGTATTTAGCACAACGTCACTACCGCATATTGTTATTCTCGCGACAGGTG

GTACTATCGCCGGGACGGCAGCCAATAATACGCAAACCGCCGGATATAAA

TCTGGTGAACTTGGCGTGCAAACATTAATAAATGCCGTGCCGGAAATGAA

TAATATCGCTCGCGTTGACGGCGAGCAGGTGGCGAATATTGGTAGCGAAA

ATATGACCAGCGATATCATCCTGAAACTTTCACAGAAGGTGAATGCGTTA

TTGGCGCGGGACGATGTTGACGGTGTGGTTATTACTCATGGCACTGACAC

GCTCGATGAAACCGCCTACTTTCTTAATTTGACCGTGAAAAGCGACAAAC

CGGTGGTGTTTACCGCTGCAATGCGGCCCGCGTCGGCAATCAGCGCCGAT

GGCGCAATGAACCTGCTGGAAGCGGTCACGGTGGCTGCTGACCCGAATGC

GAAGGGACGCGGTGTGATGGTGGTTTTAAACGATCGTATTGGTTCGGCGC

GCTTTGTGACGAAAACTAATGCCACGACTCTGGATACCTTTAAAGCGCCG

GAAGAGGGCTATCTGGGGGTCATCGTTAATGGTCAGCCACAGTTCGAAAC

GCGGGTGGAAAAAATTCATACCCTGCGATCTGTTTTTGACGTACGTAATA

TCAAAAAATTACCCAATGTGGTGATTATTTACGGCTATCAGGACGACCCG

GAATATATGTATGATGCGGCGATCGCCCATCACGCGGACGGTATTATTTA

TGCCGGAACCGGCGCAGGTTCGGTCTCGGTACGCAGCGACGCGGGGATTA

AAAAAGCGGAGAAAGCCGGGATTATCGTGGTGCGCGCTTCCCGCACCGGA

AACGGCGTCGTACCGTTGGATAAAGGGCAGCCAGGGCTGGTGTCTGACTC

GCTCAACCCGGCGAAGGCGCGAGTCTTGCTGATGACGGCATTAACTCAGA

CGCGTAATCCGGAACTGATCCAGAGTTATTTCAGTACGTATTAA.
```

In some embodiments, the fraE gene has a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:8.

In some embodiments, the fraE gene encodes a protein having the following amino acid sequence:

```
(SEQ ID NO: 9)
MKIRVFMATVLLLISHCVFSTTSLPHIVILATGGTIAGTAANNTQTAGYK

SGELGVQTLINAVPEMNNIARVDGEQVANIGSENMTSDIILKLSQKVNAL

LARDDVDGVVITHGTDTLDETAYFLNLTVKSDKPVVFTAAMRPASAISAD

GAMNLLEAVTVAADPNAKGRGVMVVLNDRIGSARFVTKTNATTLDTFKAP

EEGYLGVIVNGQPQFETRVEKIHTLRSVFDVRNIKKLPNVVIIYGYQDDP

EYMYDAAIAHHADGIIYAGTGAGSVSVRSDAGIKKAEKAGIIVVRASRTG

NGVVPLDKGQPGLVSDSLNPAKARVLLMTALTQTRNPELIQSYFSTY.
```

In some embodiments, the fraE gene encodes an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:9.

In some embodiments, the fraR gene has the following DNA sequence:

(SEQ ID NO: 10)
ATGATCGAGCAACCCGACAGTAAAAGCGCCAAACCGCTTTATAAGCAGCT

TGAAGCCGCCTTAAAAGAGGCTATTGCGCGTGGAGAGTATAAACCAGGCC

AGCAGATCCCGACGGAAAATGAACTGAGCGTGCGCTGGCAGGTGAGCAGG

GTCACGGTCCGTAAGGCGCTGGATGCGCTGACGCGTGAAAATTTGCTGAC

CCGTGTCTCCGGCAAAGGCACCTTTGTCTCTGGTGAGAAATTTCAGCGCA

GCATGACCGGCATCATGAGTTTCAGCGAGTTATGCCAGTCCCAGGGACGT

CGCCCGGGGTCACGCACCATCAAATCCGTTTTTGAATCGGTAGACGATGA

GACAAAAGCGTTACTGAATATGAACGATGGCGAAAAAGCGGTCGTCATTG

AACGTATCCGCTATGCCGACGATGTGGCGGTATCGCTGGAAACCGTACAT

CTTCCCCCACGTTTTGCGTTTTTGCTGGACGAAGATCTTAATAATCACTC

TTTGTATGAATGCTTACGCGAGAAATACCATTTATGGTTTACCCACTCCC

GTAAGATGATCGAACTGGTTTATGCCAGCTTTGAAGTCGCCCATTATCTT

GGCGTCAACGAGGGTTATCCGCTGATCCTGATAAAAAGTGAAATGATTGA

TAACAAAGGAGAACTCTCCTGCGTTTCGCAACAGTTGATTGTCGGCGATA

AAATACGGTTTACCGTATGA.

In some embodiments, the fraR gene has a nucleic acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:10.

In some embodiments, the fraR gene encodes a protein having the following amino acid sequence:

(SEQ ID NO: 11)
MIEQPDSKSAKPLYKQLEAALKEAIARGEYKPGQQIPTENELSVRWQVSR

VTVRKALDALTRENLLTRVSGKGTFVSGEKFQRSMTGIMSFSELCQSQGR

RPGSRTIKSVFESVDDETKALLNMNDGEKAVVIERIRYADDVAVSLETVH

LPPRFAFLLDEDLNNHSLYECLREKYHLWFTHSRKMIELVYASFEVAHYL

GVNEGYPLILIKSEMIDNKGELSCVSQQLIVGDKIRFTV.

In some embodiments, the fraR gene encodes an amino acid sequence having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NO:11.

Example 7. F-Asn Concentrations in Mouse Chow and Mouse Intestinal Contents

F-Asn was measured in mouse chow and mouse intestinal contents using liquid chromatography coupled with mass spectrometry (MS). An Agilent 1200 series HPLC system equipped with an autosampler was coupled to the quadrupole-ion-trap mass spectrometer via an ESI ion source. Selected reaction monitoring (SRM) transitions for unlabeled and $^{13}$C-labeled F-Asn (uniformly labeled in the sugar), and unlabeled and $^{15}$N-labeled asparagine were initially optimized on a quadrupole-ion trap (Qtrap 5500; AB Sciex, Framingham, Mass.) mass spectrometer by direct infusion of standards using an external syringe pump. Negative ion electrospray ionization (ESI) was used due to enhanced sensitivity. Detection of each precursor ion and the corresponding highest intensity product ion was optimized by adjusting collision energies. The unique SRM transitions selected for each molecule were as follows: unlabeled F-Asn (293.1 m/z at a collision energy of −15 eV), $^{13}$C-labeled F-Asn (299.1 m/z at a collision energy of −15 eV), unlabeled asparagine (131.1 m/z at a collision energy of −12 eV), and $^{15}$N-labeled asparagine (133.1 m/z at a collision energy of −12 eV). To quantitate fructose-asparagine and asparagine, standard curves (0.01 µM to 100 µM) were constructed based on analyses of serial dilutions of unlabeled standards mixed with constant amounts of labeled standards. The limits of detection were 1 µM for fructose-asparagine and 0.5 µM for asparagine.

To verify the presence of F-Asn in mouse chow and intestinal rinse samples, the samples and standards were first reduced with NaBH4, as previously described 59; this reduction ensures the conversion of the ketose to a more stable alcohol (+2 Da mass change). Levels of fructose-asparagine and asparagine in chow and intestinal rinse samples were normalized to sample protein content. The result of the measurements (FIG. 16) is that there is F-Asn present in both autoclaved and irradiated mouse chow (autoclaved chow is fed to conventional mice, irradiated chow is fed to germ-free mice). Germ-free mice have F-Asn in their intestinal tracts, which is depleted upon infection with *Salmonella*. This suggests that germ-free mice cannot utilize F-Asn. Conventional mice have no F-Asn in their intestinal contents suggesting that there are members of the mouse microbiota that can utilize F-Asn.

Example 8. Small Molecule Targeting FraB

*Salmonella enterica* is one of the most significant foodborne pathogens in the United States and globally. There are no vaccines for non-typhoidal *Salmonella* serotypes, including *Typhimurium*. Antibiotics are used to treat *salmonellosis* in the very young, elderly, or immunocompromised, and for an emerging disease called invasive non-typhoidal *salmonellosis* (iNTS). Antibiotic resistance is prevalent and on the rise, however, and new therapeutic strategies are needed. Antibiotic resistance has made non-typhoidal *salmonellosis* a serious threat in the United States and globally. Because *Salmonella* cells lacking the FraB deglycase of the fructose-asparagine (F-Asn) utilization pathway accumulate a toxic intermediate during F-Asn metabolism, FraB is an excellent drug target. An aspect of the present embodiments provides for identifying, optimizing, and characterizing potent inhibitors of FraB, and developing novel therapeutic for non-typhoidal *salmonellosis*.

As an experimental model, the *Typhimurium* serovars is one of the most extensively characterized microorganisms that greatly facilitates hypothesis testing and modeling. Surprisingly, the present embodiments demonstrate that during growth in the inflamed mouse intestine *Salmonella* can rely on a single nutrient, F-Asn. Mutants lacking the F-Asn utilization system, encoded in the fra locus, have a 1,000- to 10,000-fold fitness defect as measured by competitive index (CI) assays. Therefore, it would appear that F-Asn may be a primary nutrient utilized by *Salmonella* in the inflamed intestine. The fra locus does not confer a fitness advantage in a *Salmonella* background that lacks SPI1 and SPI2 (that encode two distinct Type 3 Secretion Systems (T3SS)), nor in a background that lacks ttrA (that encodes a tetrathionate reductase), suggesting that *Salmonella* needs to induce inflammation and to respire anaerobically using tetrathionate as the terminal electron acceptor to benefit from F-Asn. F-Asn is found in some human foods at very high concentrations, greater than 1% dry weight, suggesting that *Salmonella* may rely heavily on this nutrient during human infection as well. This is a novel finding because no other organism has been shown to synthesize or utilize F-Asn, or exhibit such a strong dependence on F-Asn for its virulence. Given that mammals are not known to utilize F-Asn, the fra system of *Salmonella* provides an excellent and specific therapeutic target that is not likely to have non-specific effects on the host. The regulation and enzymology of F-Asn utilization provides novel therapeutics.

It has long been thought that nutrient utilization systems of *Salmonella* would not make effective drug targets because there are simply too many nutrients available to *Salmonella* in the intestine. The present embodiments, however, show that during growth in the inflamed intestine *Salmonella* relies heavily on a single nutrient—fructose-asparagine (F-Asn), which is present at high concentrations in human foods. Mutants that cannot acquire F-Asn are severely attenuated, suggesting that F-Asn is the primary nutrient utilized by *Salmonella* during inflammation. No other organism has been reported to synthesize or utilize this compound, although it is possible that a few other pathogens and members of the normal gut microbiota may be able to utilize F-Asn.

The apparent lack of F-Asn utilization pathways in mammals and most other bacteria suggests a novel, specific and potent therapeutic target for *Salmonella*. The locus encoding F-Asn utilization, fra, provides an advantage only if *Salmonella* can initiate inflammation and use tetrathionate as a terminal electron acceptor for anaerobic respiration (the Fra phenotype is lost in *Salmonella* SPI1⁻ SPI2⁻ mutants or ttrA mutants). If *Salmonella* can initiate inflammation (or enters a gut that is already slightly inflamed), it can begin tetrathionate respiration during F-Asn catabolism, and thereby outcompete the normal microbiota, which are doubly compromised by the inflammation and their ability to only ferment (but not respire) F-Asn.

The F-Asn utilization system represents a novel therapeutic target for small molecules that either block this utilization or disrupt the regulation. Small molecules that block either the activity of the transporter or the catabolic enzymes, or that prevent FraR release from DNA could all be potential new therapeutics. More specifically, the role of an asparaginase (FraE), kinase (FraD) and deglycase (FraB) in F-Asn utilization provide several targets. See FIG. 6. FraE is predicted to encode an asparaginase; a global MS-based proteomic analysis of *Salmonella* identified this protein in the periplasmic space. It appears that FraE is a periplasmic asparaginase that hydrolyzes the side chain of F-Asn to create fructose-aspartate (F-Asp) and ammonia. This enzyme may hydrolyze F-Asn to fructose-aspartate (F-Asp) and ammonia. FraA is a DcuA family transporter that may symport F-Asp with two protons; thus FraA transports the F-Asp into the cytoplasm. Within the cytoplasm, FraD is a kinase that may convert F-Asp to F-Asp-6-P. Finally, FraB is a deglycase that cleaves F-Asp-6-P to glucose-6-P and aspartate. FraR is a transcription factor of the GntR family that may repress the fra operon in the absence of F-Asn. A combination of genetic and biochemical methods are used confirm these functions. The FraR DNA binding site(s) is also determined, as is the inducer detected by FraR. Although nearly 40% of drug targets are membrane proteins, they remain challenging targets for structural biology and drug discovery platforms—FraA, a 46 kDa protein with multiple membrane-spanning domains, might be difficult to purify and characterize. Therefore, FraR regulator and the soluble enzymes encoded by fraE (asparaginase), fraD (kinase) and fraB (deglycase) are selected as initial targets.

Biochemical characterization of the individual reactions catalyzed by these Fra enzymes and development of high-throughput assays provides for screens that will identify small molecule inhibitors of these enzymes. The FraR transcription factor is likely a repressor; therefore, preventing its release from the fra operon promoter would also be of therapeutic interest. The natural inducer of FraR and the DNA binding sites of FraR in the fra operon are additional targets. Additionally, metagenomics, selective growth in the presence of F-Asn, and bioinformatics may be combined to test whether in healthy gut communities there are select members of the microbiota that can utilize F-Asn and prevent *Salmonella* from acquiring this nutrient. These findings on the enzymology and regulation of F-Asn utilization in *Salmonella*, and possible competing intestinal microbes, informs efforts to design new probiotic bacteria that can reduce the severity and duration of *Salmonella* infection. The present embodiments expand our understanding of *Salmonella* growth in the inflamed intestine and novel therapeutics.

*Salmonella* initiates a positive feedback loop that allows it to thrive in the inflamed gut. Most conventional mice, including C57BL/6, are exceptionally resistant to these efforts, but mice colonized with human microbiota are not, suggesting that the resistance is partly due to the make-up of the microbial community. Consistent with this observation, perturbations to the mouse microbiota, such as treatment with streptomycin, allow *Salmonella* to initiate its infection and thrive. It was recently discovered that CBA mice, which are persistently colonized by *Salmonella*, eventually become inflamed as well (at 10 to 14 days post-infection). It is known that if *Salmonella* can initiate inflammation (or if there is pre-existing inflammation), the oxidative burst results in the formation of tetrathionate, which *Salmonella* then uses as a terminal electron acceptor for respiration of select carbon sources, including F-Asn. There may be members of the normal mouse microbiota that can utilize F-Asn, thus preventing the growth of *Salmonella*. If *Salmonella* can initiate inflammation and respire via tetrathionate, it may compete more effectively for F-Asn, which allows further growth and more inflammation Inflammation may inhibit the F-Asn-utilizing portion of the microbial community, reducing the competition for F-Asn, which again allows *Salmonella* to thrive and initiate more inflammation. Probiotic strains that are resistant to inflammation, *E. coli* Nissle 1917, *Lactobacillus reuteri*, or attenuated *Salmonella* strains can be engineered to utilize F-Asn and compete against wild-type *Salmonella*. These probiotics can be added to foods or taken prophylactically to prevent *Salmonella* infection, or taken as therapeutics during *Salmonella* infection.

Genetic analysis of the regulator and enzymes required for F-Asn utilization are studied by constructing nonpolar deletions of each gene in the fra locus and plasmids that complement each gene. Each construct is assayed for growth on F-Asn as sole carbon or nitrogen source, and for mouse virulence (to date, all experiments have been performed with two different polar fraB::kan mutations and complementation with the entire locus). Because the orginal TraSH data did not detect a phenotype for the regulator or the asparaginase, all of the fra genes except these two may be required. If the asparaginase, FraE, is truly not required, then there are two potential non-exclusive explanations: First, sequence analysis suggests that there may be a promoter upstream of fraE, so that it is expressed in the fraB::kan mutant. This is tested by mapping the transcripts for the entire locus. Second, there may be functional redundancy—there are two other periplasmic asparaginases encoded in the *Salmonella* genome. Whether or not fraE is required for growth on F-Asn and for mouse virulence is tested in a series of strains lacking all three asparaginases in various combinations. Whether the asparaginase converts F-Asn to F-Asp is also explored by determining if the fraE mutant, or triple asparaginase mutant, cannot grow on F-Asn but can grow on synthetic F-Asp, which would suggest that the FraA transporter actually transports F-Asp.

If FraR is not required for growth on F-Asn or for mouse virulence (it did not appear to be required for mouse virulence in the original TraSH data), then FraR may act as a repressor of transcription, and that mutation of fraR allows expression of the operon in the absence of inducer. This is tested by qRT-PCR; and by constructing plasmid-based and chromosomal lacZY or luxCDABE fusions to the fraR, fraB, and putative fraE promoters and testing their regulation in the presence or absence of a fraR mutation or F-Asn. Mutation of fraR or addition of F-Asn or F-Asp will likely de-repress one or more of the promoters.

The regulator and enzymes required for F-Asn utilization are cloned, expressed, and purified. More specifically, the *Salmonella* genes encoding the putative regulator, asparaginase, kinase and deglycase are amplified by high-fidelity PCR and cloned into pET-33b, an expression vector that permits inducible expression from a T7 RNA polymerase promoter. The respective gene products are purified as His6-tagged proteins after overexpression in *E. coli* BL21 (DE3). Depending on the purity of the protein after the affinity step, an additional ion-exchange or size-exclusion chromatographic (SEC) step yields a homogeneous preparation. All proteins are purified using affinity tags engineered either at the N- or C-terminus. A tobacco etch virus (TEV) protease cleavage site is also incorporated immediately after the His6 tag to enable tag removal post-affinity purification. Because FraR, FraB, FraD, and FraE are 27 kDa, 37 kDa, 31 kDa, and 37 kDa, respectively, their purification is straightforward. These studies parallel protocols in place for routinely and successfully purifying other recombinant proteins (spanning in size from 10 kDa to 50 kDa). Mass spectrometry is used to determine the molecular masses of the purified recombinant proteins. After confirming agreement between the predicted and observed masses, the purified proteins are tested for their individual activities.

FraR, a transcription factor of the GntR family, likely represses the fra operon in the absence of F-Asn. GntR family members are found in diverse bacteria and use their N-terminal helix-turn-helix (HTH) motif to accomplish DNA recognition; the C-terminal domains typically are used to bind the inducers or effect oligomerization. GntR homologs affect a variety of metabolic processes, virulence and motility, and have been broadly sub-classified into seven categories based on some exemplars: FadR, HutC, PlmA, MocA, DevA, Arar, and YtrA. Although the amino acid sequences in these repressors and their corresponding DNA-binding sites are known, FrlR and FraR, the two factors which are believed to respond to F-Lys and F-Asn, provide the only known examples for understanding how Amadori products can regulate gene expression. This circumstance provides the opportunity to study how the binding of an Amadori product results in loss of DNA binding. This also supports the foundation for drug discovery that targets FraR, hence the focus on FraR's inducer role in vivo and the operator site(s) in the fra operon and in the fraR promoter.

Based on an analogous regulatory mechanism in bacteria for controlling utilization of fructosyl-lysine 65, either fructose-aspartate (F-Asp) or F-Asp-6-P functions as an inducer that causes FraR's loss of DNA binding capability and subsequent induction of the fra operon. This is analyzed by testing the binding of FraR for F-Asp/F-Asp-6-P by isothermal titration calorimetry (ITC). Different binding conditions (varying pH, salt, etc.) are used to ascertain the best conditions for complex formation. In addition to validating whether one of these ligands is a bona fide inducer, the ITC data provides thermodynamic parameters (e.g., enthalpy of binding), an estimate of the dissociation constant (KD), and stoichiometry. The KD value is compared with that of other known repressors (e.g., Ara-AraR, ~8 µM). Native MS provides the molecular mass of the putative FraR-regulator complex generated, and independently confirms the stoichiometry; moreover, use of ion-mobility and surface-induced dissociation MS (pioneered by Wysocki) helps elucidate FraR quaternary structure changes upon binding the inducer. Purifying the affinity-tagged FraR during *Salmonella*'s growth on F-Asn and using mass spectrometry to identify the compound bound to FraR allows the inducer's identity to be inferred from the difference in mass between that observed and that predicted for FraR, using MS/MS as needed to dissociate the inducer from FraR. The affinity-tagged FraR variant is the chromosomal copy, and is generated by homologous recombination. Accordingly, the identity of the FraR inducer is determined.

The operator site(s) in the fra operon is also identified. A search of the fraR, fraB, and fraE promoter regions for DNA sequences matching the consensus binding sequences of several GntR homologs identified weak similarity to known operators. To experimentally determine the FraR binding site(s), DNase I- and hydroxyl radical-mediated footprinting localizes the DNA sequence that is recognized by FraR. Like founding members of this family of transcriptional repressors (e.g., AraR), the sequence of FraR predicts distinctive DNA- and inducer-binding domains. For experimental validation, a mutant derivative that has only the DNA-binding domain is prepared, and its ability to bind a minimal operator DNA sequence is determined in vitro. Whether this interaction is unaffected by the presence of the inducer (F-Asp or F-Asp-6-P) is analyzed, in contrast to the full-length protein that is expected to lose DNA binding ability upon complex formation with the inducer molecule. DNA binding is assessed using (i) gel-shift assays and radiolabeled DNA, and (ii) fluorescence polarization assays with fluor-labeled operator. The latter reports on solution measurements and is free of the artifacts associated with the more easily performed gel-shift assays. With these methods in hand and the DNA-binding site mapped, a series of operator mutants is constructed to examine their binding to FraR. Loss of binding upon mutagenesis of the core operator validates the mapping results. In parallel with these in vitro experiments, mutant operators are also be examined using these reporter assays. The stem loop and putative small RNA within the fraD gene are also likely to be regulatory in nature and would be studied in similar ways.

The regions in FraR responsible for operator and inducer binding are identified. The binding sites are mapped using a chemical modification approach coupled with high-resolution mass spectrometry. Briefly, N-hydroxysuccinimide-biotin (NHS-biotin), a Lys-modifying agent, is used to distinguish positions in FraR whose accessibility is altered in the presence of the DNA ligand or the inducer. Free FraR and FraR-DNA (FraR-inducer) complexes are subject to modification with NHSB before separation on SDS-PAGE and in-gel digestion with endoproteinase GluC, which provides unbiased identification of peptides with or without Lys modification. Peptide MS/MS deduces which positions in the protein are protected upon binding to the operator DNA or inducer, allowing the mapping of FraR allosteric changes that are promoted by the inducer (as reflected in an altered proteolytic profile). This method has been used to map the tRNA-binding sites in a protein-only RNase P, an enzyme responsible for tRNA 5' maturation. The N-terminal, HTH module in FraR may bind the GntR operator and the "variable" C-terminal domain may bind the inducer. This approach also identifies a novel F-Asp-responsive domain in a DNA-binding protein.

The F-Asn utilization enzymes are also characterized biochemically. The three enzymatic activities required for F-Asn utilization are characterized in two phases. First, confirmation that the products expected from each reaction are indeed generated—having recombinant enzymes in hand—permits in vitro generation of reaction products in quantities needed for determination of exact mass by MS and structure by $^1$H- and $^{31}$P-NMR. For example, 50 μmol F-Asp is treated with 10 mM ATP and a defined amount of recombinant FraD (kinase) to test for production of F-Asp-P. Following a clean-up step and analytical anion exchange chromatography to isolate the phosphorylated product, MS determines the mass. If the phosphate is indeed attached to a carbon with two hydrogen atoms (i.e., the C6 position in F-Asp), $^{31}$P-NMR provides definitive evidence. The $^1$H-NMR spectrum provides unambiguous confirmation of the fructose and aspartate moieties. In the case of asparaginase, there are two predicted products: ammonia and fructose-aspartic acid (F-Asp). The latter is identified by comparison with the synthetic material via infrared and NMR analyses, and its characteristic reaction with ninhydrin-collidine; like aspartic acid, it reacts to give a distinctive sky-blue color. Fra mutants are exploited for further confirmation: after growing each in $^{13}$C—F-Asn, multiple-reaction monitoring MS is used for a targeted analysis of the intermediates predicted to accumulate. These approaches confirm that the three enzymes indeed catalyze their individual expected reactions.

More specifically, asparaginase activity has been measured traditionally by determining the amount of aspartate generated. Because FraE (asparaginase) converts F-Asn to F-Asp and ammonia, measuring the ammonia affords another route to assess its activity. Ammonia is reacted with hypochlorite and phenol to generate indophenol, which is quantitated at 670 nm. A commercial kit is available to perform these non-enzymatic assays in high-throughput if needed. Standard curves are generated using ammonium chloride.

Regarding kinase, FraD is hypothesized to convert F-Asp to F-Asp-6-P. Rather than directly measure the formation of F-Asp-6-P, the rabbit muscle pyruvate kinase (PK)-lactate dehydrogenase (LDH)-based coupled spectrophotometric assay is used. The underlying principle is that consumption of ATP by FraD results in generation of ADP, a substrate for PK that converts phosphoenolpyruvate to pyruvate in a substrate-level phosphorylation reaction. LDH converts the pyruvate (generated by PK) to lactate with concomitant oxidation of NADH, whose depletion is easily measured by following the absorbance at 340 nm.

Regarding deglycase, the conversion of F-Asp-6-P to Glc-6-P is measured using a glucose-6-phosphate dehydrogenase (G6PDH)-based assay in which the oxidation of glucose-6-phosphate to 6-phosphogluconate is accompanied by reduction of NADP+ to NADPH, which in turn is assessed by following the absorbance at 340 nm.

For kinetic and substrate-recognition studies, with the recombinant enzymes in hand, the facile assays just discussed are used to measure the standard kinetic parameters (Km, kcat) under multiple-turnover conditions. These values provide a framework for comparing activities of these enzymes against related substrates or activities in the presence of putative inhibitors. Several stereochemical analogs of F-Asn are prepared: Glucose-Asparagine (G-Asn), Fructose-D-Asparagine (F-AsnD), Ribulose-Asn (R-Asn) and Xylulose-Asn (X-Asn). This allows exploration of whether these analogs are substrates of the asparaginase. Similarly, the amino acid that is conjugated to fructose is varied to establish the specificity for the aglycone part—for example, whether the kinase can discriminate between F-Asp, F-Glu, and F-Lys. If an analog fails to act as a substrate, its inhibitory potential and the type of inhibition (competitive versus non-competitive) can be determined. Preparations of the various Amadori products have been of sufficient purity for the work described herein (ca. 95%). It may be desirable, however, to achieve sufficient purity to be able to crystallize these compounds, both to enable crystallographic studies and to remove unknown impurities. The Center for Molecular Innovation and Drug Discovery at Northwestern University provides preparative HPLC services for a reasonable fee.

If the initial chromatographic, electrophoretic, MS, IR, and NMR analyses of reaction products indicate a different reaction than those postulated, one can adapt accordingly. Experience in the use of different analytical and spectroscopic characterization methods as are known by those of skill in the art enable such work. Additionally, the in vivo approach to identify a FraR inducer may indicate that the inducer is neither F-Asp nor F-Asp-6-P. If this is the case, candidates are selected based on mass and additional characterization methods, such as MS/MS, that unambiguously identify the inducer.

The fraB phenotype has two components: The fraB phenotype is quite large during inflammation. For perspective, the fitness defect of mutants unable to utilize ethanolamine or sialic acid, in the same mouse model, are 10-fold and 2-fold, respectively (Thiennimitr et al., PNAS 108:17480 (2011); Ng et al., Nature 502:96 (2013)), while the fraB mutant has a defect of >1,000-fold. The cause of the fraB phenotype is the apparent buildup of toxic metabolite(s) during growth in the presence of F-Asn, an inference that emerged from the present studies on the fraB mutant (FraB disabled), which grows robustly in minimal medium with glucose as the sole carbon source, but not in the presence of glucose and F-Asn. This observation suggested that F-Asn is toxic to a fraB mutant. A fraD mutant, on the other hand, grows with wild-type kinetics in the presence of glucose and F-Asn. Therefore, the toxic intermediate may be F-Asp-6-P. Because F-Asn acquisition is important to *Salmonella* fitness, the cell could be starved by targeting FraA, FraB, or FraD, which potentially derives a therapeutic benefit. Indeed, targeting FraB both starves and poisons the cell, making it a most promising target among the F-Asn utilization enzymes.

A bank of 500,000 compounds is screened for inhibition of *Salmonella* FraB (deglycase) activity. To identify those compounds that can inhibit FraB activity in living cells, the hits are further screened for their ability to inhibit *Salmonella* growth in vitro. To demonstrate specificity, this growth inhibition is tested in the presence and absence of F-Asn (inhibition should be observed only in the presence of F-Asn). The structure of FraB is also solved by x-ray crystallography, and the structural information allows for computer-aided drug discovery and allows the elucidation of structure-activity relationships with the identified compounds.

High-throughput screening (HTS) of 500,000 compounds to identify FraB inhibitors can employ the small molecule library at Harvard Medical School, that includes >500,000 compounds that are available for screening on a fee-for-service basis. This vast library has compounds that are chemically and pharmacologically diverse, and offers ample possibilities for follow-up synthetic chemistry, thus enhancing the likelihood of identifying real leads for therapeutic agents. ~500,000 compounds are screened. The ICCB-Longwood Screening facility at Harvard assists at all stages of the screen: screen design, assay development and optimization, trouble-shooting, more complex automation tasks (e.g., compound pin transfer), data analysis, etc., a member of this research team is responsible for conducting the screen. The facility projects the assay of up to 40×384-well library plates/day in duplicate.

The primary screening strategy monitors FraB activity using a coupled assay that results in generation of the fluorescent product, resorufin. The rate of FraB-dependent cleavage of F-Asp-6-P into glucose-6-P and aspartate are measured using a glucose-6-phosphate dehydrogenase (G6PD)-based coupled assay in which the oxidation of glucose-6 phosphate to 6-phospho-δ-glucono-1,5-lactone is accompanied by reduction of NADP+ to NADPH, which in turn is used by diaphorase to convert a non-fluorescent resazurin substrate to a fluorescent resorufin product (see FIG. 17). This fluorescence assay is optimized for the 384-well format. In particular, assay additives that yield the highest activity are determined. For example, it has been shown that *E. coli* YhfN (a deglycase relative of FraB) is inhibited by metal ions and EDTA/EGTA is needed in the assay for optimal activity. Chaudhuri et al., 5 PLoS Pathog. e1000529 (2009). A systematic screen of optimal pH, temperature and assay additives will be performed before choosing the best conditions for the HTS. Other ongoing work characterizes the general kinetic properties of the deglycase using F-Asp-6-P synthesized in-house using FraD.

Minimizing downstream trial failures depends on accurate identification of hits. False positives are minimized by using a secondary assay. Such a strategy ensures that "hits" are true and potent (Ki~nM) inhibitors that bind to the molecular target and do not exhibit undesirable characteristics such as interference with detection methods. If the first screen yields 0.1% hits (i.e., 500 compounds out of 500,000), whether all of these hits are bona fide is determined using a secondary colorimetric assay for FraB. The secondary screening strategy again exploits G6PD to generate NADPH from glucose-6-P (a FraB product) (FIG. 17). The NADPH formed by G6PD is used as the electron donor to reduce the dye nitrobluetetrazolium (NBT). Phenazine methosulfate is used as a catalyst to aid this reaction that results in formation of water-insoluble NBT-formazan, whose concentration is measured using its absorbance at 585 nm. The dye formed is a direct measure of the NADPH, which in turn is a read-out of FraB activity; the assay is quite sensitive given the high extinction coefficient of NBT-formazan ($\epsilon$=16,000 M-1 cm-1 at 585 nm). Using fluorescence and colorimetric tests identifies bona fide hits (likely less than 500 compounds from an initial pool of 500,000).

This process identifies compounds that inhibit the activity of FraB using both the primary and secondary screening methods. It is possible that there are too many hits. Many of these are true inhibitors of the enzyme, but they might not be able to pass into the bacterial cytoplasm. Such inhibitors are eliminated by determining if these compounds can inhibit *Salmonella* growth. Another source of false positives is G6PD inhibitors because G6PD is present in both the primary and secondary screens. Once inhibitors are identified from the primary and secondary screen one can quickly assess if they inhibit G6PD using an independent assay. If some of the hits resulted from inhibition of G6PD, such inhibitors are eliminated.

Determining a crystal structure of FraB provides a structural framework for visualizing the active site of the target, and how it binds to substrates and small molecule inhibitors. Moreover, once methods for crystallizing FraB alone are established, structures with lead inhibitor compounds are performed. FraB is a 325 amino acid protein. Although there is currently no crystal structure of FraB, the structure of the YurP (FrlB) protein from *Bacillus subtilis*, which is 44% identical in sequence to FraB, has been determined (PDB code 3EUA, unpublished work from structural genomics initiative), and can be used as a template for 3D modeling and as search model for molecular replacement. YurP (FIG. 18A) forms a homodimer with a putative active site cleft located at the dimer interface (FIG. 18B). The cleft contains bound citrate and glycerol molecules from the crystallization mixture, and is lined by residues that are highly conserved in both enzymes (FIG. 18C). Although the YurP structure could be used for computational docking and structures with inhibitors, it is far more desirable to obtain the structural information directly on the FraB protein.

(His)$_6$-FraB deglycase was purified to homogeneity using immobilized metal affinity chromatography, and employed TEV protease to remove the (His)$_6$ tag. FraB is quite soluble and can be concentrated to 20 mg/ml. Preliminary screens yielded a hit as shown in FIG. 23. Hits are optimized using standard 24-well hanging drop plates. X-ray diffraction data is collected using an x-ray source or a beamline 31-ID of the advanced photon source (synchrotron, Argonne National Laboratory). The structure is determined by molecular replacement using the known structure of YurP (PDB code 3EUA) as a search model, and refined using the CCP4 crystallographic software package. Winn et al., 67 Acta Crystallogr. Sect. D-Biol. Crystallogr. 235 (2011). To study the catalytic mechanism, and to determine the degree to which there are conformational changes during the reaction, inactive mutant forms of FraB is co-crystallized with substrate compounds. Based on structural analysis, a histidine and three glutamate residues have been identified as potential catalytic residues for mutation to alanine.

A goal of the crystal analysis is to obtain a crystal structure of *Salmonella* FraB at a resolution of 2.5 Å or better. Because the first set of screens has already yielded crystals, it is highly likely that a structure for FraB will be obtained. It remains possible that the crystals do not diffract well, or that the molecular replacement method of solving the structure will not work. If the resolution of the crystals is poor (less than 2.5 Å), limited proteolysis that defines a stable domain of FraB can be determined and the expressed, purified, and crystallized. In particular, the first ~20 amino acids of FraB do not appear to be conserved with the crystallized YurP protein, and may need to be truncated. Experimental phasing using heavy atom methods is possible. The coordinates and stereo-chemical parameters for substrate and inhibitor compounds are generated with the PRODRG2 server. Wiame & Van Schaftingen, 378 Biochem. J. 1047 (2004). Structures are fit to electron density maps using COOT (Schuttelkopf & van Aalten, 66 Acta Crystallogr. Sect. D-Biol. Crystallogr. 486 (2011)), and refined with REFMAC5 (Steiner et al., Acta Crystallogr. Sect. D-Biol. Crystallogr. 2011).

Additionally, the MIC (minimum inhibitory concentration) and MBC (minimum bactericidal concentration) of HTS-identified inhibitors against *Salmonella* grown in liquid culture are measured; and the $IC_{50}$ (half-maximal inhibitory concentration) determined for those inhibitors most effective against *Salmonella*. More specifically, each hit compound identified in primary and then secondary screening is tested for its ability to inhibit *Salmonella* growth in minimal medium containing F-Asn or glucose as the sole carbon source. This experiment quickly identifies those hits from the "HTS cherry picks" that can cross the *Salmonella* inner and outer membranes, and inhibit *Salmonella* in a F-Asn-dependent manner. A majority of the hits are eliminated by this screen, because they either fail to penetrate the bacterial cell, or they inhibit *Salmonella* in a manner that is not dependent upon F-Asn (i.e., they inhibit during growth on glucose indicative of off-target effects). This quick screen is a simple and powerful way to identify only those compounds that can penetrate the bacterial cell and inhibit in the manner expected. A full MIC and MBC determination is then performed for those compounds that do indeed inhibit *Salmonella* growth in a F-Asn-dependent manner. The winners are then characterized with respect to enzyme inhibition in vitro.

In screening for *Salmonella* growth inhibition and measuring the MIC and MBC values, all of the hits are tested for their ability to inhibit growth of *Salmonella* on F-Asn, but not glucose. An inhibitor titration is performed in a 96-well format—specifically, a 3-fold dilution series of each inhibitor is performed over eleven wells (for example, spanning 0.17 nM to 10 μM). The first well in each 12-well series contains no inhibitor. Because the ICCB-Longwood Harvard Compound libraries are stored in DMSO, *Salmonella* is tested over a DMSO dilution series that mimics the inhibitor experiments. This control is included although no adverse effects are expected given the low concentrations of DMSO.

Each inhibitor is tested in duplicate in the presence of either glucose or F-Asn, allowing us to test two inhibitors in a 96-well plate. *Salmonella* are inoculated into each well and growth monitored over time at 37° C. in a SpectraMax M5 plate reader. Only those compounds that are inhibitory in F-Asn but not in glucose are studied further; this provides a safety net for off-target effects. A preliminary measurement of the MIC at this point is the lowest concentration of drug that prevents an optical density increase in the F-Asn well. For those compounds that pass this test (likely ~20% of the initial cherry-picked pool), the MIC is determined again using the same protocol largely for reproducibility. To determine the MBC, a small portion of the well contents from each MIC experiment will be dilution-plated on LB agar plates to test for growth to determine if the organisms in the well are alive or dead. The lowest concentration of compound that has decreased the number of CFU in the initial inoculum by 99.9% is the MBC. Comparison of the MBC and MIC values reveals whether the compound is bacteriostatic or bactericidal. If the MBC and MIC values are similar, the compound is bactericidal, but if the compound is bacteriostatic the MBC value is much higher than the MIC.

The $IC_{50}$ values are examined for concentration-response for the most promising compounds based on *Salmonella* MIC (likely ~10% of the initial cherry-picked pool). The inhibitor titration is performed in duplicate using the 96-well format described above. Thus, each 96-well plate allows for the $IC_{50}$ values for four inhibitors. Similar to the growth experiments described above, a 3-fold dilution series of each inhibitor is performed over eleven wells—the first well in each row will be used for positive (deglycase without any inhibitor) or negative (without deglycase or inhibitor) controls (in alternate rows). The goal is to obtain a measure of fractional activity, i.e., activity in the presence of inhibitor/ activity in the absence of inhibitor, and then use these data in a concentration-response plot to determine the $IC_{50}$ values. As pointed out by others (Copeland et al., 5 Bioorg. Med. Chem. Lett. 1947 (1995)), rather than use the mean of duplicate measurements (which is common practice), only one concentration-response plot is obtained by using the replicate data from duplicate runs with a given inhibitor to gain more degrees of freedom during non-linear curve fitting.

Although Ki values and the nature of inhibition for the top-scoring inhibitors are examined, the $IC_{50}$ values help rank-order the compounds and assess possible correlations between structural attributes and inhibitory potential. Such an analysis allows advancement towards a low-resolution pharmacophore model that will help elucidate structure-activity relationships, particularly key features for potency and active-site specificity. Also, this permits the focus on the top compounds from each group thus identifying diverse lead candidates.

This classification also exploits a web-based tool that converts $IC_{50}$ values to $K_i$ values (http://botdb.abcc.ncifcr-f.gov/toxin/kiCalES.jsp), and provides insights into whether the inhibitor is tightly bound. With user-defined input values for enzyme concentration, substrate concentration, $K_m$, and $IC_{50}$ values, the web tool returns $K_i$ values for competitive, uncompetitive and noncompetitive inhibition based on either classic inhibition or tight inhibition equations. For tight-binding inhibitors, which fail to follow Michaelis-Menten kinetics, the returned values for the two sets of equations are dissimilar. This simple tool allows inclusion of the "tight-binding" trait in the classification.

To assess specificity, top inhibitor candidates are further tested against more isolates of *Salmonella* and *E. coli* (the latter as a negative control that does not encode FraB), as well as other microbes, to ensure the generality of the findings. The compounds will likely inhibit the majority of non-typhoidal *Salmonella* serotypes, and possibly some pathogenic *Citrobacter* species that appear to encode a fraB homolog. The typhoidal serotypes of *Salmonella* do not encode the fra island, nor do the non-pathogenic *Citrobacter* species. Therefore, these and other microbes should not be affected by the inhibitors.

The benchmark for this portion of the study is that at least one compound must be found that inhibits the pure FraB enzyme with an $IC_{50}$ value of less than 10 μM, and inhibits *Salmonella* growth in the presence of F-Asn with an MIC of less than 100 μg/ml. Bactericidal compounds are preferred over bacteriostatic, but both are acceptable. Although unlikely, some of the inhibitors are not as species-specific as expected, inhibiting organisms other than *Salmonella*. This could arise due to a broad ability to inhibit homologous deglycases, or through off-target effects. Because the goal is to find narrow spectrum drugs that do not disturb the normal microbiota, broad spectrum inhibitors are not pursued.

Next, FraB inhibitor HTS hits are down-selected through biochemical characterization. Hits are transitioned to leads through in silico screening and medicinal chemistry. Although the HTS is expected to furnish several hits, improving them to potent lead inhibitors entails optimization of various attributes. Biochemical studies and a structure based, computer-aided combinatorial approach designs such high-affinity lead inhibitors of FraB. The expectation is that the in silico strategies below might yield solutions that converge with the experimental hits, affording a powerful validation. They might also identify new compounds whose chemical and structural features merit inclusion with the experimental hits. The overall goal is to develop testable hypotheses regarding key interactions between small molecule inhibitors and the FraB binding pocket(s), and to use this information iteratively for improving inhibitor potency.

Kinetic studies to evaluate and characterize the top FraB inhibitors (identified as such based on MIC and $IC_{50}$ values) can be conducted following the roadmap outlined by Copeland (5 Bioorg. Med. Chem. Lett. 1947 (1995)). There may be about ten inhibitors that are structurally distinctive and are exemplars of the different structural/potency classes identified. We will sequentially assess for each inhibitor the following attributes: (i) reversibility (ii) nature of inhibition and (iii) Ki value. In addition, we will assess possible synergy among the inhibitors based on answers to this first set of questions.

To address the issue of reversibility, FraB and an inhibitor will be pre-incubated at 37° C. using an enzyme concentration that is 100-fold over that used in our typical HTS assay and an inhibitor concentration that is at least 10-fold greater than the IC50 value. We will then perform a 100-fold dilution of this mixture. This dilution experiment should yield a fractional activity of 90% if the inhibition is rapidly reversible. If this 90% fractional activity is not immediate but is eventually achieved over longer assay duration, then it implies a slower reversal of the inhibition. If this fractional activity is never regained, then the inhibition is irreversible. For these dilution experiments, we will include a control to assess if FraB retains proportionate activity upon dilution.

Because competitive, uncompetitive, and noncompetitive inhibitions lead to changes in $K_m$ and kcat values that are easily distinguishable, one can measure the initial velocity of FraB over a wide substrate concentration range (e.g., 0.1 to 10 $K_m$) in the absence and presence of inhibitors. Three different inhibitor concentrations are recommended (concentrations that lead to 25%, 50% and 75% inhibition when $S=K_m$). Copeland et al., 1995. The initial velocity data is then subjected to Michaelis-Menten analysis to obtain the $K_m$ and kcat values, which in turn will identify both the nature of inhibition and the $K_i$ values. Structural/chemical traits of the inhibitors and their mode of inhibition are correlated.

If two lead compounds, X and Y, are found to be competitive and noncompetitive inhibitors, respectively, it is conceivable that they might work synergistically. This can be tested by measuring the $IC_{50}$ values for X and Y separately and together in tests with purified FraB, and using these $IC_{50}$ values to calculate the fractional inhibitory concentration index (FICI): FICI=FICX+FICY=IC50XY/IC50X+IC50XY/IC50Y. Meletiadis et al., 54 Antimicrob. Agents Chemother. 602 (2010); Zhu et al., 2013. An FIC index score lower than 1 will imply synergy. If combinations are identified that afford synergy in vitro, live *Salmonella* are used to determine the MIC values for X and Y separately and together in order to assess the FICI for the MIC values. In this case, FICI=FICX+FICY=MICXY/MICX+MICXY/MICY. (Note: The QSAR and SBDD studies discussed herein might uncover non-overlapping binding sites for two competitive inhibitors—therefore, synergy studies need not be limited to inhibitors which individually target the active site and another binding site on FraB.)

Regarding quantitative structure—activity relationship (QSAR), once hit compounds are identified through HTS, both ligand- and target-based optimization are initiated. For establishing ligand-based QSAR, the panel of inhibitors is collected to build a low-resolution pharmacophore model in order to elucidate critical interactions for potency and specificity. Subsequently, we will build a high-resolution QSAR model through regressions on possible congenial compound classes. Such a model will be useful for design and synthesis of lead analogs.

Regarding structure-based drug design (SBDD), this will exploit the high-resolution structures of FraB with and without inhibitor bound to the enzyme. Two virtual screening protocols are used as part of the in silico HTS to identify novel inhibitors. In the conventional screening approach, commercially available compounds from large general libraries such as the ZINC and NCI databases will be docked globally through cross-validating AutoDock (Morris et al., Curr. Protoc. Bioinform., Unit 8.14 (2008)) and Glide (Friesner et al., 47 J. Med. Chem. 1739 (2004); Halgren et al., 47 J. Med. Chem. 1750 (2004)) programs. Glide SP is used to conduct a rapid screening guided by a rough standard scoring function. Up to 5,000 top-scoring compounds can be re-scored with Glide 4.0 XP (extra precision) function. The top 50 hits are then subjected to experimental verification through standard FraB assays. Hierarchical screening harnesses a novel hierarchical virtual screening protocol to search for novel leads by using AutoDock4/AutoDockVena. The first stage of this hybrid dry-wet bench approach entails discovering the appropriate scaffolds from an in-house structurally diverse library of 10,000 compounds. The second stage aims to uncover the best analogs of the compounds discovered in the first pass by combining docking with similarity searching. The top 50 compounds with lowest binding energy are assayed. Any validated hits expands the selection to topologically similar compounds, which are screened virtually to recover more hits/leads in this particular chemical class, then validated experimentally.

The general and diverse nature of small molecule libraries is improved, and encompasses the chemical "drug-space" as broadly as possible. Compounds from widely different databases, including, but not limited to, ACD, KEGG, ASINEX, NCI, Maybridge, ZINC, ChemBridge, Sigma, WDI, CMC and MDDR, are continually filtered and merged into the database built on MySQL. Accelrys Cerius2. Diversity module (www.accelrys.com) can be used to sample representative potential leads using diversity and similarity analysis. This module rapidly calculates over 120 descriptors including electronic, conformational, thermodynamic, topological and shape descriptors and utilizes a variety of algorithms for selecting diverse subsets, including distance-based and cell-based selection methods. Multiple ADME/Tox filtering utilities such as QuikProp (Small-Molecule Drug Discovery Suite: QikProp, version 3.6, www.Schrödinger.com) will be incorporated to score for log P, solubility, surface area components, hydrogen-bonding potentials, Caco-2/MDCK cell permeabilities and logKhsa for human serum albumin-binding possibilities.

The optimization strategy builds on insights gained from the x-ray crystal structure of FraB bound to an inhibitor. In situ library design of the inhibitor-binding site can be accomplished with CombiGlide (Schrödinger.com) or Allegrow (bostondenovo.com). New compounds with better binding energy and reliable clustering statistics can be synthesized and tested—in this regard, it is worth highlighting that the libraries available for screening are rich in compounds that are ready for follow-up medicinal chemistry. As the inhibitor pool increases, better ligand based QSAR model can be built and refined. Moreover, the FraB/inhibitor complex structural model can also be improved to include potential induced-fit of the new analogs through molecular dynamics simulation. In addition, detailed binding free energy analysis could be utilized to dissect binding contributions from modifiable parts of the inhibitors, guiding and enabling further compound optimization. Moreover, both new X-ray structures of FraB/inhibitor and MD simulations might reveal novel binding pocket(s) near or far from the active site due to FraB conformational alterations. For the nearby pocket, new drug fragments can be designed and then synthetically linked to the existing inhibitors; for the faraway site, another round of in silico screening identifies allosteric leads.

Through the iterative process of QSAR and SBDD, analogs of promising lead compound(s) are designed through CombiGlide and with MLSD modeling strategy for better potency and specificity, and then synthesized for experimental testing. Moreover, studies that explore possible synergy between inhibitors furnish clues for synthesis of new chimeras. For example, new lead series can be generated by linking together the non-overlapping parts of two inhibitors that show synergy and whose binding sites are proximal. Indeed, Zhu and others used such a strategy to develop novel antibacterial drug lead compounds inhibiting bacterial undecaprenyl diphosphate synthase, an essential enzyme involved in cell wall biosynthesis. Zhu et al., 110 PNAS 123 (2013).

Although unlikely, if the biochemical studies identify covalent inhibitors from our winners, MS/MS proteomic studies can be undertaken to identify the binding site of the inhibitor in FraB. It is possible that despite synergy in vitro with respect to inhibition of FraB, combinations of inhibitors might not elicit the same increased potency in vivo due to differences in transport across the *Salmonella* membranes. Regardless, any combination that does work will be a major advance and therefore this effort is warranted.

If the above described QSAR and SBDD methods are not fruitful, an unlikely scenario given their proven success in other instances, there is a backup a fragment-based approach using a computational multiple ligand simultaneous docking (MLSD) strategy. The power of this method was demonstrated with STAT5, an oncoprotein. Li et al., 54 J. Med. Chem. 5592 (2011). Briefly, all the small chemical fragments that bind weakly at or near a target's hotspot are collated—these drug scaffolds resulted from either HTS or computational studies. Subsequently, these fragments are linked into a new entity to create a more powerful inhibitor. Such an inhibitor designed de novo might be synthesized or subjected to similarity search of template compounds already present in the various databases.

To determine the high-resolution structure of FraB bound to the most potent inhibitors, rank-ordered based on biochemical and culture studies, the structure of FraB alone and with substrate compounds is determined. The structures of FraB in complex with the most promising inhibitor compounds are determined. The structures show at the atomic level how the compounds bind to FraB, and suggest how functional groups could be altered or appended to develop new inhibitors with enhanced binding or solubility characteristics. The structures also provide information on the extent to which the compounds induce conformational changes in FraB, and thus provide an enhanced framework for computer-based screening approaches.

The framework for purification and crystallization of FraB is been established as described above. Lead inhibitor compounds (purchased from the HMS screening facility or other commercial source, or synthesized in-house) are dissolved in DMSO or ddH$_2$O as required, and either co-crystallized with a 10-fold molar excess over FraB or alternatively soaked into pre-existing crystals. Structures are determined by molecular replacement or difference Fourier methods. The structures of FraB in complex with a minimum of twenty lead inhibitor compounds are determined. This number could potentially be higher if a robust crystallization platform is established.

The therapeutic index and pharmacokinetic properties of the top 5 inhibitors is determined. This strategy verifies that the FraB inhibitors are bacteria-specific and host-exempt, by first eliminating all compounds that are toxic to mouse or human cells. An in vitro therapeutic index (TI) is determined by dividing the IC$_{50}$ of the compound against tissue culture cells, determined here, by the MIC against *Salmonella*. Up to five of the most promising compounds are then studied in mice to determine their (i) toxicity, (ii) ability to protect against *Salmonella*-mediated disease, and (iii) pharmacokinetic properties.

Regarding the therapeutic index with cell lines, before initiating animal studies, the top inhibitors are tested for cytotoxicity towards mouse and human macrophage-like cells (J774.1 and THP-1), epithelial cells (Caco-2) and fibroblasts (3T3). Cultured cells are incubated with a dilution series of each inhibitor to determine the IC$_{50}$. This value is divided by the MIC of the compound against *Salmonella* to determine the in vitro therapeutic index. Because several lines are tested, the least promising IC50 is used for this calculation. The compounds are rank-ordered by this therapeutic index and up to five compounds advanced to animal studies.

Single dose toxicity studies in animals are used to examine the acute or short-term (1 day) MTD (maximum tolerated dose) and NOAEL (no observable adverse effect level) of the inhibitors is determined. All of the compounds are dissolved in DMSO or ethanol at a concentration near their solubility. Serial dilutions of these solutions (or a more concentrated solution if necessary) will be prepared. Individual mice receive progressively lower (or higher) intravenous (IV) doses (tail vein) and oral doses until the dose that does not result in overt toxicity (e.g., paralysis, inability or unwillingness to move about cage, loss of righting reflex) within 24 hours is found, corresponding to the estimated acute MTD (10, 25, 50, and 100 mg/kg). Additional dosage groups may be required dependent on the results obtained.

Regarding the therapeutic index in animals, there are numerous mouse models for *salmonellosis*, however not all of them are relevant because FraB is important for *Salmonella* virulence only during inflammation. Conventional mice with a healthy microbiota do not become inflamed from *Salmonella* infection, and thus fraB has no phenotype in these models (and compounds would not be expected to have an effect either). A fraB mutant has dramatic phenotypes in mouse inflammation models, however, including germ-free C57BL/6, germ-free Swiss Webster, strep-treated C57BL/6, strep-treated Swiss-Webster, humanized (germ-free colonized with human microbiota), and conventional IL10−/− mice. For these studies, the strep-treated Swiss Webster model was chosen because these mice become inflamed and because they are Nramp1+/+ which means that they are more resistant to systemic infection than C57BL/6, taking about seven days to die from a dose of $10^7$ *Salmonella*. Effectiveness of the drug is measured as preventing death at fourteen days post-infection. To initiate the experiment, groups of ten streptomycin-treated mice are orally gavaged with $10^7$ CFU of *Salmonella*. Beginning on the following day, each group of ten mice receives a different dilution of compound orally once per day throughout the experiment. The $ED_{50}$ is calculated as the dose that prevents death in 50% of the animals. The therapeutic index is calculated as the MTD (or NOAEL) as provided above, divided by the $ED_{50}$ as determined herein.

The pharmacokinetics of IV versus oral dosing is also determined. After the single dose toxicity and therapeutic index studies have been performed, the calculated MTD of the compounds given IV and oral will be used for pharmacokinetic (PK) analysis to determine oral bioavailability and tissue concentrations. Briefly, mice will be administered the ½, ¼, and ⅛ of IV MTD of the compound calculated above and a separate set of mice will be administered the ½, ¼, and ⅛ of oral MTD by the oral route. Mice are sacrificed at times 0, 0.5, 1, 1.5, 2, 4, 6, 8, 12, and 24 hours for plasma and tissue collection (brain, spleen, liver, kidney, heart, lung, intestine, fat, and skeletal muscle). Drug and major metabolite concentrations are quantified in plasma, spleen and brain via validated liquid chromatography/mass spectrometry methods. Concentrations are also determined in other tissues using partially validated assays to crudely determine relative exposures in the various tissues. Concentration vs. time profiles are defined and non-compartmental and compartmental analyses are performed in Phoenix (Pharsight, Mountain View, Calif.) to estimate drug PK parameters: clearance, CL; volume of distribution, Vd; elimination half-life, T½; area under the concentration-time curve, AUC; maximum concentration, Cmax; and the time to reach maximal concentration, Tmax. PK analysis is performed by the OSU Comprehensive Cancer Center Pharmacoanalytical Resource Core as a research service.

The cell culture toxicity assay is a simple method of rank-ordering the potential of compounds before initiating animal studies. This undertaking is straightforward with no problems expected. The animal studies assess toxicity and effectiveness, along with pharmacokinetic properties, and identify the most promising compound(s) for future studies. At this stage, a potent new therapeutic is developed: one lacking selective pressure for resistance and lacking broad impacts on the normal microbiota.

Regarding the use of vertebrate animals: (1) Description of the proposed use of animals. Swiss Webster mice are treated with streptomycin to disrupt their normal microbiota and make them susceptible to *Salmonella*-mediated gastroenteritis. Lead drug compounds, bacteria (*Salmonella enterica* strain ATCC14028), or both, will then be administered. This will allow a determination of the MTD (maximum tolerated dose) and NOAEL (no observable adverse effects limit) of the lead compound alone, and the ED50 (effective, or therapeutic dose). For ethical reasons, the animals are not allowed to die from any of these treatments. The animals will be euthanized if early removal criteria are met.

(2) Justification of the use of animals, choice of species, and numbers of animals. To determine if a drug candidate will be toxic or effective, the candidate must be studied in animals. There are no mathematical models that can substitute. Great care is taken to study only the most promising candidates in animals. First, the compound must be highly effective against its target, in this case *Salmonella*, in vitro. Then the compound must not be toxic to tissue culture cells in vitro. Only when these conditions have been met is a compound tested for toxicity and effectiveness in mice. The host in this proposal is the strep-treated Swiss Webster mouse, which is Nramp1+/+ and resistant to systemic *Salmonella* infection. The determination of ED50 and MTD/NOAEL for each compound requires up to eighty mice per experiment (ten mice per dose of compound and 4 doses (spaced at 1-log intervals) for a total of eighty mice per ED50 determination and eighty mice per MTD/NOAEL determination). A maximum of five compounds are tested, with the top three being tested a total of three times (eleven total determinations×160=1760 mice). Pharmacokinetic studies use five mice per group and ten time-points (fifty mice per compound). A maximum of five compounds are tested, with the top three being tested a total of three times (eleven total determinations×50=550 mice).

(3) Veterinary care. For example, care is provided per a 24 AAALAC-accredited animal research facility that houses 125,000 mammalian and 50,000 non-mammalian animals per year. Four full time veterinarians and 75 ULAR (university lab animal resources) employees take part in animal care. All animals are observed daily by ULAR for assessment of health. Laboratory personnel also observe the animals daily for assessment of health. If either ULAR or lab personnel determine that an animal has achieved the early removal criteria outlined in section 4, below, the animal is euthanized. Mice are euthanized by lab personnel. Euthanasia procedures are described herein. The research protocol involves housing infected animals for up to three weeks. At that point, mice are euthanized for tissue harvest by the lab personnel. The lab coordinates with the veterinary staff before starting experiments. The animal housing facilities are in full compliance with the standards set forth in the PHS "Guide for the Care and Use of Laboratory Animals."

(4) Methods for pain and stress relief. No restraint or survival surgeries are performed. If during the course of these experiments any animal in the study shows anorexia for greater that 24 hr, disinclination to move for 12 hr, loss of normal neurological function as evidenced by locomotory or balance deficits, or vocalization in applicable species for more than 2 hr, then euthanasia is performed in accordance with the 2000 AVMA Guide for Euthanasia.

(5) Method of euthanization. Mice are euthanized using CO2 (>70%, inhaled) followed by cervical dislocation. This method is consistent with the recommendations of the Panel on Euthanasia for the American Veterinary Medical Association.

These Examples should only be used in a laboratory has a biosafety protocol that has been approved by an Institutional Biosafety Committee. Such protocol should cover all of the microorganisms discussed in this application including *Salmonella*, *E. coli*, and all members of the normal human and mouse microbiota. The protocol also covers recombinant DNA work. Upon entering the lab, new members are trained on BSL2 and chemical safety procedures, in addition to taking courses administered through the appropriate office of Environmental Health and Safety. All members of the lab are required to take an annual refresher course and to pass an exam on BSL2 safety procedures administered through the appropriate office of Environmental Health and Safety.

The fra locus, which encodes F-Asn utilization enzymes, provides an advantage to *Salmonella* only if the pathogen can initiate inflammation and use tetrathionate as a terminal electron acceptor for anaerobic respiration. The fraB mutant phenotype is present only in inflamed mice, and is lost in *Salmonella* genetic backgrounds that cannot initiate inflammation (SPIT⁻ SPE⁻) or cannot respire using tetrathionate (ttrA). A fraB mutation, in particular, is severely defective in inflamed mice. Absence of the FraB deglycase appears to cause accumulation of a toxic metabolic intermediate (F-Asp-6-P) that kills the cell. Thus, inhibiting FraB will both deprive *Salmonella* of F-Asn and intoxicate the cell. This novel target is non-essential in that a fraB mutant has no fitness defects during growth in LB broth or minimal medium with glucose as the carbon source, or in conventional non-inflamed mice. A drug inhibiting FraB would only target *Salmonella* that is actively respiring F-Asn during inflammation, greatly decreasing the selection for drug resistance. Therefore, screen 500,000 compounds are screened for their ability to inhibit FraB, and the IC50, MIC and MBC of the most promising compounds is determined. The atomic resolution structure of FraB is characterized using X-ray crystallography. In silico screening and medicinal chemistry enhances and optimizes the collection of inhibitors. Additional iterative refinement of inhibitor potency and specificity can be facilitated by establishing the tertiary structures of FraB bound individually to the most potent inhibitors. After screening for toxicity against several mouse and human cell lines, the therapeutic index of the most promising candidates is determined in mice. Thus, novel and much needed therapeutics for non-typhoidal salmonellosis are identified.

Example 9. Identification of Normal Microbiota that can Utilize F-Asn and Determination of Inflammation Sensitivity There are several lines of evidence suggesting that a few members of the normal microbiota can utilize F-Asn. First, a bioinformatics approach has revealed that some *Clostridia* appear to encode a fra locus. Second, germ-free mice have F-Asn in their cecum contents while conventional mice do not, suggesting that the microbiota is utilizing the F-Asn. In vitro and in vivo strategies are used to explore the microbiota. An in vitro method consists of growing mouse and human intestinal contents or feces in a variety of minimal media that contain F-Asn as the carbon source. It is likely that organisms able to utilize F-Asn will fail to grow in minimal medium due to other missing requirements, but some bacteria grow in *Clostridium* minimal medium (DSMZ *Clostridium* medium #143 with carbon sources removed). Turbidity is obtained in cultures inoculated with mouse or human feces. The 16S rRNA genes of these cultures is then sequenced. These cultures are plated on rich medium to obtain single colonies and the resulting isolates are then be re-cultivated in F-Asn minimal medium and in the same medium lacking F-Asn, as a control. Other minimal media are attempted using both human and mouse feces. Human feces in frozen stocks are obtained from a fecal transplant center, such as the one at Ohio State University, under an approved IRB protocol. The 16S rRNA gene from all current and future F-Asn utilizing isolates are sequenced, and then the genome sequence of unique organisms is determined. The genes encoding putative F-Asn utilization enzymes are identified in these genomes. Although it is somewhat unpredictable whether genetic manipulation of the genes in these organisms is possible (as their genetic tractability is hard to predict), qRT-PCR can determine whether the putative F-Asn utilization genes are responsive to F-Asn.

An in vivo method enriches the organisms that can utilize F-Asn within the mouse intestinal tract by adding F-Asn to drinking water. Even though there is F-Asn in mouse chow, the addition of more F-Asn in the drinking water may enrich the intestinal population for F-Asn utilizers. Removing the mouse chow just before "lights out" in the mouse facility, and then collecting fecal samples (or euthanize and harvest intestinal sections) in the morning just before their chow is returned will enhance the effect. In this way, the F-Asn in the drinking water is the only nutrient source for 12 hr before collection (half a day is the maximum fasting time allowed by good animal care-taking practices). Other groups of control mice receive either glucose in their drinking water, or no addition. The enriched species are detected using 16S rRNA gene community profiling via MiSeq amplification of the V4 region. Not all taxa will respond directly to F-Asn, but some may increase in abundance by benefiting indirectly. Although the 16S rRNA based approach enables a rapid, and cost-effective profiling of treatments and a broad view of taxonomic changes in community structure, it fails to examine functional changes. With high throughput sequencing, it is now possible to parse individual genomes from complex microbial communities to profile the metabolic potential for each genome. Here, that same approach can identify the microorganisms that can directly use F-Asn from those that might benefit indirectly. Shotgun sequencing of genomic DNA without amplification is conducted on a Illumina HiSeq 2500, followed by searching for homologs of F-Asn utilization enzymes in the genomes and also assembly-free 16S rRNA reconstruction by EMIRGE. Organisms that have homologs of the FraD kinase, the FraB deglycase, and the FraE asparaginase, all within close proximity on the genome, will be considered Fra-positive. Using the human gut system as a guide, it is anticipated that these systems are genomically tractable and result in near complete assembled genomes for metabolic profiling. Some systems may not be well-suited for genomic assembly and reconstruction, and other assembly-free approaches exist that would enable recovery of F-Asn utilization enzymes.

Assembled genomic bins representing each organism in the community are identified via 16S rRNA genes or single copy housekeeping phylogenetic markers, with the contigs in each bin annotated to identify desired gene targets. The benefit of an assembly-based approach over non-assembly method is it has the capacity to recover the metabolic potential of yet cultivated bacterial and archaeal lineages and organisms not yet genomically sampled and more directly link function to taxa identity. All bioinformatics from 16S rRNA profiling (e.g., read quality control, QIIME, Mothur) and whole genome analyses (e.g., read quality control, assembly, annotation, binning, EMIRGE and taxonomic assignment) are conducted by analysis pipelines with extensive research experience with genomic reconstruction and 16S rRNA profiling from diverse microbial systems including human guts. Additionally, if genomic reconstructions fail to identify differences in gene content or community structure between treatments, transcriptomic data can also be processed to correlate phenotype with differences in gene expression. Pipelines for 16S rRNA and shot-gun genomic/transcriptomic data analyses are already developed and operational on other projects by those of skill in the art.

This Example also generates a list of normal microbiota species that have the potential for F-Asn utilization (as predicted by their genomes) and some that are confirmed F-Asn utilizers. This list comes from (1) bioinformatic searching of the Human Microbiome Project (HMP) database (already completed, yielding four members of the Clostridia class); (2) from in vitro culture and isolation; and (3) from metagenomics of mouse intestinal communities enriched, or not, with F-Asn. These three lines of inquiry provide overlapping sets of organisms, further enhancing confidence in their identification.

With the identification of these organisms in hand, the hypothesis that streptomycin or inflammation suppresses these same organisms and affects F-Asn concentration is tested. 16S rRNA gene community profiling is conducted on mice that have been treated with streptomycin, or that have become inflamed by *Salmonella* infection (strep-treated C57BL/6 model and non-strep-treated CBA/J model) or DSS administration (DSS is Dextran Sulfate Sodium which increases the permeability of the mucosal barrier allowing normal microbiota to contact the epithelium and trigger an inflammatory response). Streptomycin treatment or inflammation may result in a decrease in the relative abundance of some putative F-Asn utilizing microbes, resulting in an increase in the concentration of F-Asn. To identify taxa that are sensitive to the antibiotic/inflammation treatment and are also capable of utilizing F-Asn (either via fermentation or respiration), the 16S rRNA abundance profiles are linked to assembled genomes via phylogeny (from single copy conserved markers 100, or 16S rRNA). Furthermore, using MS to measure the F-Asn concentration in each of these communities confirms that when taxa that can utilize F-Asn decrease, the concentration of F-Asn increases, except in those instances where *Salmonella* is present and consumes F-Asn.

Because a fra mutant of *Salmonella* has at least a 1,000-fold fitness defect in mouse models of inflammation, blocking the ability of *Salmonella* to obtain F-Asn will dramatically reduce the severity and duration of disease symptoms. Several potential strategies to block F-Asn acquisition by *Salmonella* have been considered. One possibility is a screen for small molecule compounds that block the activity of the Fra enzymes, as described in a preceding Example. Another possibility is to simply use the purified enzymes (FraE, FraD, and FraB) as a therapeutic. These enzymes would be modified from their natural form. This would be analogous to Lactaid, which breaks down lactose for people with lactose-intolerance. With F-Asn in the lumen broken down to glucose-6-P and aspartate, the rest of the microbiota could then compete with *Salmonella* for these breakdown products.

An alternative outcome to the metagenomic experiments is that the microbes that utilize F-Asn are not sensitive to streptomycin or inflammation. In this instance, *Salmonella* likely increases in abundance because of greater yields from respiratory metabolism. Whole genome reconstructions support this result, demonstrating that the F-Asn utilizers encode the capacity to ferment, and not respire, F-Asn. Fermentation and respiratory pathways have been demonstrated in community genomic reconstructions. The metagenomic profiling may show the typical microbiota disruption observed with *Salmonella* infection, or DSS-mediated inflammation, in which many taxa decrease in abundance, while the F-Asn utilizers increase in proportion as they ferment F-Asn; but not nearly as rapidly or dramatically as *Salmonella*.

The present embodiments provide insight into the enzymology of the soluble enzymes involved in F-Asn utilization and the FraR regulator, thus setting the stage for future high-throughput screening of small molecule libraries for inhibitors. Using sequence alignments of the Fra enzymes and Phyre2 (Protein Homology/AnalogY Recognition Engine), high-confidence tertiary structure models for the asparginase, kinase and deglycase have been constructed, and conserved residues likely to be critical for structure and function have been identified. This allows further mutagenesis of these residues, and examination of the effects on function. Fold predictions can also be exploited using inhibitor data to build a low-resolution pharmacophore model that identifies interactions required for potency and specificity. F-Asn utilization potential across microbiome communities can be profiled, and the inventory correlated to F-Asn abundance profiles to provide explanations for how *Salmonella* outcompetes other taxa-either *Salmonella* respires tetrathionate while its competitors ferment, or the inflammation initiated by *Salmonella* actually eliminates the competition. A similar outcome might be engendered by streptomycin, which causes susceptibility of mice to *Salmonella*. *Lactobacillus reuteri* engineered to utilize F-Asn may have an enhanced capability to prevent or reduce the severity of *Salmonella* infection in mice, which will set the stage for future human trials. Highlighting how a single nutrient (that can furnish both C and N) can be so critical to *Salmonella* and the interplay of other microbes in this utilization may inspire work on the utilization of other Amadori products by other microbes.

Example 10. Diagnosis of *Salmonella* in Human Stool Using Selective Medium

The non-typhoidal serovars of *Salmonella* utilize the unusual nutrient: F-Asn. This Example provides a minimal medium containing F-Asn and tetrathionate compared with the industry standard "tetrathionate broth" for enrichment of *Salmonella* from human fecal samples. Although numerous bacteria can ferment in tetrathionate broth, which is a rich medium with numerous carbon sources, *Salmonella* is enriched due to its ability to respire using tetrathionate instead of oxygen. In contrast, only *Salmonella* grows in the minimal F-Asn medium described herein. Replacement of the carbon sources in tetrathionate broth with F-Asn improved the selectivity of the medium for *Salmonella*. Surprisingly, the counts of all other bacteria in the fecal sample were reduced to zero, and thus the minimal F-Asn medium was far more selective than anticipated. This inhibition of non-*Salmonella* CFUs required F-Asn, thiosulfate, and iodine (pre-formed tetrathionate was not inhibitory), suggesting that F-Asn may be modified to form a toxic product, although a modified form was not detected using mass-spectrometry. Although minimal medium containing thiosulfate, iodine, and F-Asn was far more selective for *Salmonella* than tetrathionate broth, the growth rate of *Salmonella* in this minimal medium, and its final population density, were low. To combine the rapid growth rate provided by the rich tetrathionate broth with the selectivity provided by the newly discovered toxicity observed with F-Asn medium, F-Asn was combined in a tetrathionate broth with adjusted iodine concentration. The result was a rich medium that allowed *Salmonella* to grow rapidly while inhibiting all other bacteria in the fecal samples. These findings show that the F-Asn medium described herein improves the speed and accuracy of *Salmonella* diagnostics, and further provides insight regarding the biology of the inflamed intestine.

Oxoid™ Tetrathionate Broth Base (Thermo Scientific™, Waltham, Mass.) was prepared as instructed by the manufacturer. M9 minimal media base salts (minimal media contains only inorganic salts, a carbon source, and water) was prepared as follows: 30 g $Na_2HPO_4$, 15 g $KH_2PO_4$, 2.5 g NaCl, 5 g $NH_4Cl$, pH 7.4. Trace elements (10,000×) were prepared as follows: 30 mM $CaCl_2$, 10 mM $ZnSO_4$, 4.5 mM $FeSO_4$, 20 mM $Na_2Se2O_3$, 20 mM $Na_2MoO_4$, 200 mM $MnSO_4$, 10 mM $CuSO_4$, 300 mM $CoCl_2$, and 10 mM $NiSO_4$. Price-Carter et al., 2001. Iodine solution was prepared with 6 g iodine and 5 g potassium iodide in 20 mL of water, then filter sterilized. F-Asn was synthesized as described in Example 1. See Hansen & Berman, 431 Carbohydr. Res. 1 (2016). M9 minimal media without a carbon source was prepared with the following components at the final concentration: 1×M9 salts, 1x trace elements, 2 mM $MgSO_4$, 0.1 mM $CaCl_2$, 1 μl 1M thiamine (Vitamin B1). The following enrichment media were prepared with the above components: (1) M9 minimal media with glucose was prepared by adding glucose to a final concentration of 5 mM into M9 minimal media without carbon source; (2) M9+F-Asn+ potassium tetrathionate was prepared by adding F-Asn (to a final concentration of 5 mM) and 20 g/L of potassium tetrathionate to the M9 minimal media without carbon source; (3) M9+F-Asn+thiosulfate+iodine solution media was prepared by adding F-Asn to a 5 mM final concentration, 30 g/L sodium thiosulfate and 20 mL/L of iodine solution to the M9 minimal media without carbon source; (4) M9+glucose+thiosulfate+iodine solution media was prepared just as the M9+F-Asn+thiosulfate+iodine solution media, but the F-Asn was substituted with a final concentration of 5 mM glucose. Variations of the enrichment media were prepared by excluding different components such as the sodium thiosulfate or the iodine solution.

Human fecal material was obtained from an anonymous healthy donor at the Ohio State University fecal transplant center in accordance with the protocol approved by the Institutional Review Board (OSU 2012H0367). Frozen aliquots of the same fecal sample were used throughout to maintain consistency between experiments.

Media was prepared as described above. An overnight culture of *Salmonella* strain 14028 was serially diluted in sterile 1×PBS. A homogenized fecal sample (100 μl) from a healthy human donor was spiked with 200 CFU of *Salmonella* strain 14028 (spiked), or not (control), and inoculated into 5 ml of enrichment media. The cultures were enumerated by dilution plated at 0 hr, 2 hr, and 24 hr onto LB or XLD agar, after standing incubation at 37° C.

Figure 20A:
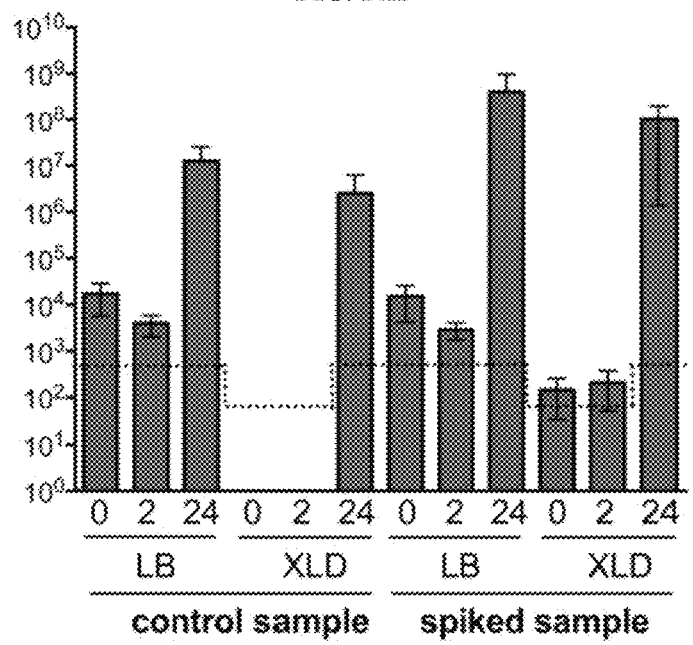
FIG. 20A to FIG. 20F show results from an example in which a homogenized fecal sample (100 μl) from a healthy human donor was spiked with 200 CFU of *Salmonella* strain 14028 (spiked), or not (control), and inoculated into 5 ml of either commercially available tetrathionate broth with added iodine solution (FIG. 20A, FIG. 20B), M9 minimal medium containing F-Asn, sodium thiosulfate and iodine solution (FIG. 20C, FIG. 20D), or M9 minimal medium containing F-Asn without sodium thiosulfate and iodine solution (FIG. 20E, FIG. 20F). Cultures were dilution-plated onto LB or xylose lysine desoxycholate (XLD) agar at 0, 2 hours, and 24 hours after standing incubation at 37° C. Quantitation is shown in FIG. 20A, FIG. 20C, and FIG. 20E; detection limit indicated by dotted line; x-axis: hours; y-axis: CFU/ml. Photographs of the colonies obtained are shown in FIG. 20B, FIG. 20D, and FIG. 20F; each photograph has four rows of plates: LB control, XLD control, LB spiked, and XLD spiked (from top to bottom); each row shows the triplicate dilution plates from the 24 hour time point. The quantitation is from experiments performed in triplicate on two separate occasions with error bars representing the 95% confidence interval of the geometric mean. The photographs are of the plates from one of those two occasions.
Figure 20B:
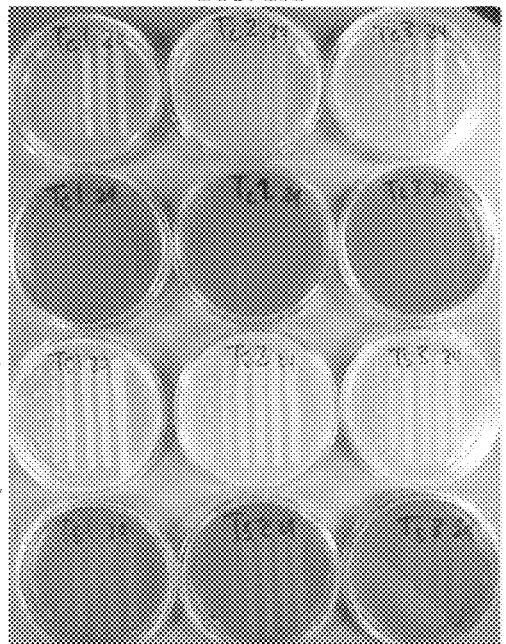

More specifically, cultures of 5 ml of the various media containing a human fecal sample, either spiked or not spiked, with 200 CFU of *Salmonella enterica* serovar *Typhimurium* (strain ATCC14028) were incubated standing at 37° C. for 24 hr. To quantitate *Salmonella*, the cultures were serially diluted and plated on XLD agar. The cultures were also plated on LB agar to determine the total number of culturable bacteria that were present in the samples. See FIG. 20A to FIG. 20F. Two media used an M9 base (Miller, EXPERIMENTS IN MOLEC. GENET. (Cold Spring Harbor Lab., Cold Spring Harbor, N.Y., 1972)), and 5 mM F-Asn, either with or without a mixture of thiosulfate and iodine (to produce tetrathionate). These media were compared with commercially available tetrathionate broth (rich medium that includes a mixture of thiosulfate and iodine to produce tetrathionate). Tetrathionate broth yielded $6 \times 10^7$ CFU of *Salmonella* on XLD plates, and the M9 F-Asn+ thiosulfate and iodine medium yielded $5 \times 10^6$ CFU of *Salmonella* on XLD plates (FIG. 20A, FIG. 20B).

Figure 20C:
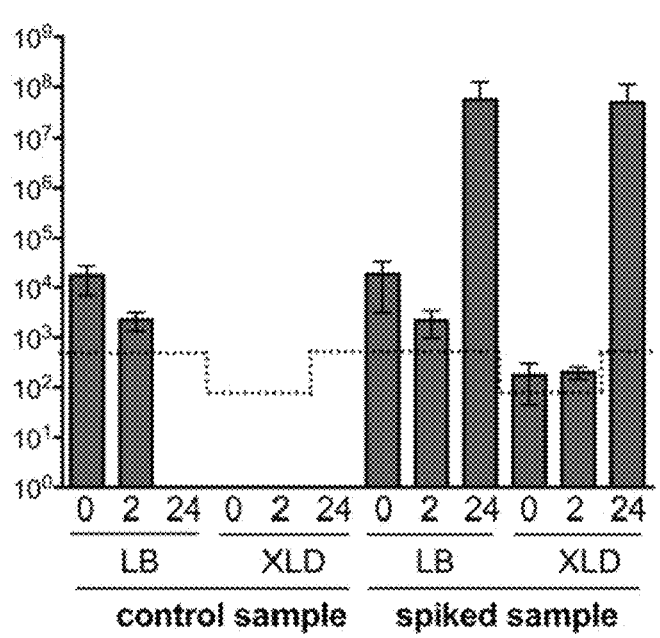
Figure 20D:
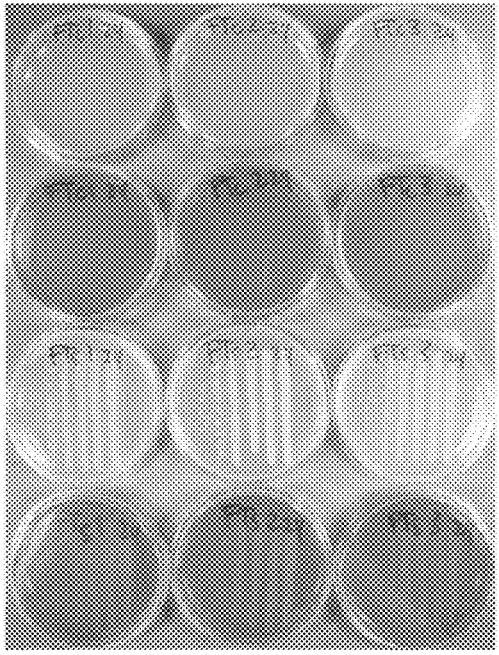
Figure 20E:
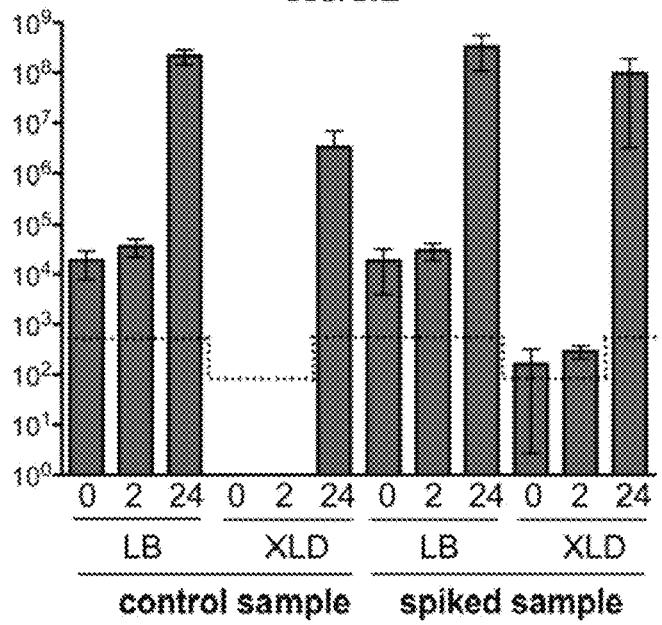
Figure 20F:
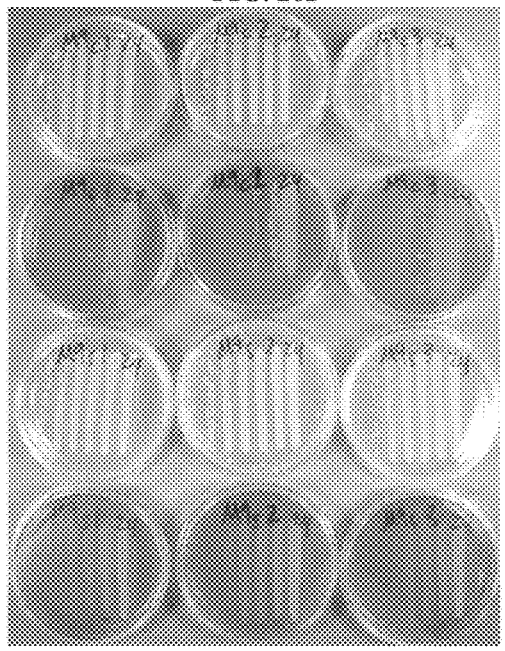

A striking result was obtained, however, with the control cultures that were not spiked with *Salmonella*: using LB plates, $4 \times 10^6$ CFU were recovered from the tetrathionate broth, but zero CFU were recovered from the M9 F-Asn+ thiosulfate+iodine broth (FIG. 20C, FIG. 20D). This suggested that the M9 F-Asn+thiosulfate+iodine medium allowed only *Salmonella* to grow while inhibiting all other organisms in the fecal sample. The M9 F-Asn medium lacking thiosulfate+iodine yielded high numbers of CFU on LB plates, indicating that thiosulfate and iodine are required for inhibiting the growth of the non-*Salmonella* CFUs in the fecal sample (FIG. 20E, FIG. 20F). Additionally, yellow colonies recovered on the XLD plates suggested that *E. coli* was among non-*Salmonella* CFUs. Of the genome sequences available for *E. coli*, however, none appear to encode the genes required for F-Asn utilization, but sequencing of 16S rDNA from several of these yellow colonies revealed that they were indeed *E. coli*. It is not known if these unusual *E. coli*. isolates utilized F-Asn, grew on other carbon sources present in the fecal sample, or did not grow at all in the broth but simply remained present and viable until inoculated onto plates.

Figure 21A:
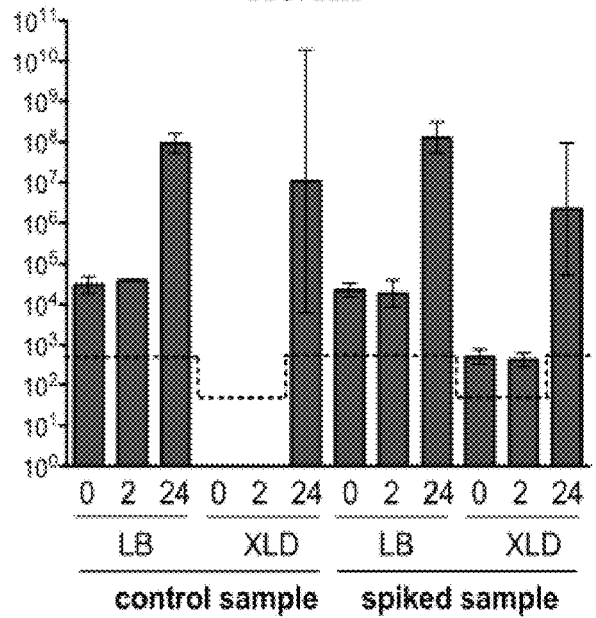
FIG. 21A to FIG. 21H present data obtained when a homogenized fecal sample (100 μl) from a healthy human donor was spiked with 200 CFU of *Salmonella* strain 14028 (spiked), or not (control), and inoculated into 5 ml of M9 minimal medium containing either F-Asn and sodium thiosulfate (FIG. 21A), F-Asn and iodine solution (FIG. 21B), F-Asn and potassium tetrathionate (FIG. 21C), F-Asn, potassium tetrathionate, and iodine solution (FIG. 21D), glucose, sodium thiosulfate, and iodine solution (FIG. 21E), glucose and sodium thiosulfate (FIG. 21F), glucose (FIG. 21G), or glucose and iodine solution (FIG. 21H); y-axis: CFU/ml; x-axis: hours; detection limit indicated by dotted line. After standing incubation at 37° C. for 0, 2 hours, and 24 hours, the cultures were dilution plated onto LB or XLD agar. The results are from triplicate cultures with error bars representing 95% confidence interval of the geometric mean.
Figure 21B:
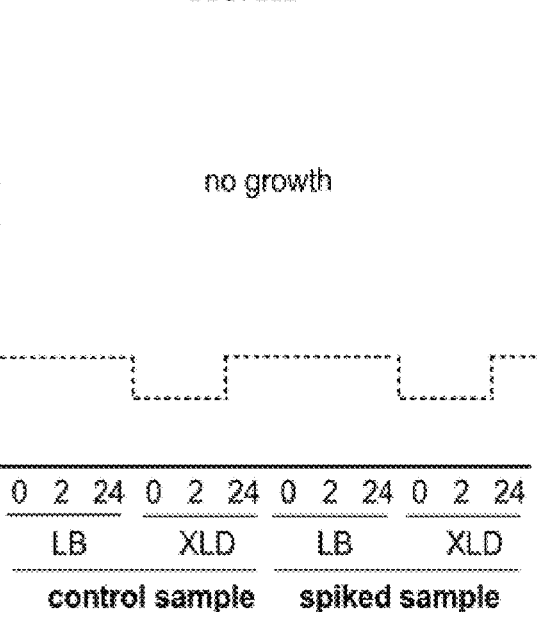
Figure 21C:
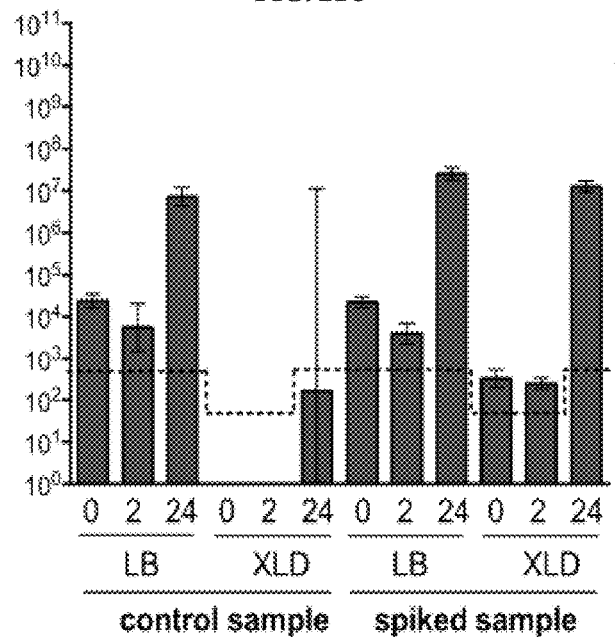
Figure 21D:
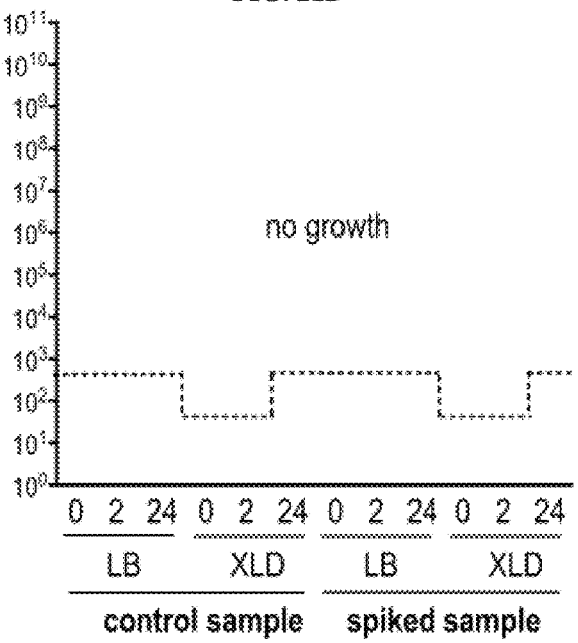
Figure 21E:
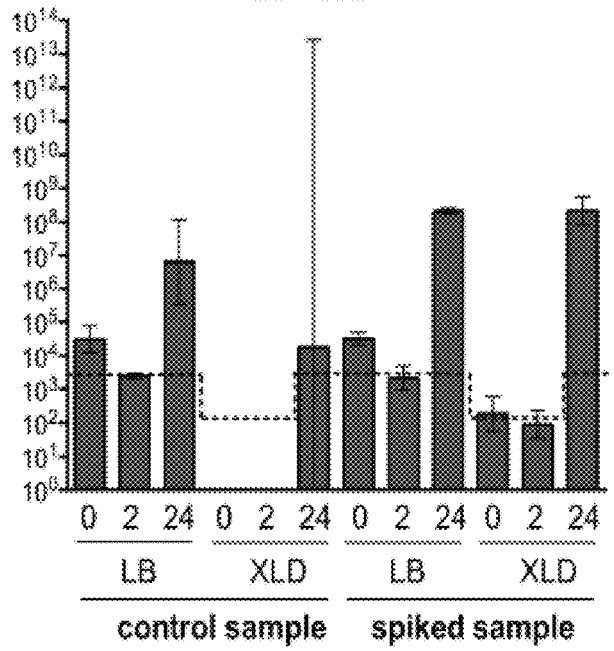
Figure 21F:
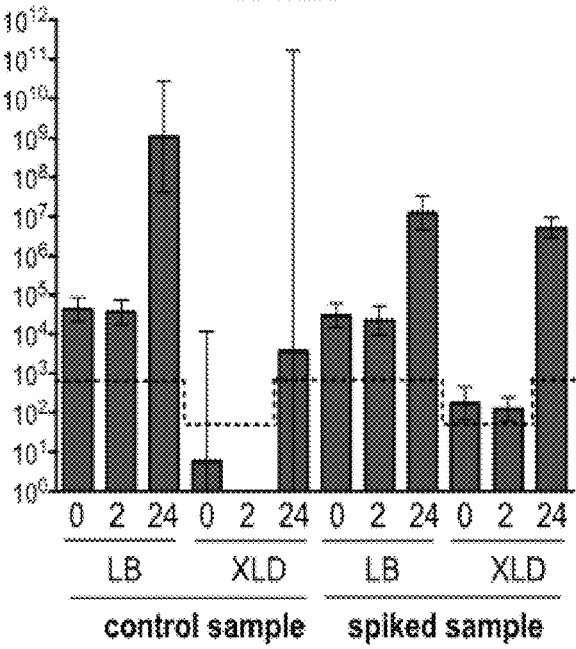
Figure 21G:
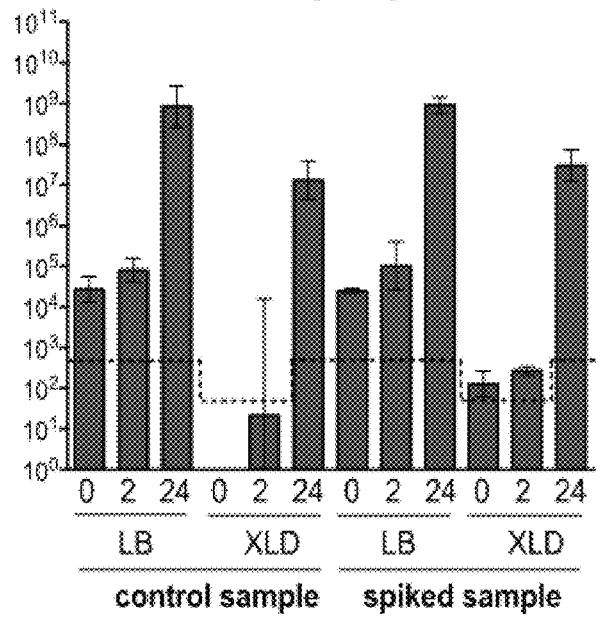
Figure 21H:
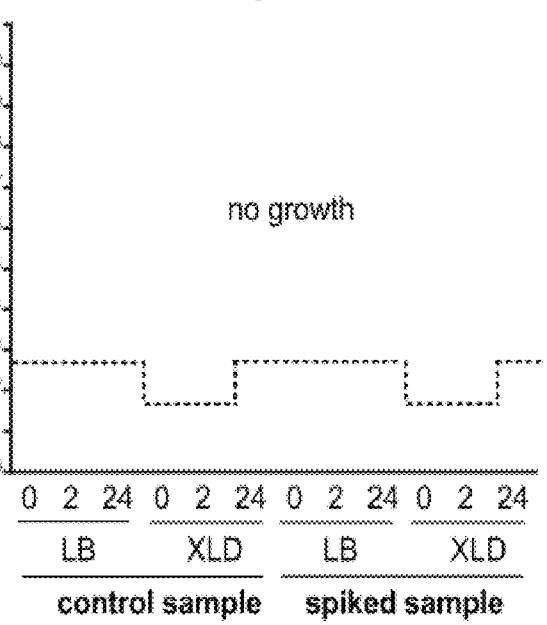

There had been no expectation or suggestion that non-*Salmonella* CFU would be inhibited by any of the media components, only that *Salmonella* would be enriched. Hence, media were tested that lacked either thiosulfate or iodine, or contained potassium tetrathionate in place of thiosulfate and iodine, or that used glucose in place of F-Asn as sole carbon source. FIG. 21A to FIG. 21H. Replacement of thiosulfate and iodine with potassium tetrathionate removed most of the inhibition, although the *E. coli* in the fecal sample was still inhibited (FIG. 21C). Removal of iodine eliminated the inhibitory activity of the F-Asn medium, and non-*Salmonella* CFUs were abundant (FIG. 21F). In contrast, removal of thiosulfate caused this particular medium to become inhibitory to all organisms including *Salmonella* (FIG. 21B, FIG. 21H). These results suggest that the oxidative capacity of iodine is consumed by the presence of the reductant thiosulfate, and this needs to be properly balanced so that there is enough oxidative capacity remaining in the medium to inhibit all organisms except the *Salmonella*. A surprising result was that F-Asn was found to be required for the inhibitory nature of the medium. Replacement of F-Asn with glucose eliminated the inhibition, so that non-*Salmonella* CFUs were abundant, even in the presence of thiosulfate and iodine (FIG. 21E).

Figure 22A:
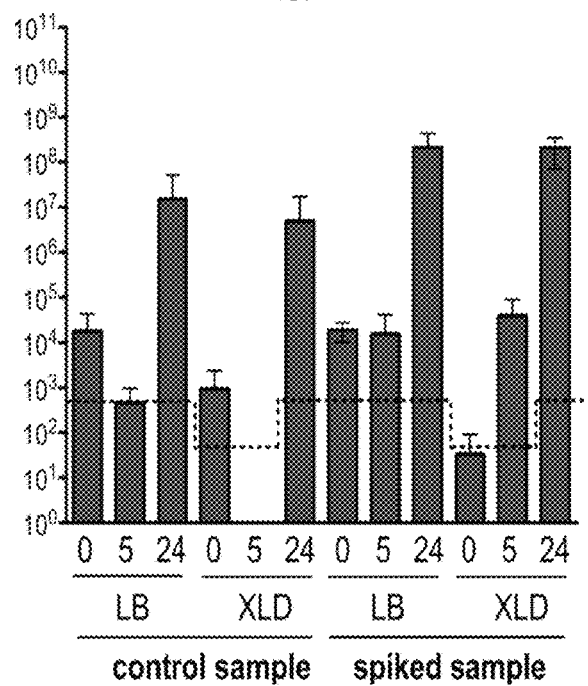
FIG. 22A to FIG. 22D depict results from a homogenized fecal sample (100 μl) from a healthy human donor spiked with 200 CFU of *Salmonella* strain 14028 (spiked), or not (control), and inoculated into 5 ml of commercial tetrathionate broth containing: F-Asn and 1× iodine solution (FIG. 22A), F-Asn and 2× iodine solution (FIG. 22B), F-Asn and 4× iodine solution (FIG. 22C), or F-Asn and 8× iodine solution (FIG. 22D); y-axis: CFU/ml; x-axis: hours; detection limit indicated by dotted line. After standing incubation at 37° C. for 0, 5 hours, and 24 hours, the cultures were dilution plated onto LB or XLD agar. The results shown are from triplicate cultures with error bars representing 95% confidence interval of the geometric mean.
Figure 22B:
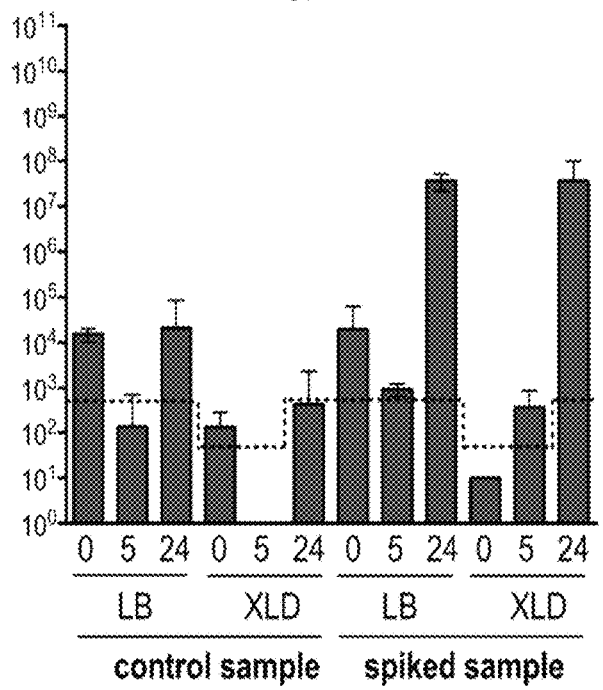
Figure 22C:
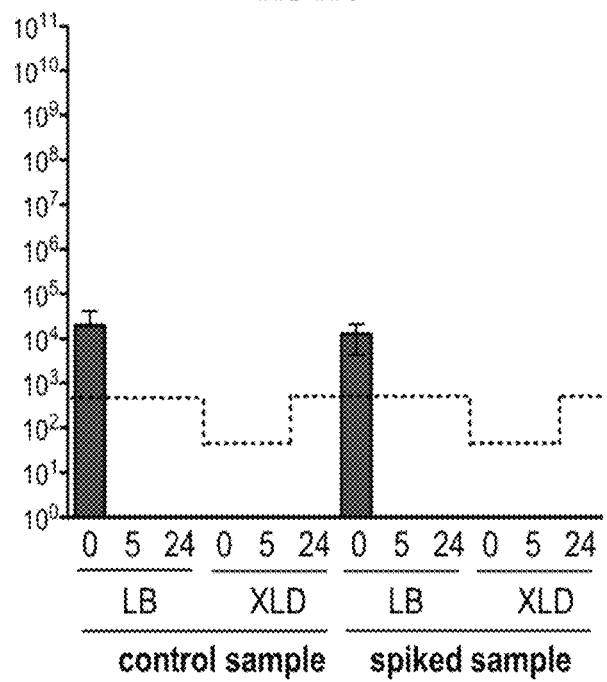
Figure 22D:
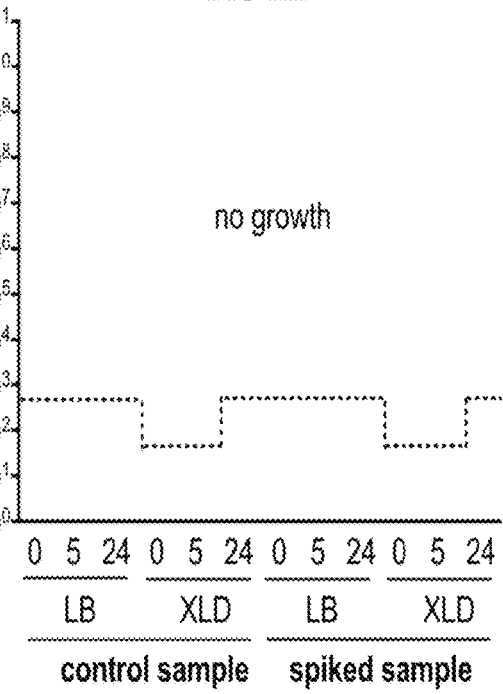

M9 minimal medium containing F-Asn as the sole carbon source, along with thiosulfate and iodine to create tetrathionate, allowed only *Salmonella* to grow, which is a vast improvement over commercially available tetrathionate broth. The total yield of *Salmonella*, however, was 10-fold lower in the M9 F-Asn medium than in a commercially available tetrathionate broth, likely because tetrathionate broth is much richer: comprising peptone. Because the F-Asn media had the unexpected ability to inhibit non-*Salmonella* CFUs, the attributes of each medium was tested by adding F-Asn to commercially available tetrathionate broth: the *Salmonella* should be able to grow to high concentrations on the rich medium, while other organisms should be inhibited by the combination of F-Asn, thiosulfate and iodine. FIG. 22A to FIG. 22D. Simply adding F-Asn did not eliminate non-*Salmonella* CFUs, however, but doubling the typical amount of iodine inhibited the non-*Salmonella* CFUs while allowing the growth of *Salmonella* (FIG. 22B). As in the minimal medium, this inhibitory property required F-Asn. Therefore, the addition of F-Asn to tetrathionate broth with increased iodine greatly enhanced the selectivity of the medium (FIG. 22A to FIG. 22C).

As noted herein, F-Asn is a precursor to acrylamide formation in human foods, with highest concentrations in baked or fried cereals or potatoes, e.g., bread crust, french fries, and potato chips. It is thought that F-Asn forms spontaneously, i.e., without the aid of enzymes, when the open chain form of glucose reacts with the alpha amino of asparagine. Asparagine is a major nitrogen storage and transport compound in plants, and plants with high asparagine concentrations may also have high F-Asn concentrations. F-Asn has been detected in several fruits and vegetables with the highest concentration, to date, found in asparagus (1.4% dry weight), but few studies have measured F-Asn content directly, so it is not clear if acrylamide and F-Asn concentrations always correlate. Lea et al., 150 Ann. Applied Biol. 1 (2007); Eichner et al., 543 ACS Symposium Series (1994); Anet & Reynolds, 10 Aust. J. Chem. 182 (1957).

F-Asn was not known to be utilized as a carbon or nitrogen source for any organism until genes encoding a transport and utilization system for F-Asn were identified in *Salmonella*. Ali et al., 10 PLoS Pathog e1004209 (2014). The fra genes occur in the genomes of non-typhoidal serovars of *Salmonella* as a five-gene horizontally acquired island located between the gor and treF genes. Mutations in the fraB gene of this locus cause attenuation of *Salmonella* fitness in several mouse models in which inflammation occurs, but no phenotype is observed in mouse models that fail to become inflamed. The fraB mutant is attenuated due to the accumulation of a toxic metabolite in the cell during utilization of F-Asn, as described herein. Mutants lacking fraD or the entire fra island do not accumulate this metabolite and are not attenuated in mice. The fra genes are missing or mutated in the typhoidal serovars of *Salmonella* that appear to be undergoing genome reduction as they become more host-adapted; the typhoidal serovars are less likely to cause inflammatory diarrhea during the course of disease and are missing numerous genes involved with anaerobic metabolism. Nuccio & Bäumler, 5 MBio e00929-14 (2014). Bioinformatic searches suggest that two *Citrobacter* species, *freundii* and *rodentium*, may also be able to utilize F-Asn, as well as several members of the class Clostridia. Overall, however, F-Asn utilization remains highly specific to the genus *Salmonella*, and is thus a potentially a valuable compound to be used in the identification and isolation of these organisms.

Several media were formulated based on the use of F-Asn as carbon source for the enrichment of *Salmonella*. How these media would enrich for *Salmonella* in real world settings was modeled by mixing a small number of *Salmonella* with a human fecal sample. *Salmonella* was greatly enriched in M9 minimal F-Asn broth. Surprisingly, addition of thiosulfate and iodine to the medium caused the number of non-*Salmonella* CFU recovered to drop to zero, apparently killing all organisms except *Salmonella* (FIG. 20C). This makes the medium far more specific than was expected. The inhibition of non-*Salmonella* CFU required F-Asn and components to make tetrathionate (thiosulfate and iodine). Pre-formed potassium tetrathionate could not replace iodine and thiosulfate, suggesting that the oxidizing potential of iodine is required.

The requirement for F-Asn and resultant death of non-*Salmonella* suggested that F-Asn itself may become modified to a toxic form. Accordingly, the structure of F-Asn in each of the media was examined (structures examined in mock media that were formulated using water in place of M9 salts to facilitate mass spectrometry), but no modifications to F-Asn were detected using this approach. Although speculative, the toxicity of F-Asn may also play a role in the inflamed intestine and help *Salmonella* compete with other organisms in that environment.

International Standards for *Salmonella* detection, such as ISO 6579:2002, ensure consistent and comparable results across different laboratories for accurate monitoring of *Salmonella* disease burden and its impact on human health at both clinical and economical levels. Current protocols for detecting *Salmonella* typically require 5 to 7 days to complete, and include pre-enrichment, selective enrichment, plating on solid media for presumptive positive colonies, and serotyping. More modern rapid detection methods, while shorter in duration (typically 1 to 2 days), require much higher numbers of *Salmonella* ($10^4$ cells/mL) and have several other disadvantages. Lee et al., 2015. Surprisingly, using F-Asn as carbon or nitrogen source greatly increased the selectivity and specificity of the enrichment media, providing multiple advantages over prior enrichment media. The addition of F-Asn and extra iodine to tetrathionate broth enhanced the specificity of the medium by killing nearly all of the culturable organisms except *Salmonella*. This also improved the growth rate of *Salmonella*, presumably due to the elimination of competing microbes and the addition of F-Asn as carbon source.

Additionally, the F-Asn media described herein yielded no false positives, even when isolating *Salmonella* from human fecal samples. This is significant because false positives are often due to the growth of non-*Salmonella* species, such as *Proteus*. The lack of inhibitory additives, such as antibiotics or dyes, also eliminates the need for pre-enrichment, such as typical with buffered peptone water (BPW). Logistically, the F-Asn enrichment media can be filter-sterilized instead of having to be autoclaved or boiled, alleviating the need for expensive equipment. The F-Asn enrichment media is limited to *Salmonella* species with the capability of utilizing F-Asn as a carbon source: *S. Typhi* and *Paratyphi* serovars are not capable of utilizing F-Asn due to incomplete fra loci. This provides delineation between the metabolic capabilities of serovars that cause gastroenteritis and those serovars that cause enteric fever.

Example 11. Metabolic Intermediate of the F-Asn Utilization Pathway Inhibits Growth of *Salmonella* fraB Mutant Insertions in the *Salmonella enterica* fra locus, which encodes the F-Asn utilization pathway, are highly attenuated in mouse models of inflammation (>1000-fold competitive index). The present Example demonstrates that F-Asn is bacteriostatic to a fraB mutant ($IC_{50}$ 19 µM), but not to wild-type or fra island deletion mutant. More specifically, the presence of FraD kinase and absence of FraB deglycase causes build-up of a toxic metabolite: 6-phosphofructose-aspartate (6-P—F-Asp). Biochemical assays assessed FraB and FraD activities, and mass spectrometry confirmed that the fraB mutant accumulates 6-P—F-Asp. These results, together with the findings that mutants lacking fraD or the fra island are not attenuated in mice, suggest that the extreme attenuation of a fraB mutant stems from 6-P—F-Asp toxicity. *Salmonella* FraB is therefore an excellent drug target, a prospect strengthened by the absence of the fra locus in mammals and most of the gut microbiota.

Figure 8:
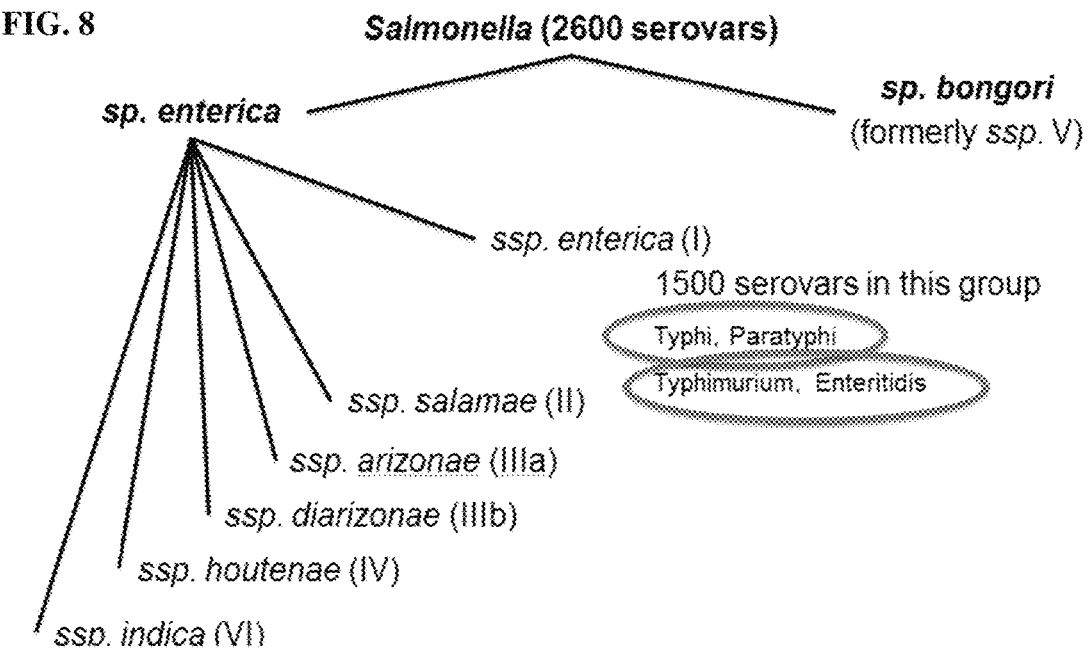
FIG. 8 is a scheme showing the relationship between *Salmonella* serovars.

There are over 2600 serovars of *Salmonella* (see FIG. 8) that can be divided into two pathovars: the gastrointestinal pathovar that causes inflammatory diarrhea, and the extraintestinal pathovar that typically fails to elicit diarrhea but instead causes a systemic infection, Typhoid Fever 1. Nuccio & Baumler, 2014. *Salmonella enterica* serovar *Typhimurium* is the model gastrointestinal serovar, while serovar *Typhi* is the classic example of an extraintestinal serovar. The gastrointestinal serovars of *Salmonella* are among the most common of foodborne illnesses in the United States, and are the leading cause of hospitalization and death. Scallan et al., 17 Emerging Infect. Dis. 7 (2011). Globally, the gastrointestinal serovars are thought to cause 155,000 deaths per year. Kotloff et al., 382 Lancet 209 (2013); Majowicz et al., 50 Clin. Infect. Dis. 882 (2010). There are no vaccines for human use that protect against the gastrointestinal serovars. Strugnell et al., 17 Curr. Opin. Microbiol. 99 (2014); Martin, 25 Curr. Op. Infect. Dis. 489 (2012). Antibiotics are used to treat the very young or elderly, or when there are complications or systemic disease. For uncomplicated cases of Salmonella-mediated gastroenteritis, however, antibiotics are not recommended because the disruption to the normal microbiota may actually benefit Salmonella and increase its shedding. Gopinath et al., 111 PNAS 15780 (2014); Diard et al., Curr. Biol. (2014); Wiström et al., 117 Ann. Intern. Med. 202 (1992). Therefore, drugs that specifically target Salmonella, without disrupting the microbiota, would be extremely useful. Focusing on the unique metabolic capabilities of this pathogen is likely to be productive.

Serovar *Typhimurium* causes inflammation using its two Type 3 Secretion Systems, T3SS1 and T3SS2, encoded within *Salmonella* Pathogenicity Islands 1 and 2 (SPI1 and SPI2), respectively. Stecher et al., 2007. This inflammation, which disrupts the microbiota and presumably removes competitors for nutrients, leads to the oxidation of thiosulfate to tetrathionate that can be used by *Salmonella* as a respiratory electron acceptor (see illustration of FIG. 9). Barman et al., 76 Infect. Immun. 907 (2008); Winter et al., 2010. *Salmonella* then respires while its competitors ferment, allowing *Salmonella* to grow rapidly. Rivera-Chavez & Bäumler, Annu. Rev. Microbiol. (2015); Winter & Bäumler, 2 Gut Microbes 58 (2011). Respiration also increases the number of compounds that *Salmonella* metabolizes: some (e.g., ethanolamine) can be respired but not fermented. Thiennimitr et al., 108 PNAS 17480 (2011).

*Salmonella* can use F-Asn as a sole carbon and nitrogen source. See, e.g., FIG. 3; FIG. 7B. A fraB::kan mutant of *Salmonella* was not able to utilize F-Asn and was extremely attenuated in mouse models of inflammation. fraB is the first gene of the putative fraBDAE locus. The fraR gene, which encodes a transcription factor of the GntR family, is located upstream of fraBDAE and oriented in the same transcriptional direction. FIG. 1. These five genes make up a horizontally acquired island that is not present in *E. coli*. The proposed metabolic pathway catalyzed by these gene products is shown in FIG. 6. As described herein, the four structural genes were mutated individually (or deleted en mass), revealing that each plays a role in F-Asn utilization, although the fraE mutation did not completely eliminate F-Asn utilization. These studies determined that F-Asn is inhibitory to a fraB mutant, but not to the other mutants, and that an intoxicating metabolic intermediate accumulates in the fraB mutant. This intoxication is responsible for the extreme attenuation in mouse models, and identifies FraB as a novel drug target.

The strains plasmids used in this Example are shown in Table 4:

TABLE 4

| Strains and plasmids | | |
|---|---|---|
| Strain | Genotype | Reference or construction |
| 14028 | Wild-type S. enterica subspecies enterica serovars Typhimurium | ATCC |
| HMB176 | 14028 ΔfraBDA80::cam | lambda red mutation of fraBDA made using PCR primers BA2553 and BA2511 and transduced into a clean strain 14028 background |
| HMB182 | 14028 ΔfraE4::kan | lambda red mutation of fraE made using PCR primers BA2537 and BA2515 and transduced into a clean strain 14028 background |
| HMB184 | 14028 ΔfraD4::kan | lambda red mutation of fraD made using PCR primers BA2494 and BA2495 and transduced into a clean strain 14028 background |
| HMB188 | 14028 ΔfraBDA80 | antibiotic cassette in HMB176 was flipped out using pCP20 |
| HMB195 | 14028 ΔfraE4 | antibiotic cassette in HMB182 was flipped out using pCP20 |
| HMB196 | 14028 ΔfraD4 | antibiotic cassette in HMB184 was flipped out using pCP20 |
| HMB205 | 14028 Δfra80::kan | lambda red mutation of fra island made using PCR primers BA2538 and BA2513 and transduced into a clean strain 14028 background |
| HMB206 | 14028 ΔfraB80::kan | lambda red mutation of fraB made using PCR primers BA2552 and BA2553 and transduced into a clean strain 14028 background |
| HMB211 | 14028 ΔfraBD81::kan | lambda red mutation of fraBD made using PCR primers BA2553 and BA2495 and transduced into a clean strain 14028 background |
| HMB215 | 14028 Δfra80 | antibiotic cassette in HMB205 was flipped out using pCP20 |
| HMB218 | 14028 ΔfraBD81 | antibiotic cassette in HMB211 was flipped out using pCP20 |
| HMB247 | 14028 ΔfraA4::kan | lambda red mutation of fraA made using PCR primers BA2510 and BA2511 and transduced into a clean strain 14028 background |
| HMB248 | 14028 ΔfraA4 | antibiotic cassette in HMB247 was flipped out using pCP20 |
| JLD1214 | 14028 IG(pagC-STM14_1502)::cam | Ali et al., 2014 |

| Plasmids | Description | Reference |
|---|---|---|
| pKD46 | $P_{BAD}$ gam bet exo pSC101 oriTS (amp$^r$) | Datsenko & Wanner, 97 PNAS 6640 (2000) |
| pKD3 | FRT-cam-FRT oriR6K (amp$^r$) | Id. |

TABLE 4-continued

Strains and plasmids

| | | |
|---|---|---|
| pKD4 | FRT-kan-FRT oriR6K (amp$^r$) | Id. |
| pCP20 | cI857 λPR flp pSC101 oriTS (amp$^r$ cam$^r$) | Id. |

Bacteria were routinely grown in Luria-Bertani (LB) broth (EMB) or on LB agar plates made by adding 1.5% (w/v) agar (Fisher Bioreagents). Growth studies involving F-Asn used M9 minimal medium: 1×M9 salts, 2 mM MgSO$_4$, 0.1 mM CaCl$_2$, 0.01 mM thiamine, and trace metals. Nuccio & Bäumler, 5 MBio e00929-14 (2014); Miller, EXPER. MOLEC. GENET. (Cold Spring Harbor Laboratory, 1972); Price-Carter et al., 183 J. Bacteriol. 2463 (2001). For the growth assays using minimal media without nitrogen, NH$_4$Cl was not included in the 10×M9 media. As needed, chloramphenicol (cam, 10 μg/mL) or kanamycin (kan, 50 μg/mL) were added to the media.

Regarding the construction of mutants, lambda red mutagenesis was used to generate insertion mutations or in-frame deletions of target genes. Stecher et al., 2007; Datsenko & Wanner, 2000. Oligonucleotides containing forty nucleotides of identity to the target genes were appended to sequences that bind the P1 and P2 sites of pKD4 or pKD3. Barman et al., 76 Infect. Immun. 907 (2008). Primer sequences used are listed in Table 5.

The FRT antibiotic resistance cassette of either pKD3 or pKD4 was amplified by PCR to generate a product with 40 bp identity to target genes on each end. This PCR product was electroporated into strain 14028+pKD46, and homologous recombinants were selected using LB kan at 37° C. Correct insertion of the FRT antibiotic cassette was confirmed by PCR using one primer within the antibiotic cassette and another outside the region of homologous recombination. The bona fide mutants were transduced into strain 14028 using phage P22HTint. The antibiotic cassette was then removed by electroporating pCP20 (ampr), which encodes FLP recombinase, into the strain and plating on LB amp at 30° C. Single colonies were streaked onto LB and incubated at 42° C. to cure the strain of pCP20. PCR was used to verify loss of the antibiotic resistance cassette using primers upstream and downstream of the target gene. Colonies with the correct PCR product were also screened for loss of the antibiotic resistance gene and pCP20 (ampr).

Growth curves were performed using clear, flat-bottom, 96-well plates. Minimal media with the specified carbon source were prepared and overnight cultures were washed twice with sterile water. In each well, 198-μl aliquots of media were inoculated with 2 μl of washed overnight cultures. A Breathe-Easy membrane film (Diversified Biotech) was placed over each 96-well plate. Growth over 18 hr at 37° C. was measured using hourly OD600 measurements in a SpectraMax M5 (Molecular Devices) Microplate Reader and SoftMax Pro 6.1 software.

TABLE 5

Oligonucleotide primers

| Primer | Sequence | Description |
|---|---|---|
| BA2494 | ATTGTAAAGACAAACAAGGAATAATGATGATGTGTAGG CTGGAGCTGCTTC (SEQ ID NO: 12) | forward primer for fraD lambda red mutagenesis |
| BA2495 | TACATTGAGGGACGTAACCTATTGTGCAAACATATGAA TATCCTCCTTA (SEQ ID NO: 13) | reverse primer for fraD and fraBD lambda red mutagenesis |
| BA2510 | AGGAGGAAGTATGTTTTGGACGGAATTATGTTTTATCC TTGTGTAGGCTGGAGCTGCTTC (SEQ ID NO: 14) | forward primer for fraA lambda red mutagenesis |
| BA2511 | TGAATAACAATCAGGCCAGAACCATTTTTCCTATTAAC AGCATATGAATATCCTCCTTAG (SEQ ID NO: 15) | reverse primer for fraA and fraBDA lambda red mutagenesis |
| BA2513 | GCGCACAAGCCTGCATGATTAATACGTACTCATATGAA TATCCTCCTTAG (SEQ ID NO: 16) | reverse primer for fra island lambda red mutagenesis |
| BA2515 | GCCTGCATGATTAATACGTACTGAAATAACTCTGGATC AGCATATGAATATCCTCCTTAG (SEQ ID NO: 17) | reverse primer for fraE lambda red mutagenesis |
| BA2537 | GAGGAAGAAAATGAAAATTAGAGTTTTCATGGCCACCG TGGTGTAGGCTGGAGCTGCTTC (SEQ ID NO: 18) | forward primer for fraE lambda red mutagenesis |
| BA2538 | ATGGATACAAATGATCGAGCAACCCGACAGTAAAAGCG CCGTGTAGGCTGGAGCTGCTTC (SEQ ID NO: 19) | forward primer for fraR and fra island lambda red mutagenesis |
| BA2539 | AATGCTGACATCATACGGTAAACCGTATTTTATCGCCG ACCATATGAATATCCTCCTTAG (SEQ ID NO: 20) | reverse primer for fraR lambda red mutagenesis |
| BA2552 | CCTGATGTAATTAATATTCCACTTTCCACATATAGCGG CGCATATGAATATCCTCCTTAG (SEQ ID NO: 21) | forward primer for fraB lambda red mutagenesis |
| BA2553 | AGAGGAAAGCATGATGGGTATGAAAGAGACAGTTAGCA ATGTGTAGGCTGGAGCTGCTTC (SEQ ID NO: 22) | reverse primer for fraB and fraBDA and fraBD lambda red mutagenesis |

To prepare *Salmonella* extracts, *Salmonella* were grown in 20 ml LB for 16 hr at 37° C. with shaking. The cells were harvested by centrifugation, re-suspended in 20 ml fresh LB supplemented with 5 mM F-Asn, and grown for 30 min at 37° C. with shaking. These cells were subjected to two cycles of centrifugation (5,000 g at 4° C.) and washes with water, before re-suspension in 1 ml of 25 mM HEPES (pH 7.5), 0.1 mM phenylmethylsulfonyl fluoride. Cells were then lysed by sonication (50% output power for 60 s, with cycles of 2 sec on and 5 sec off) (Ultrasonic Processor, Cole-Parmer), and debris removed by centrifuging the cell lysate at 13,000 g for 20 min at 4° C. At this point the samples were split with half for enzymatic assays and half for mass spectrometry measurements. For enzymatic assays, after addition of 0.1 mg/ml BSA, the supernatant was dialyzed against 25 mM HEPES (pH 7.5) at 4° C. with two changes over 60 min. The crude dialysates were used for the activity assays described below. To calculate specific activities, the protein content in the crude dialysates was determined using the Bradford assay with bovine serum albumin serving as the standard. 72 Analyt. Biochem. 248 (1976).

All enzyme assays (40 µl volume) were carried out at 37° C. The measurement of FraB deglycase activity used a glucose-6-phosphate dehydrogenase (G6PD)-based coupled assay. The FraB reaction mixture contained 1 mM 6-P—F-Asp, 25 mM HEPES (pH 7.5), 5 mM $MgCl_2$, 0.1 mM EGTA, 0.5 mM $NADP^+$, 0.15 U G6PD (Sigma, G6378). The reaction was initiated by the addition of a defined amount of crude lysates (up to 40% of the assay volume) obtained from wild-type or mutant *Salmonella* strains. The NADPH generated by G6PD was followed by measuring absorbance at 340 nm and taken as a direct readout of the glucose-6-phosphate produced by FraB. To determine FraD kinase activity, a G6PDH+FraB-based coupled assay was performed. See FIG. 17. The reaction mixture for the kinase assay contained 1 mM fructose-aspartate (F-Asp), 25 mM HEPES (pH 7.5), 25 mM KCl, 1 mM $MgCl_2$, 1 mM dithio-threitol, 1 mM ATP, 0.1 mM EGTA, 0.5 mM $NADP^+$, 0.3 µM recombinant FraB (Sengupta & Gopalan) and 0.15 U G6PD (Sigma, G6378). For both FraB and FraD assays, the reactions were terminated by addition of 6 mM EDTA (final concentration). One unit of activity is defined as the amount of enzyme catalyzing the formation of 1 µmol of NADPH per min. Mean and standard deviation values were calculated from independent assays that used crude lysates from three separate cultures.

Figure 27A:
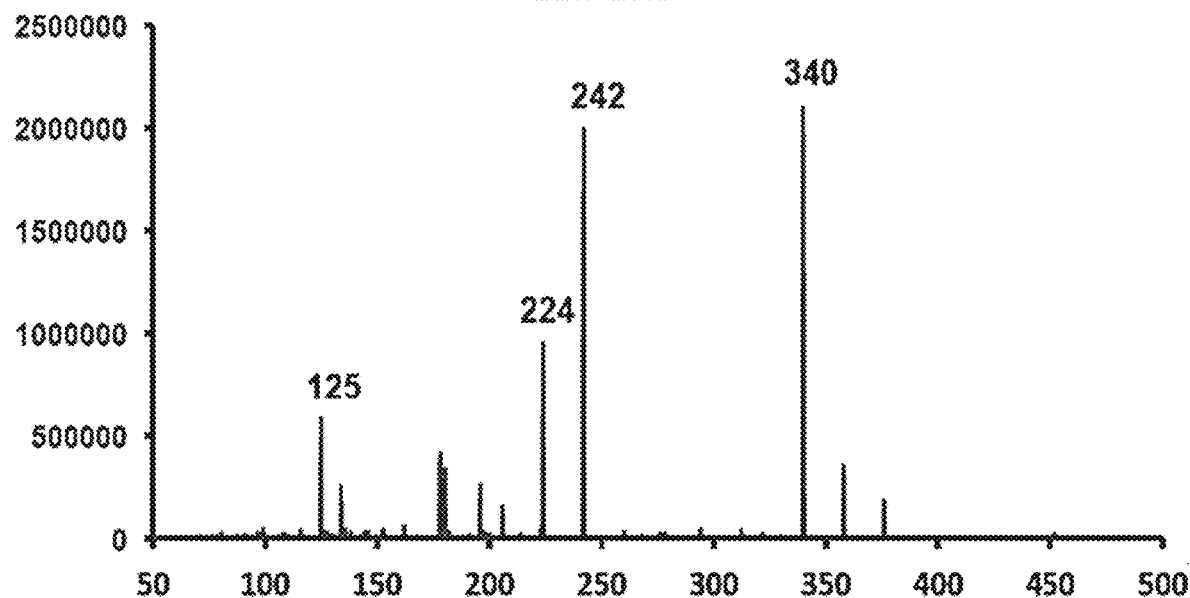
FIG. 27A to FIG. 27D show product-ion MS/MS spectra of m/z 376 (y-axis: intensity; x-axis: m/z). Collision-induced dissociation (15 eV) of *Salmonella* wild-type (14028) metabolome spiked with 320 nmol of 6-P—F-Asp (FIG. 27A); *Salmonella* wild-type (14028) (FIG. 27B); ΔfraB::kan (HMB206) (FIG. 27C); and Δfra island (HMB215) (FIG. 27D). Insets in FIG. 27B and FIG. 27D represent magnifications of signal/noise at this level of detection.
Figure 27B:
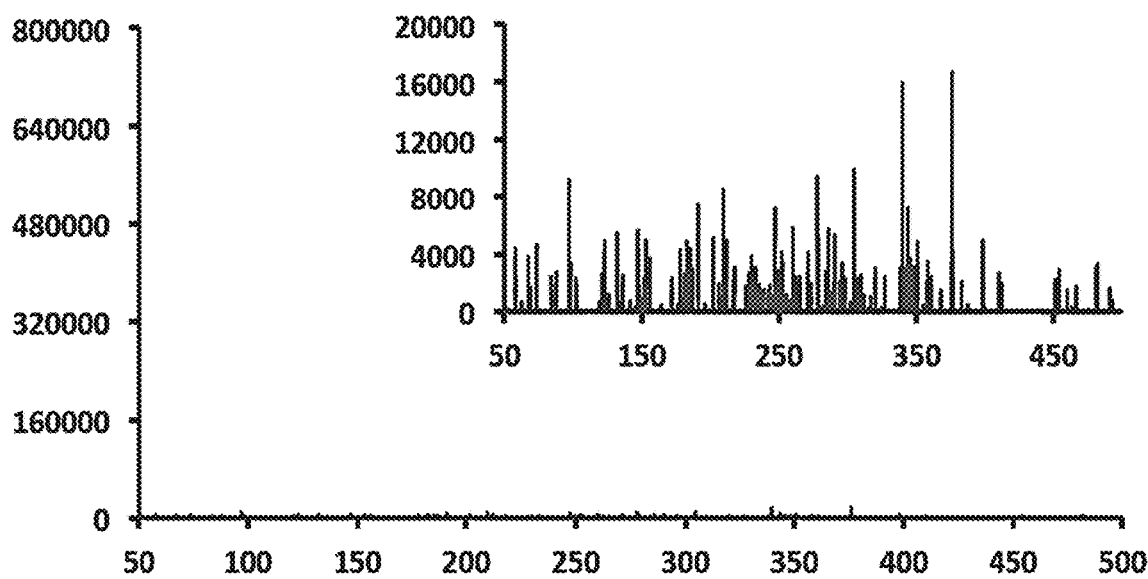
Figure 27C:
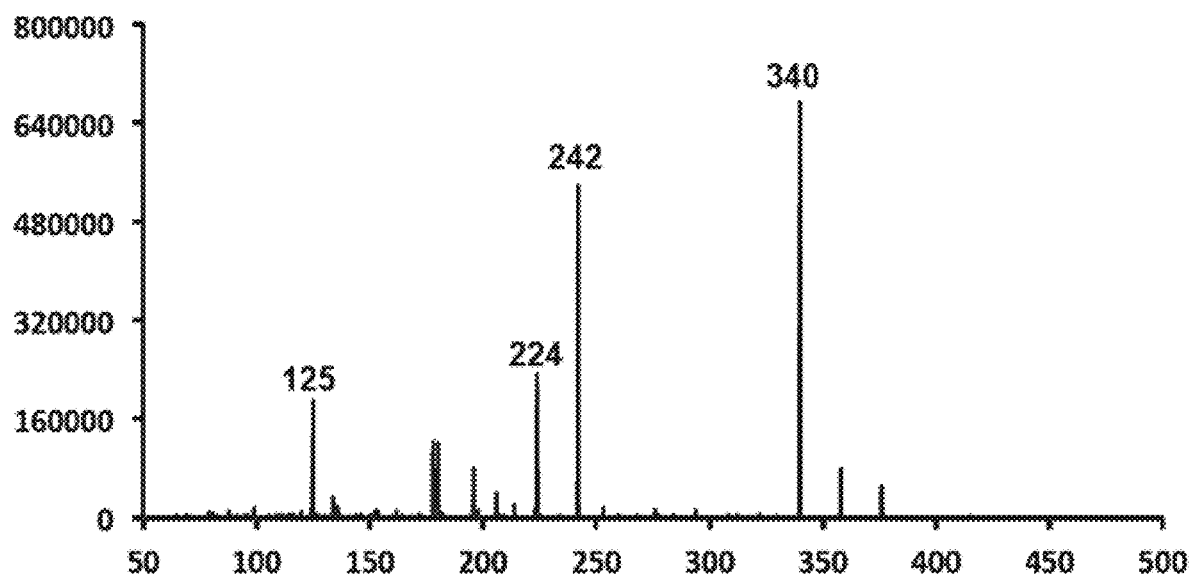
Figure 27D:
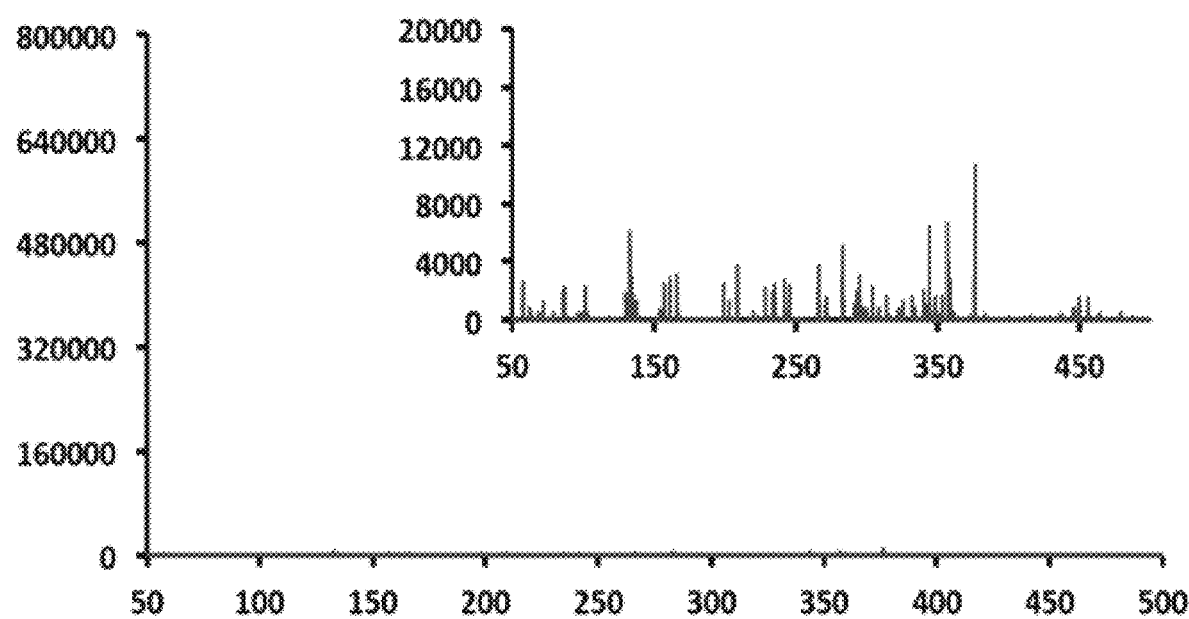
Figure 28A:
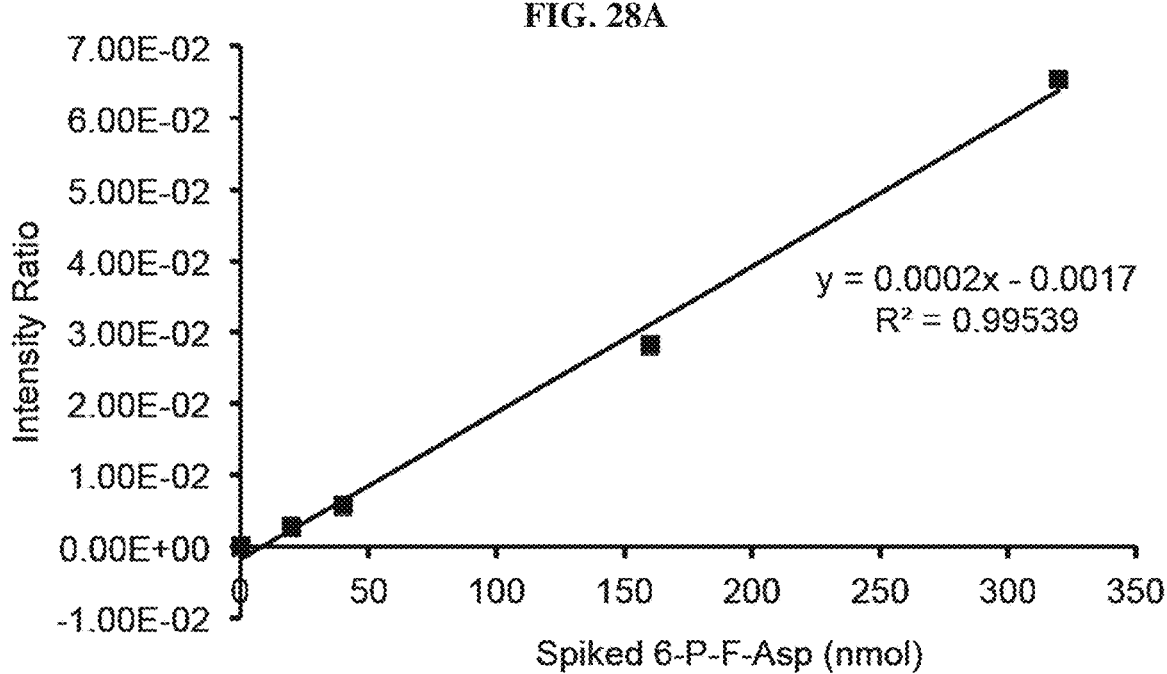
FIG. 28A and FIG. 28B show standard curves constructed by separately plotting the change in peak intensity ratios for two different transitions of 6-P—F-Asp (m/z 376→125 in FIG. 28A; m/z 376→242 in FIG. 28B) as a function of the spiked 6-P—F-Asp. These transitions were normalized using the m/z 301→216 from the [$^{13}$C]—F-Asn internal standard.
Figure 28B:
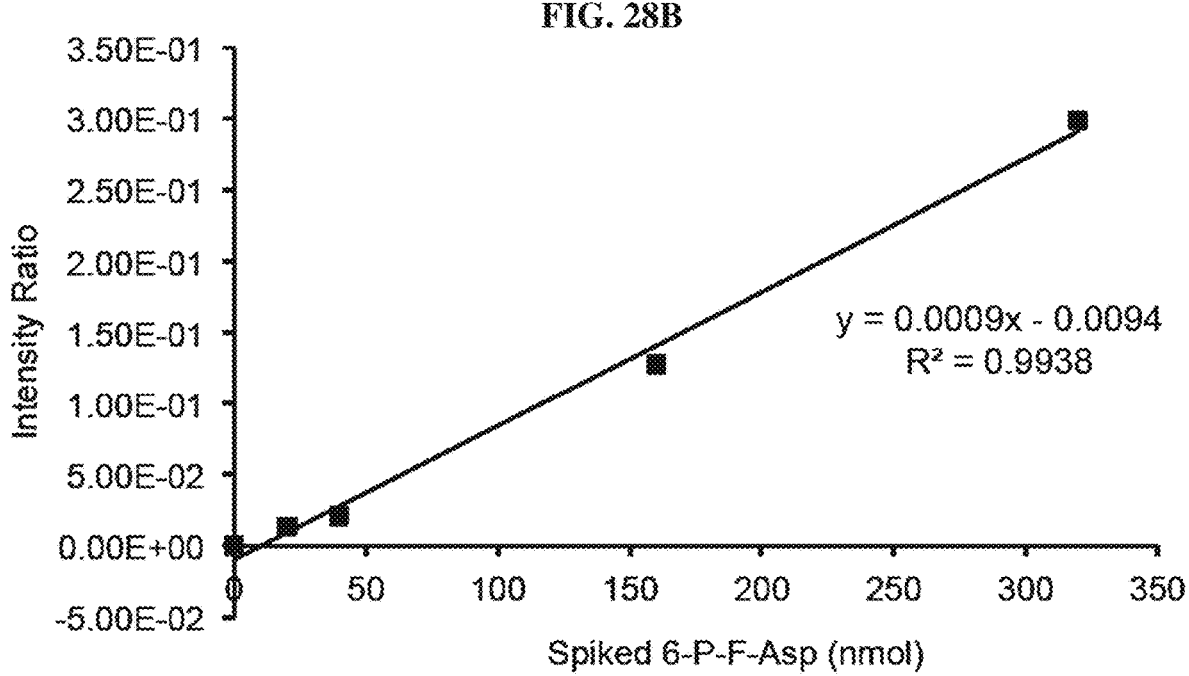

Mass spectrometry was used to measure intracellular 6-P—F-Asp: bacteria were grown as described above for preparation of *Salmonella* extracts and the cell pellets were re-suspended in 20 ml water. The cell suspension was divided into fifteen aliquots and one aliquot was used for each of the following analyses/replicates. Cells were lysed by two cycles of freeze-thaw (30 sec at -20° C., followed by 90 sec at 37° C.), followed by 120 sec of sonication. 600 µl of chilled methanol (Fisher Optima grade, Fisher Scientific) with 16 nmol [$^{13}C$]—F-Asn (internal standard) was added. A group of pooled wild-type *Salmonella* (1/15th of cell pellet suspension) was spiked with 0, 20, 40, 160, or 320 nmol of 6-P—F-Asp to generate a standard curve. The cell suspension was then vortexed and incubated on ice for 30 min, followed by the addition of 600 µl of dichloromethane (Sigma-Aldrich). After being vortexed and centrifuged at 16,200 g for 10 min at 4° C., the upper layer (aqueous phase) was carefully transferred into a new tube with minimal disturbance of the remaining mixture. 600 µl of chilled acetonitrile (Fisher Optima LC/MS grade, Fisher Scientific) was added, followed by vortexing and incubation at -80° C. for 2 hr. These samples were then centrifuged at 16,200 g for 20 min at 4° C. The supernatants were transferred to new tubes and dried under vacuum (Thermo Scientific, SpeedVac Concentrator). Before mass spectrometry analysis, these dried pellets were resuspended in 900 µl methanol:water, 50%:50%, with 0.1% (v/v) formic acid (Thermo Scientific, LC-MS grade). Samples were introduced into a triple quadrupole mass spectrometer (Waters Xevo TQ-S) by direct infusion at flow rate 7 µL/min. The mass spectrometer was operated in positive ion electrospray ionization mode (ESI+) with capillary voltage 3 kV, source temperature 150° C., cone voltage 2 V, cone flow 150 l/h, source offset 2 V, desolvation temperature 350° C., desolvation gas flow 350 l/h and nebulizer gas flow 7 bar. The gas flow rate for the collision cell was 0.15 ml/min. Transitions m/z 376→125 and m/z 376→242 of 6-P—F-Asp with collision energy 15 eV were used for quantitation; m/z 301→216 of [$^{13}C$]—F-Asn with collision energy 13 eV was used for normalization. Acquired data were analyzed using Masslynx 4.1. A total of twenty-two MS/MS scans of each ion were averaged for the measurement of ion intensity. FIG. 24A, FIG. 24B; FIG. 27A to FIG. 27C; FIG. 28A, FIG. 28B.

Figure 26A:
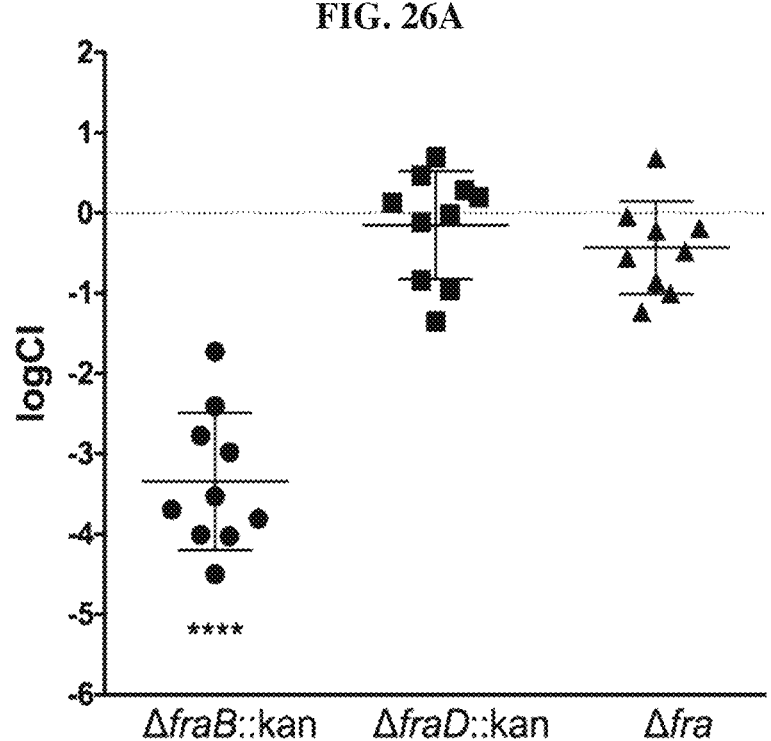
FIG. 26A shows the competitive index (CI) of fra mutants in vivo. Mixtures (1:1) of wild-type JLD1214 and a mutant (HMB206 ΔfraB80::kan, HMB184 ΔfraD4::kan, or HMB205 Δfra80::kan) were administered intragastrically (i.g.) to mice pre-treated with streptomycin. Mice were monitored for survival, and four days post-infection ceca were harvested and plated for CFU. Each point is the CI from one mouse with the geometric mean and standard deviation shown. Statistical significance for each group being different than 0 was calculated using a one-sample, two-tailed t-test (**=P<0.0001).
Figure 26B:
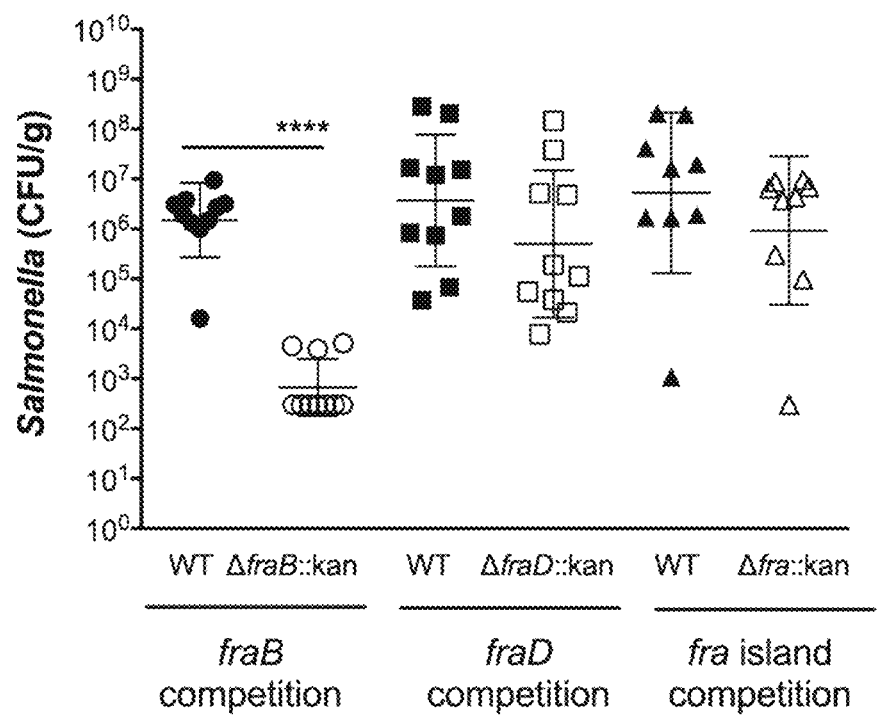
In FIG. 26B, raw CFU counts that gave rise to the CI were log transformed and plotted (limit of detection of 300 CFU). Error bars show the mean and standard deviation (**=P<0.0001).

For competition experiments, a mutant strain, either fraB::kan HMB206, fraD::kan HMB184 or fra80::kan HMB205, were mixed with the isogenic wild-type strain (JLD1214), respectively, and inoculated intragastrically (i.g.) route to Swiss Webster mice that had been treated 24 hr prior with 20 mg of streptomycin. Ceca samples were collected five days post-inoculation, homogenized, and plated on XLD kan and XLD cam plates. Antibiotic resistance differentiated the mutant and wild-type strains. The competitive index was calculated as CI=(cfu mutant recovered/cfu wild-type recovered)/(cfu mutant input/cfu wild-type input). FIG. 26A, FIG. 26B.

All animal work was performed using protocols approved by Institutional Animal Care and Use Committee (IACUC; OSU 2009A0035), and in accord with the relevant guidelines set forth in the PHS "Guide for the Care and Use of Laboratory Animals".

Figure 23A:
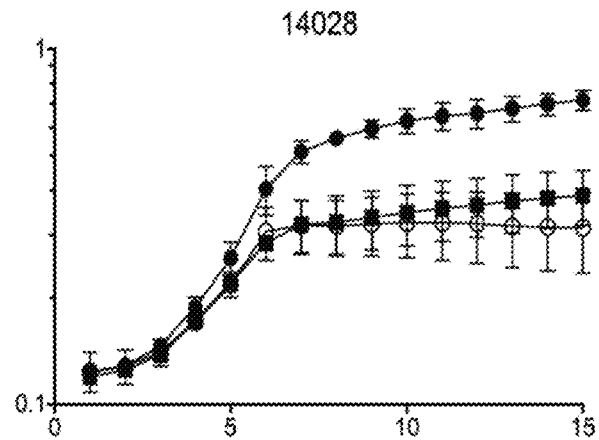
FIG. 23A to FIG. 23H compares growth of fra mutants on different carbon sources. Wild-type *Salmonella* (strain 14028) and isogenic fra mutants were grown in M9 minimal media with ~19 mM ammonium chloride supplemented with either 5 mM glucose (○), 5 mM F-Asn (■), or 5 mM glucose and 5 mM F-Asn (●). All data points are the mean of three biological replicates measured in triplicate (nine total points). y-axis: growth ($OD_{600}$); x-axis: hours; error bars represent standard deviation.
Figure 23B:
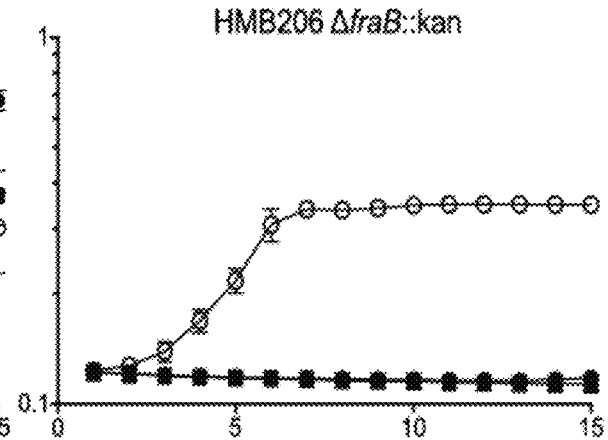
Figure 23C:
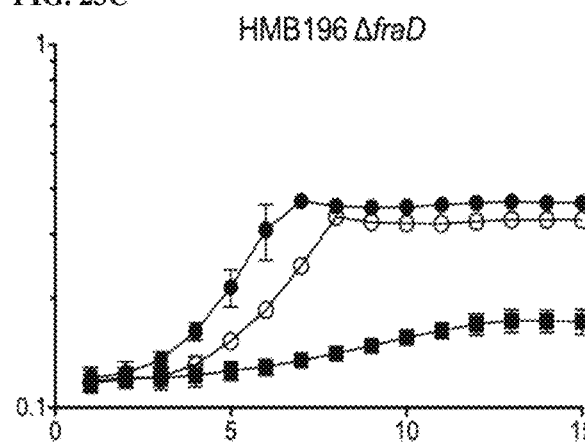
Figure 23D:
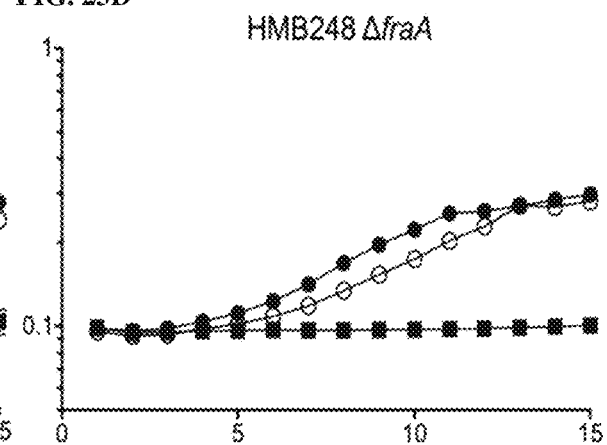

The experiments showed that a fraB mutant of *Salmonella* cannot grow on glucose in the presence of F-Asn (FIG. 23A to FIG. 23H). Wild-type *Salmonella* and an isogenic fraB mutant grow equally well on glucose as sole carbon source. The wild-type grows on F-Asn as sole carbon source (FIG. 2A; FIG. 3; FIG. 23A), but the fraB mutant does not (FIG. 23B). Surprisingly, the fraB mutant does not grow when both F-Asn and glucose were provided together (FIG. 23B). The lack of growth on the dual carbon source medium was specific to the fraB mutant. Mutants lacking fraD, fraE, fraA, or the entire fra island, grew as well as the wild-type in medium containing both F-Asn and glucose (FIG. 23C to FIG. 23E, FIG. 23H). Because a fraD mutation does not yield this phenotype (FIG. 23C), and encodes the enzyme just upstream of FraB in the pathway (per metabolism illustrated in FIG. 6), it appears that the putative metabolic intermediate, 6-phospho-fructose-aspartate (6-P—F-Asp) is toxic to the cell. Deletion of both fraB and fraD simultaneously (FIG. 23F) or fraB, fraD, and fraA (FIG. 23G), relieved the toxicity; consistent with the activity of FraD required to produce the toxic intermediate.

Indeed, 6-P—F-Asp accumulated in the fraB mutant. That F-Asn toxicity results from the presence of FraD and absence of FraB was shown by enzymatic assays and mass spectrometry. Biochemical assays measured FraD and FraB activities in crude lysates prepared from wild-type *Salmonella* and in mutants lacking either fraB, fraD or the entire fra island, all grown for a short duration in 5 mM F-Asn.

These measurements were made possible due to synthesis of F-Asp and 6-P—F-Asp, the substrates of FraD and FraB, respectively, and design of coupled assays that enabled facile colorimetric readouts. Hansen & Behrman, Carbohydr. Res. (2016); Sengupta & Gopalan, 2016. Comparing the wild type and fra island deletion mutant offers a positive and negative control cohort, as shown in Table 6:

TABLE 6

Specific activities of FraD (kinase) and FraB (deglycase) in *Salmonella* wild-type and mutant extracts

|  | FraD (× $10^4$ U/mg) | FraB (× $10^4$ U/mg) |
| --- | --- | --- |
| Wild-type | 2.4 ± 0.13 | 1.3 ± 0.16 |
| ΔfraB::kan | 2.2 ± 0.15 | ND |
| ΔfraD | ND | 0.9 ± 0.06 |
| Δfra | ND | ND |

The specific activities reported are the mean and standard deviation values from three independent experiments.
ND, not detectable.

As shown in Table 6, in the ΔfraB::kan mutant, there is near-wild-type FraD but no FraB activity. In the fraD mutant, there is no FraD activity, and the FraB activity is two-thirds that observed in the wild type; it is possible that deleting the fraD open reading frame might have led to some modest regulatory changes that dampen FraB activity by one-third. Regardless, the overall trends are as expected.

Mass spectrometry (MS) revealed 6-P—F-Asp levels in wild type *Salmonella* and the fra mutants. An aliquot of the cells used for the enzyme assays (described above) were used for the MS measurements. Example data are shown in Table 7:

TABLE 7

6-P-F-Asp (nmol)

Transition m/z 376→125

| Strain | Replicate 1 | Replicate 2 | Replicate 3 | Average | Standard deviation[a] |
| --- | --- | --- | --- | --- | --- |
| wild-type | 8.54* | 8.51* | 8.51* | 8.52* | 0.01 |
| ΔfraB::kan | 80 | 110 | 100 | 100 | 10.0 |
| Δfra island | 8.50* | 8.53* | 8.53* | 8.52* | 0.01 |

Transition from m/z 376→242

| Strain | Replicate 1 | Replicate 2 | Replicate 3 | Average | Standard deviation[b] |
| --- | --- | --- | --- | --- | --- |
| wild-type | 10.44* | 10.45* | 10.45* | 10.45* | 0.002 |
| ΔfraB::kan | 80 | 93 | 89 | 87 | 5.0 |
| Δfra island | 10.48* | 10.46* | 10.45* | 10.46* | 0.01 |

[a]Standard deviation as in FIG. 28A.
[b]Standard deviation as in FIG. 28B.
*These measurements are below 20 nmol, the lowest concentration used for establishing the standard above.

The metabolic intermediate 6-P—F-Asp was detected in the fraB mutant, but was not detected in the wild-type or the fra island deletion mutant (Table 7; FIG. 24, FIG. 24B). Collectively, results from the biochemical assays and mass spectrometry studies established that the product generated by FraD is 6-P—F-Asp, which accumulates in the absence of FraB, as would be expected from the predicted pathway for F-Asn utilization (FIG. 6).

F-Asn was found to be bacteriostatic, not bactericidal, in vitro. To determine if F-Asn was bacteriostatic or bactericidal to the fraB mutant, the 50% and 90% inhibitory concentration ($IC_{50}$ and $IC_{90}$) and the minimum bactericidal concentration (MBC) were characterized. The $IC_{50}$ and $IC_{90}$ were determined by adding increasing concentrations of F-Asn to M9 minimal medium containing glucose as the carbon source. Growth of the fraB mutant was then monitored in these media. F-Asn was inhibitory to growth of the fraB mutant, but not the wild-type or fra island mutant, with an $IC_{50}$ of 19 μM (95% confidence interval of 9 to 40 μM) and $IC_{90}$ of 174 μM (95% confidence interval of 82 to 368 μM) (FIG. 25). To determine the MBC, a small aliquot of these same cultures was dilution-plated onto LB agar. This approach showed whether the bacteria could recover from the inhibition and grow on a non-inhibitory medium. Because *Salmonella* could recover, even at the highest concentrations of F-Asn tested, no MBC was revealed. Moreover, these results indicated that the inhibition experienced by a fraB mutant grown on F-Asn is bacteriostatic and not bactericidal.

The phenotype of a fraB mutant in mice was found to be due to the toxicity of F-Asn. That a fraB mutant had a severe fitness defect (up to 100,000-fold) was shown using competition assays in several mouse models of inflammation (FIG. 14, FIG. 15), a result thought to be a reflection of the importance of F-Asn as a critical nutrient for *Salmonella* in the inflamed intestine. The realization that a fraB mutant is inhibited by low concentrations of F-Asn (FIG. 23B; FIG. 25) provides an alternative explanation based on toxicity of 6-P—F-Asp for the fraB fitness defect in mice. To distinguish between these two mechanisms, a fraB mutant, a fraD mutant, and a mutant lacking the entire fra island was tested for fitness in streptomycin-treated Swiss Webster mice (FIG. 26A and FIG. 26B). The expectation was that the fraD and fra island deletion mutants, which are not inhibited by F-Asn (FIG. 23C, FIG. 23H), would further characterize the importance of F-Asn as a nutrient. Neither the fraD nor the fra island mutants were attenuated in these mice, while the fraB mutant was attenuated about 100,000-fold (FIG. 26A). Therefore, at least in this streptomycin-treated Swiss Webster mouse model, the entire phenotype of the fraB mutant appears to be due to the toxicity of F-Asn rather than an inability to use F-Asn as a nutrient. The decline of the fraB mutant CFU may also suggest that F-Asn is bactericidal, rather than bacteriostatic, to the mutant in vivo (FIG. 26B).

This Example provides experimental evidence to support a F-Asn catabolic pathway (FIG. 6) based on the genes in the fra locus and on a knowledge of the enzymes required for utilization of F-Lys, another Amadori compound. Ali et al., 2014; Wiame et al., 277 J. Biol. Chem. 42523 (2002). Validation of metabolic pathways has typically either assessed the growth of genetic mutants under specific limiting conditions or used biochemical and genetic approaches to cause roadblocks at specific stages in a multi-step conversion to identify the accumulated metabolite; but this Example applied both strategies.

Figure 23E:
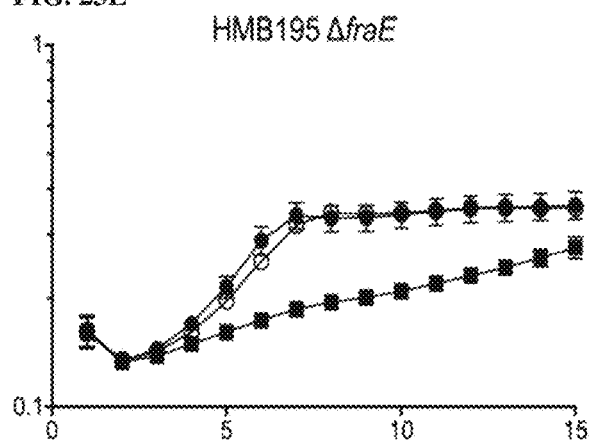
Figure 23F:
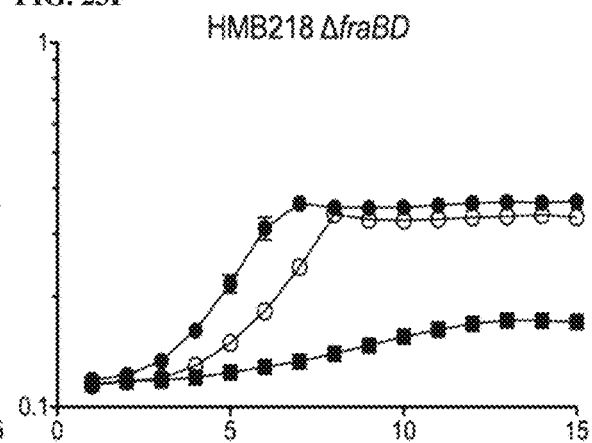
Figure 23G:
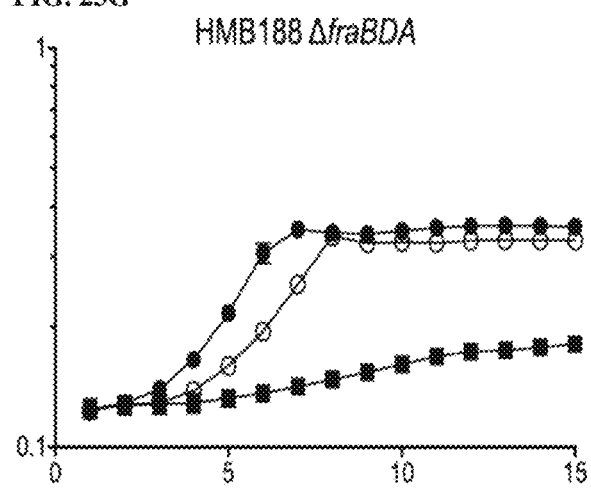
Figure 23H:
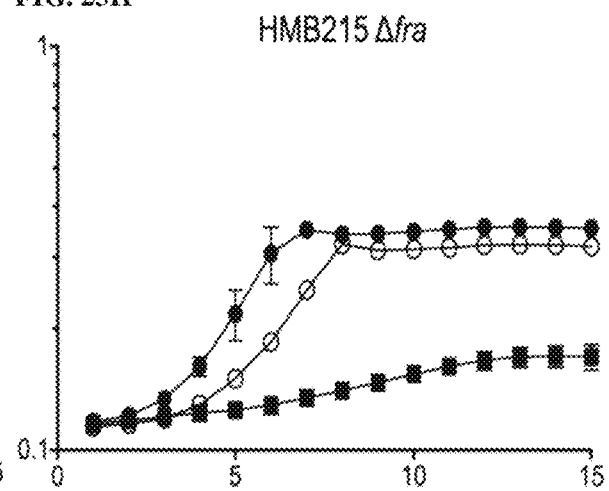

Mutations in fraB, fraD, and fraA eliminated the ability of *Salmonella* to grow on F-Asn, but a mutation in fraE reduced growth on F-Asn (FIG. 23E). Without being bound by theory, the residual growth of the fraE mutant on F-Asn may be due to redundancy from other periplasmic asparaginases. Unlike all of the other fra mutants, the fraB mutant had the unusual property of not being able to grow on glucose if F-Asn was also present (FIG. 23B). Because FraB is the terminal enzyme in the pathway, it appears the substrate of FraB may be toxic to the cell. The use of mass spectrometry and fraB/fraD mutants provided confirmation that the FraB substrate is 6-P—F-Asp and that 6-P—F-Asp accumulates in a fraB mutant (FIG. 6; FIG. 24A, FIG. 24B). Moreover, the presence of FraB deglycase and FraD kinase activities in wild-type *Salmonella* crude extracts confirmed the postulated route for F-Asn metabolism; the complete absence of FraD and FraB activities in the fra island mutant suggested little functional redundancy with respect to F-Asn utilization (Table 6). Recombinant Fra enzymes are expected to provide additional insights into the individual biochemical transformations in the F-Asn utilization pathway.

In addition to furthering the understanding of the F-Asn utilization pathway, results from this Example revealed an unexpected possibility for inhibiting *Salmonella* growth with clear implications for future drug discovery. Mice with intact microbiota are highly resistant to *Salmonella*-mediated inflammation in the gastrointestinal tract. Disruption of the microbiota by agents such as streptomycin, however, causes the mice to be susceptible to *Salmonella*-mediated inflammation. Similarly, germ-free mice and IL10-deficient mice are also susceptible to *Salmonella*-mediated inflammation. Two independently constructed fraB::kan mutants of *Salmonella* were dramatically attenuated in all of the mouse models that are susceptible to inflammation, but not in conventional mice. That both mutants could be complemented with a plasmid encoding the fra island implied that F-Asn is important to *Salmonella* as a nutrient during growth in the inflamed intestine.

This Example clarifies that the phenotype is not solely due to the importance of F-Asn as a nutrient, however, but instead is due to the accumulation of an inhibitory metabolite in the F-Asn utilization pathway: 6-P—F-Asp. Several lines of evidence support this conclusion. For example, observations from growth of different fra mutants in minimal medium containing both glucose and F-Asn as carbon sources proved instructive: a mutant lacking fraD, or the entire fra island, can grow in this medium, while a fraB mutant cannot (FIG. 28, FIG. 30). Additionally, mass spectrometric studies demonstrate that 6-P—F-Asp accumulates to high levels in the fraB mutant, but not in a fra island deletion mutant (FIG. 29). Further, a fraB mutant is extremely attenuated in streptomycin-treated Swiss Webster mice, while a fraD mutant and a mutant lacking the entire fra island have no fitness defect (FIG. 31A and FIG. 31B). Because neither a fraD mutant nor a mutant lacking the entire fra island can grow on F-Asn, their failure to utilize F-Asn in this particular mouse model does not result in a measurable fitness defect, but demonstrates that F-Asn is not an essential nutrient during infection. Moreover, the organization of the fra operon suggests a survival adaptation that prevents build-up of 6-P—F-Asp: the fra genes are encoded in the opposite order of the enzymatic pathway (compare FIG. 1 with FIG. 6), possibly to ensure that FraB is expressed before FraD, thereby avoiding an accumulation of the FraD product.

Except for *Salmonella*, only a few *Citrobacter* and Clostridia seem to have the fra genes, although there is no experimental evidence for F-Asn utilization by the latter. Ali et al., 2014. Thus, FraB represents a potential drug target whose inhibition selectively affects *Salmonella* and perhaps only a few other members of the microbiota. As with numerous other genes involved with anaerobic metabolism in the gut, the fra locus is widely distributed and conserved among the gastrointestinal serovars of *Salmonella*, but is missing or mutated in serovars of the extraintestinal pathovar (the typhoidal serovars).

Given that the $IC_{50}$ of F-Asn for a fraB mutant in vitro is 19 µM, an inhibitor of FraB would work in the presence of at least 19 µM F-Asn, a threshold that is likely to be met in the diet, as evident from the attenuation of a fraB mutant in mice. Ali et al., 2014. The concentration of F-Asn has only been measured in a few human foods, but F-Asn in some vegetables (e.g., asparagus) is as high as 1.4% of dry weight. Anet & Reynolds, 10 Aust. J. Chem. 182 (1957); Richards et al., 195 J. Bacteriol. 4816 (2013). Because the F-Asn concentration in a subject with *salmonellosis* might not be known, a FraB inhibitor could be administered with F-Asn to ensure the inhibition of *Salmonella*. F-Asn would only be available to *Salmonella* during inflammation. When inflammation is relieved, the microbiota would be restored, and F-Asn levels would decrease. Although possible loss-of-function mutations within fraD or fraA would provide resistance to the inhibitor, selection for these mutants would likely be brief, and cease with the alleviation of symptoms; moreover, because F-Asn is not essential there should be little selection pressure for resistance.

Sugar phosphates (e.g., those of rhamnose, glucose, arabinose, and galactose) are known to be toxic to *E. coli* and *Salmonella*, in part due to depletion of glycolytic metabolites or biosynthetic precursors. Richards et al., 2013; Lee et al., 106 PNAS 19515 (2009); Irani & Maitra, 132 J. Bacteriol. 398 (1977); Englesberg et al., 84 J. Bacteriol. 137 (1962); Yarmolinsky et al., 45 PNAS 1786 (1959); Englesberg & Baron, 78 J. Bacteriol. 675(1959). F-Asn catabolic pathway has two major advantages over these other pathways with regard to drug discovery. For example, the F-Asn pathway is more specific to *Salmonella*, so fewer members of the microbiota are likely to be adversely affected by an inhibitor. Further, the toxicity of the glucose and galactose catabolic pathways can be overcome by the addition of other nutrients in vitro. Richards et al., 2013; Lee et al., 2009; Bobrovskyy & Vanderpool, 4 Front Cell Infect. Micro. 61 (2014); Lee et al., 5 MBio e00972-13 (2014). The observation that only the F-Asn utilization pathway was identified in transposon site hybridization screening in mice supports the conclusion that F-Asn toxicity cannot be overcome by the presence of other nutrients that are available in the inflamed intestine. A FraB inhibitor might also be bactericidal to *Salmonella* in vivo, rather than bacteriostatic as seen in vitro. This is suggested by the precipitous decline of fraB mutant CFU from the mice (FIG. 26B). There may be additional stressors in the inflamed intestine, not present in the in vitro assays, that combine with 6-P—F-Asp toxicity to kill the *Salmonella* cell.

Although the foregoing embodiments have been described in some detail by way of illustration and examples for purposes of clarity and understanding, it will be clear to one of skill in the art that certain changes and modifications may be practiced within the scope of the invention which is limited solely by the appended claims.

We claim:

1. A method of selecting an agent that inhibits the expression or function of the fra locus of *Salmonella enterica* comprising: (a) determining whether the agent (i) inhibits expression of fraA, fraB, fraD, fraE, or fraR; (ii) inhibits function of FraA, FraB, FraD, FraE, or FraR; (iii) induces expression of fraA, fraB, fraD, fraE, or fraR; or (iv) induces function of FraA, FraB, FraD, FraE, or FraR; and (b) selecting the agent.

2. The method of claim 1, wherein the method comprises at least one of: (a) exposing live *Salmonella* to the agent in the presence of F-Asn or F-Asp; (b) assaying the biochemical reaction of purified FraB to the agent in the presence of the F-Asn or F-Asp; or (c) obtaining a three-dimensional structural model of FraB and using the structural model for designing or evaluating the structure of the agent.

3. The method of claim 1, wherein the agent inhibits the expression or function of FraB.

4. The method of claim 1, wherein the agent is a small molecule or an antigen-binding molecule.

5. The method of claim 1, wherein the method further comprises exposing live *Salmonella* to the agent in the presence of F-Asn or F-Asp or in the presence of the F-Asn or F-Asp and a probiotic unaffected by the agent.

* * * * *